(12) United States Patent
Grainger et al.

(10) Patent No.: US 6,989,435 B2
(45) Date of Patent: Jan. 24, 2006

(54) COMPOUNDS AND METHODS TO INHIBIT OR AUGMENT AN INFLAMMATORY RESPONSE

(75) Inventors: David J. Grainger, Duxford (GB); Lauren Marie Tatalick, Redmond, WA (US)

(73) Assignee: Cambridge University Technical Services Ltd., Cambridge (GB)

( * ) Notice: Subject to any disclaimer, the term of this patent is extended or adjusted under 35 U.S.C. 154(b) by 241 days.

(21) Appl. No.: 08/927,939

(22) Filed: Sep. 11, 1997

(65) Prior Publication Data

US 2001/0006640 A1 Jul. 5, 2001

(51) Int. Cl.
*C07K 7/00* (2006.01)
*C07K 7/02* (2006.01)
*C07K 7/06* (2006.01)
*C07K 7/50* (2006.01)
*C07K 7/64* (2006.01)

(52) U.S. Cl. ............... 530/328; 530/300; 530/323; 530/324; 530/327; 530/317; 435/69.5; 435/70.1; 435/71.1; 435/71.2; 435/325; 435/252.3; 435/320.1; 435/91.2

(58) Field of Classification Search .......... 530/300, 530/323, 324, 327, 328, 317; 435/69.5, 70.1, 435/71.1, 71.2, 325, 252.3, 320.1, 91.2, 471
See application file for complete search history.

(56) References Cited

U.S. PATENT DOCUMENTS

| | | | |
|---|---|---|---|
| 4,108,855 A | 8/1978 | Magó nee Karácsony et al. | 260/285.5 |
| 4,724,232 A | 2/1988 | Rideout et al. | 514/50 |
| 4,737,580 A | 4/1988 | Twardzik et al. | 530/388 |
| 4,774,318 A | 9/1988 | Marquardt et al. | 530/324 |
| 5,079,228 A | 1/1992 | Cohen et al. | 514/12 |
| 5,155,038 A | 10/1992 | Eyal et al. | 435/240.2 |
| 5,190,918 A | 3/1993 | Deutch et al. | 514/15 |
| 5,190,920 A | 3/1993 | Eyal et al. | 514/17 |
| 5,192,744 A | 3/1993 | Bouck et al. | 514/8 |
| 5,202,118 A | 4/1993 | Gillis et al. | 424/85.2 |
| 5,212,073 A | 5/1993 | Rollins et al. | 435/69.5 |
| 5,248,666 A | 9/1993 | Twardzik et al. | 514/12 |
| 5,302,384 A | 4/1994 | Gimbrone, Jr. et al. | 424/85.2 |
| 5,357,041 A | 10/1994 | Roberts et al. | 530/326 |
| 5,401,651 A | 3/1995 | Walz | 435/240.2 |
| 5,426,100 A | 6/1995 | Deutch et al. | 514/15 |
| 5,458,874 A | 10/1995 | Pereira et al. | 424/85.1 |
| 5,459,128 A | 10/1995 | Rollins et al. | 514/8 |
| 5,474,983 A | 12/1995 | Kuna et al. | 514/12 |
| 5,556,757 A | 9/1996 | Alstyne et al. | 435/7.2 |
| 5,571,713 A | 11/1996 | Lyle et al. | 435/240.2 |
| 5,578,714 A | 11/1996 | Pogo et al. | 536/23.5 |

(Continued)

FOREIGN PATENT DOCUMENTS

| | | |
|---|---|---|
| DE | 27 10 246 | 9/1977 |
| EP | 0 281 363 | 9/1988 |
| EP | 0807439 | 11/1997 |
| JP | 36-14610 | 8/1961 |
| JP | 06-025288 | 2/1994 |
| JP | 7-67689 | 3/1995 |
| JP | 9-255570 A | 3/1996 |
| WO | 86/04334 | 7/1986 |
| WO | 90/07863 | 7/1990 |
| WO | 91/08483 | 6/1991 |
| WO | 91/17179 | 11/1991 |
| WO | 92/04372 | 3/1992 |
| WO | WO-92/14455 | 9/1992 |
| WO | 92/20372 | 11/1992 |
| WO | 93/11159 | 6/1993 |
| WO | 94/11014 | 5/1994 |
| WO | 94/20512 | 9/1994 |
| WO | 95/05191 | 2/1995 |
| WO | 95/17420 | 6/1995 |
| WO | 95/17421 | 6/1995 |
| WO | WO 9520973 | * 8/1995 |
| WO | 95/26982 | 10/1995 |
| WO | 96/20722 | 7/1996 |
| WO | 96/22371 | 7/1996 |
| WO | 96/29074 | 9/1996 |
| WO | 97/01350 | 1/1997 |
| WO | 97/12615 | 4/1997 |
| WO | 97/19173 | 5/1997 |
| WO | 97/21812 | 6/1997 |
| WO | 97/22698 | 6/1997 |
| WO | 97/24325 | 7/1997 |
| WO | 97/25427 | 7/1997 |
| WO | 97/29192 | 8/1997 |
| WO | 97/31098 | 8/1997 |
| WO | 97/32019 | 9/1997 |
| WO | 98/12324 | 3/1998 |
| WO | 92/04372 | 3/1999 |
| WO | WO-00/00821 | 1/2000 |

OTHER PUBLICATIONS

Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc.. pp. 126–128 and 228–234.*
Bowie et al (1990) Science vol. 247, pp. 1306–1310.*
George et al., Macro molecular Sequencing & Synthesis Ch. 12, pp. 127–149, Alan R. Ligs, Inc. N.Y., 1988.*
Cunningham et al. Science vol. 244, pp. 1081–1085, 1989.*
Gong, J., et al., "RANTES and MCP-3 Antagonists Bind Multiple Chemokine Receptors", *The Journal of Biological Chemistry*, 271, 10521–10527 (1996).

(Continued)

*Primary Examiner*—Elizabeth Kemmerer
*Assistant Examiner*—Joseph F. Murphy
(74) *Attorney, Agent, or Firm*—Schwegman, Lundberg, Woessner & Kluth, P.A.

(57) ABSTRACT

Isolated and purified chemokine peptides, variants, and derivatives thereof, as well as chemokine peptide analogs, are provided.

2 Claims, 4 Drawing Sheets

U.S. PATENT DOCUMENTS

| | | | |
|---|---|---|---|
| 5,589,458 A | 12/1996 | Jameson et al. | 514/13 |
| 5,597,578 A | 1/1997 | Brown et al. | 424/422 |
| 5,605,671 A | 2/1997 | Lyle et al. | 424/1.41 |
| 5,627,156 A | 5/1997 | Talmadge | 514/13 |
| 5,627,265 A | 5/1997 | Frazier et al. | 530/350 |
| 5,645,837 A | 7/1997 | Jameson et al. | 424/185.1 |
| 5,646,117 A | 7/1997 | Matsushima et al. | 514/12 |
| 5,650,150 A | 7/1997 | Gillies | 424/134.1 |
| 5,661,132 A | 8/1997 | Eriksson et al. | 514/44 |
| 5,663,294 A | 9/1997 | Colman et al. | 530/326 |
| 5,684,032 A | 11/1997 | Elliott et al. | 514/414 |
| 5,705,360 A | 1/1998 | Rollins et al. | 435/69.1 |
| 5,707,814 A | 1/1998 | Levy et al. | 435/7.1 |
| 5,707,815 A | 1/1998 | Charo et al. | 435/7.2 |
| 5,770,609 A | 6/1998 | Grainger et al. | 514/319 |
| 5,811,449 A | 9/1998 | Medford et al. | 514/423 |
| 5,817,911 A | 10/1998 | Williams et al. | 800/2 |
| 5,824,299 A | 10/1998 | Luster et al. | 424/85.1 |
| 5,824,551 A | 10/1998 | Damme et al. | 435/375 |
| 5,824,647 A | 10/1998 | Postlethwaite et al. | 514/13 |
| 5,827,821 A | 10/1998 | Pierschbacher et al. | 514/11 |
| 5,831,032 A | 11/1998 | Schraufstatter et al. | 530/387.9 |
| 5,871,740 A | 2/1999 | Smith | 424/186.1 |
| 5,877,276 A | 3/1999 | Talmadge | 530/324 |
| 5,908,829 A | 6/1999 | Kelly | 514/12 |
| 5,955,485 A | 9/1999 | De Brabander et al. | 514/366 |
| 5,955,492 A | 9/1999 | Thompson et al. | 514/419 |

OTHER PUBLICATIONS

Shibata, Y. et al., "N–Alkylphtalimides: Structural Requirement of Thalidomidal Action on 12–0–Tetradecanoylphorbol–13–acetate Induced Tumor Necrosis Factor α Production by Human Leukemia HL–60 Cells", *Chem. Pharm. Bull.*, 43(1), 177–179 (1995).

Brunden et al., "pH–Dependent Binding of Synthetic β–Amyloid Peptides to Glycosaminoglycans", *J.Neurochem.*, 61, 2147–2154 (1993).

Karpus, W., et al., "Differential CC Chemokine–Induced Enhancement of T Helper Cell Cytokine Production", *The Journal of Immunology*, 158, 4129–4136, (1997).

Maccarana et al., "Mode of Interaction Between Platelet Factor 4 and Heparin", *Glycobiology*, 3, 271–277 (1993).

McFadden, G., et al., "Commentary: New Strategies for Chemokine Induction and Modulation; You Take the High Road and I'll Take the Low Road", *Biochemical Pharmacology*, 54, 1271–1280, (1997).

Mehlop, P.D., et al., "Allergen–induced Bronchial Hyperreactivity and Eosinophilic Inflammation Ocur in teh Absence of IgE in a Mouse Model of Asthma", *Proceedings of the National Academy of Sciences USA*, 94, 1344–1349, (1997).

Sekiguchi et al., "Binding of Fibronectin and Its Proteolytic Fragments to Glycosaminoglycans", *J. Biol. Chem.*, 258, 14359–14365 (1983).

Waltenberger, J., "Modulation of Growth Factor Action— Implications for the Treatment of Cardiovascular Diseases", *Circulation*, 96, 4083–4094, (1997).

Alkhatib et al., "HIV–1 Coreceptor Activity of CCR5 and Its Inhibition by Chemokines: Independence from G Protein Signaling and Importance of Coreceptor Downmodulation", *Virology*, 234, 340–348 (1997).

Auer et al., "Crystallization and Preliminary X–ray Crystallographic Study of Interleukin–8", *FEBS Letters*, 265, 30–32 (1990).

Bacon et al., "Activation of Dual T Cell Signaling Pathways by the Chemokine RANTES", *Science*, 269, 1727–1730 (1995).

Baldwin et al., "Crystal Structure of Interleukin 8: Symbiosis of NMR and Crystallography", *Proc. Natl. Acad. Sci. USA*, 88, 502–506 (1991).

Baldwin et al., "Crystallization of Human Interleukin–8", *The Journal of Biological Chemistry*, 265, 6851–6853 (1990).

Beck–Schimmer et al., "Hyaluronan Induces Monocyte Chemoattractant Protein–1 Expression in Renal Tubular Epithelial Cells", *Journal of the American Society of Nephrology*, 9, 2283–2290 (1988).

Chakravarty et al., "Lysine 58 and Histidine 66 at the C–terminal alpha–Helix of Monocyte Chemoattractant Protein–1 are Essential for Glycosaminoglycan Binding", *The Journal of Biological Chemistry*, 273, 29641–29647 (1988).

Chung et al., "The Three–Dimensional Solution Structure of RANTES", *Biochemistry*, 34, 9307–9314 (1995).

Clore et al., "Comparison of the Solution Nuclear Magnetic Resonance and Crystal Structures of Interleukin–8", *J. Mol. Biol.*, 217, 611–620 (1991).

Cocchi et al., "The V3 Domain of the HIV–1 gp120 Envelope Glycoprotein is Critical for Chemokine–Mediated Blockade of Infection", *Nature Medicine*, 11, 1244–1247 (1996).

Fairbrother et al., "The Solution Structure of Melanoma Growth Stimulating Activity", *Journal of Molecular Biology*, 242, 252–270 (1994).

Gong et al., "Antagonist of Monocyte Chemoattractant Protein 1 (MCP–1) Inhibits Arthritis in the MRL–lp4 Mouse Model", *Journal of Experimental Medicine*, 186, 131–137 (1997).

Gong et al., "Antagonists of Monocyte Chemoattractant Protein 1 Identified by Modification of Functionally Critical NH2–terminal Residues", *J. Exp. Med*, 181, 631–640 (1995).

Gosling et al., "Molecular Uncoupling of C–C Chemokine Receptor 5–Induced Chemotaxis and Signal Transduction from HIV–1 Coreceptor Activity", *Proc. Natl. Acad. Sci. USA*, 94, 5061–5066 (1997).

Hunter et al., "BB–10010: An Active Variant of Human Macrophage Inflammatory Protein–1α With Improved Pharmaceutical Properties", *Blood*, 86, 4400–4408 (1995).

Lukacs et al., "Airway Hyperreactivity is Associated with Specific Leukocyte Subset Infiltration in a Mouse Model of Allergic Airway Inflammation", *Pathobiology*, 64, 308–313 (1996).

Mehlhop et al., "Allergen–induced Bronchial Hyperreactivity and Eosinophilic Inflammation Occur in the Absence of IgE in a Mouse Model of Asthma", *Proceedings of the National Academy of Sciences USA*, 94, 1344–1349 (1997).

Monteclaro et al., "Role of the Amino Terminus in Ligand Binding and Signal Transduction of the Human Monocyte Chemoattractant Protein–1 Receptor", *Circulation Supplement I*, 92, 160 (1995).

Nagamatsu et al., "Hydrolysis of Lysine Peptides in Plasmin", *Chem. Pharm. Bull.*, 22, 2680–2684 (1974).

Noguchi et al., "Isolation and Identification of Acidic Oligopeptides Occurring in a Flavor Potentiating Fraction from a Fish Protein Hydrolysate", *J. Agric. Food Chem.*, 23, 49–53 (1975).

O'Brien et al., "Anti–Human Immunodeficiency Virus Type 1 Activity of an Oligocationic Compound Mediated via gp120 V3 Interactions", *Journal of Virology*, 70, 2825–2831 (1996).

O'Hehir et al., "Regulation of Cytokine and Chemokine Transcription in a Human TH2 Type T–cell Clone During the Induction Phase of Anergy", *Clinical and Experimental Allergy*, 26, 20–27 (1996).

Porshke et al., "The Conformation of Single Stranded Oligonucleotides and of Oligonucleotide–oligopeptide Complexes from their Rotation Relaxation in the Nanosecond Time Range", *Jo. Biomol. Struct. Dyn.*, 2, 1173–1184 (1985).

Postlethwaite et al., "Identification of a Chemotactic Epitope in Human Transforming Growth Factor– Beta1 Spanning Amino Acid Residues 368–374", *Journal of Cellular Physiology*, 164, 587–592 (1995).

Premack et al., "Chemokine Receptors: Gateways to Inflammation and Infection", *Nature Medicine*, 2, 1174–1178 (1996).

Sato et al., "A Simple and Rapid Method for Preliminary Evaluation of In Vivo Efficacy of Anti–HIV Compounds in Mice", *Antiviral Research*, 27, 151–163 (1995).

Selton et al., "Proton NMR Assignments an Solution Conformation of RANTES, a Chemokine of the C–C Type", *Biochemistry*, 34, 5329–5342 (1995).

Simmons et al., "Potent Inhibition of HIV–1 Infectivity in Macrophages and Lymphocytes by a Novel CCR5 Antagonist", *Science*, 276, 276–279 (1997).

Sneller et al., "An Analysis of Forty–Two Wegener's Granulomatosis Patients Treated with Methotrexate and Prednisone", *Arthritis and Rheumatism*, 38, 608–613 (1995).

Szabo et al., "Chemokine Class Differences in Binding to the Duffy Antigen–Erythrocyte Chemokine Receptor", *The Journal of Biological Chemistry*, 270, 25348–25351 (1995).

Taylor et al., "The Mechanism of Action of Corticosteroids in Asthma", *Respiratory Medicine*, 87, 261–277 (1993).

Thompson et al., "Design and Evaluation of Small Peptides Mapping the Exposed Surface of IL–8", *Int. J. Peptide Protein Res.*, 47, 214–218 (1996).

Wang et al., "Induction of Interleukin–8 in Foam Cells Induced by Acetylated LDL", *Circulation Supplement*, 92, 160 (1995).

Wells et al., The Molecular Basis of the Chemokine/Chemokine Receptor Interaction– Scope for Design of Chemokine Antagonists, *Methods: A Companion to Methods in Enzymology*, 10, 128–134 (1994).

Zagorski et al., "Inhibition of Acute Peritoneal Inflammation in Rats by a Cytokine–induced Neutrophil Chemoattractant Receptor Antagonist", *The Journal of Immunology*, 159, 1059–1062 (1997).

Arenzana–Seisdedos, F., et al., "HIV Blocked by Chemokine Antagonists", *Nature*, 383, 400, (Oct. 3, 1996).

Clark–Lewis, I., et al., "Structural Requirements for Interleukin–8 Function Identified by Design of Analogs and CXC Chemokine Hybrids", *J. Biol. Chem.*, 269, 16075–16081, (Jun. 10, 1994).

Cocchi, F., et al., "Identification of RANTES, MIP–1α, and MIP–1β as the Major HIV–Suppressive Factors Produced by CD8$^+$ T Cells", *Science*, 270, 1811–1815, (Dec. 15, 1995).

Jameson, B.A., et al., "A Rationally Designed CD4 Analogue Inhibits Experimental Allergic Encephalomyelitis", *Nature*, 368, 744–745 (Apr. 21, 1994).

Lusti–Narasimhan, M., et al., "A Molecular Switch of Chemokine Receptor Selectivity", *J. Biol. Chem.*, 271, 3148–3153, (Feb. 9, 1996).

Yahi, N., et al., "SPC3, a Synthetic Peptide Derived from the V3 Domain of Human Immunodeficiency Virus Type 1 (HIV–1) gp120, Inhibits HIV–1 Entry into CD4$^+$ and CD4$^-$ Cells by Two Distinct Mechanisms", *Natl. Acad. Sci. USA*, 92, 4867–4871, (May 1995).

Zhang, Y., et al., "A Dominant Negative Inhibitor Indicates that Monocyte Chemoattractant Protein 1 Functions as a Dimer", *Mol. and Cell Biol.*, 15, 4851–4855, (Sep. 1995).

Zhang, Y., et al., "Structure/Activity Analysis of Human Monocyte Chemoattractant Protein–1 (MCP–1) by Mutagenesis", *J. Biol. Chem.*, 269, 15918–15924 (1994).

"Blocking CCR5 Stops M–tropic HIV Infection", *Biotechnology News*, 17, 3 (1997).

Buckley, C.D., "Treatment of Rheumatoid Arthritis", *BMJ*, 315, 236–238 (Jul. 26, 1997).

Clark–Lewis, I., et al., "Platelet Factor 4 Binds to Interleukin 8 Receptors and Activates Neutrophils When its N Terminus is Modified with Glu–Leu–Arg", *Proceedings of the National Academy of Sciences, USA*, 90, 3574–3577, (1993).

Clark–Lewis, I., et al., "Structure–Activity Relationships of Interleukin–8 Determined Using Chemically Synthesized Analogs", *The Journal of Biological Chemistry*, 266, 23128–23134, (1991).

Drazen, J.M., et al., "Treatment of Chronic Stable Asthma with Drugs Active on the 5–Lipoxygenase Pathway", *Int. Arch. Allergy Immunol.*, 107, 319–320 (1995).

Gong, J.–H., et al., "An Antagonist of Monocyte Chemoattractant Protein 1 (MCP–1) Inhibits Arthritis in the MRL–1pr Mouse Model", *J. Exp. Med.*, 186, 131–137 (Jul. 7, 1997).

Grossman, J., et al., "Results of the First U.S. Double–Blind, Placebo–Controlled, Multicenter Clinical Study in Asthma with Pranlukast, a Novel Leukotriene Receptor Antagonist", *Journal of Asthma*, 34, 321–328 (1997).

Hauser, S.L., "Therapeutic Strategies for Multiple Sclerosis", *J. Neurochem., 69, Suppl.*, Abstract A, p. S219 (1997).

Hendeles, L., et al., "Zafirlukast for Chronic Asthma: Convenient and Generally Safe, But Is It Effective?", *The Annals of Pharmacotherapy*, 31, 1084–1086 (Sep. 1997).

Hilliquin, P., et al., "Treatment of Rheumatoid Arthritis with Platelet Activating Factor Antagonist BN 50730", *J. Rheumatol.*, 22, 1651–1654 (1995).

Hogan, S.P., et al., "Cytokines as Targets for the Inhibition of Eosinophilic Inflammation", *Pharmacol. Ther.*, 74, 259–283 (1997).

Hunter, M.G., et al., "BB–10010: An Active Variant of Human Macrophage Inflammatory Protein–1α with Improved Pharmceutical Properties" *Blood*, 86, 4400–4408 (Dec. 15, 1995).

Ishikawa, J., et al., "Effect of YM934, a Novel Potassium–Channel Opener, in Various Experimental Asthma Models in Guinea–pigs", *J. Pharm. Pharmacol.*, 48, 1034–1040 (1996).

Israel, E., et al., "Effect of Treatment With Zileuton, a 5–Lipoxygenase Inhibitor, in Patients With Asthma", *JAMA*, 275, 931–936 (Mar. 27, 1996).

Katz, M.D., et al., "Octreotide, a New Somatostatin Analogue", *Clinical Pharmacy*, 8, 255–273 (Apr. 1989).

Klareskog, L., et al., "Immunopathogenesis and Immunotherapy in Rheumatoid Arthritis: an Area in Transition", *Journal of Internal Medicine*, 238, 191–206 (1995).

Kledel, T.N., et al., "A Broad–Spectrum Chemokine Antagonist Encoded by Kaposi's Sarcoma–Associated Herpesvirus", *Science*, 277, 1656–1659 (Sep. 12, 1997).

Leong, S.R., et al., "Complete Mutagenesis of the Extracellular Domain of Interleukin–8 (IL–8) Type A Receptor Identifies Charged Residues Mediating IL–8 Binding and Signal Transduction", *Journal of Biological Chemistry*, 19343–19348, (1994).

Lowe, P.M., et al., "The Endothelium in Psoriasis", *British Journal of Dermatology*, 132, 497–505 (1995).

Malkowski, M.G., et al., "The Crystal Structure of Recombinant Human Neutrophil–Activating Peptide-2 (M6L) at 1.9–Å Resolution", *The Journal of Biological Chemistry*, 270, 7077–7087 (Mar. 31, 1995).

Miller, E.J., et al., "A Synthetic Peptide which Specifically Inhibits Heat–Treated Interleukin–8 Binding and Chemotaxis for Neutrophils", *Agents Actions*, 40, 200–208 (1993).

Mölling, K., "Naked DNA for Vaccine or Therapy", *J. Mol. Med.*, 75, 242–246 (1997).

Moser, B., et al., "Interleukin–8 Antagonists Generated by N–Terminal Modification", *The Journal of Biological Chemistry*, 268, 7125–7128 (1993).

Myers, L.K., et al., "Collagen–Induced Arthritis, an Animal Model of Autoimmunity", *Life Sciences*, 61, 1861–1878 (1997).

Plater–Zyberk, C., et al., "Effect of a CC Chemokine Receptor Antagonist on Collagen Induced Arthritis in DBA/1 Mice", *Immunology Letters*, 57, 117–120 (1997).

Reiss, T.F., et al., "Effects of Montelukast (MK–0476), a New Potent Cysteinyl Leukotriene ($LTD_4$) Receptor Antagonist, in Patients with Chronic Asthma", *J. Allergy Clin. Immunol.*, 98, 528–534 (Sep. 1996).

Simmons, G., et al., "Potent Inhibition of HIV–1 Infectivity in Macrophages and Lymphocytes by a Novel CCR5 Antagonist", *Science*, 276, 276–279 (Apr. 11, 1997).

Smith, L.J., et al., "Inhibition of Leukotriene $D_4$–Induced Bronchoconstriction in Subjects With Asthma: A Concentration–Effect Study of ICI 204,219", *Clin. Pharmacol. Ther.*, 54, 430–436 (1993).

Spector, S.L., "Leukotriene Activity Modulation in Asthma", *Drugs*, 54, 369–384 (Sep. 1997).

Spector, S.L., et al., "Effects of 6 Weeks of Therapy with Oral Doses of ICI 204,219, a Leukotriene $D_4$ Receptor Antagonist, in Subjects with Bronchial Asthma", *Am. J. Respir. Crit. Care Med.*, 150, 618–623 (1994).

Suissa, S., et al., "Effectiveness of the Leukotriene Receptor Antagonist Zafirlukast for Mild–to–Moderate Asthma", *Ann. Intern. Med.*, 126, 177–183 (1997).

Tamura, G., et al., "Effect of a Potent Platelet–Activating Factor Antagonist, WEB–2086, on Asthma", In: *Platelet–Activating Factor and Related Lipid Mediators*, 2, Nigam, et al., (eds.), Plenum Press, New York, 371–380 (1996).

Valente, A.J., et al., "Characterization of Monocyte Chemotactic Protein–1 Binding to Human Monocytes", *Biochemical and Biophysical Research Communications*, 176, 309–314 (Apr. 15, 1991).

Weber, M., et al., "Deletion of the $NH_2$–Terminal Residue Converts Monocyte Chemotactic Protein 1 from an Activator of Basophil Mediator Release to an Eosinophil Chemoattractant", *J. Exp. Med.*, 183, 681–685 (Feb. 1996).

Wells, T.N.C., et al., "The Molecular Basis of Selectivity Between CC and CXC Chemokines: The Possibility of Chemokine Antagonists as Anti–Inflammatory Agents", *Annals of the New York Academy of Sciences*, 796, 245–257 (Oct. 31, 1996).

Wells, T.N.C., et al., "The Molecular Basis of the Chemokine/Chemokine Receptor Interaction—Scope for Design of Chemokine Antagonists", *Methods: A Companion to Methods in Enzymology*, 10, 126–134 (1996).

Wooley, P.H., et al., "Influence of a Recombinant Human Soluble Tumor Necrosis Factor Receptor FC Fusion Protein on Type II Collagen–Induced Arthritis in Mice", *The Journal of Immunology*, 151, 6602–6607 (Dec. 1, 1993).

Beers, Mark, et al., "Myeloproliferative Disorders...", *The Merck Manual 7th Edition*, (1999), 1474–1476 & 895–902.

Businco, L., et al., "From Alopic Dermatitis to Asthma: The Risl Factors and Preventive Measures", *Pediatric Pulmonology, Supplement*, 16, (1997), 19–20.

Elson, C., et al., "Experimental Models of Inflammatory Bowel Disease", *Gastroenterology*, 109, (1995),pp. 1344–1367.

Fox, Daniel J., "Design, Synthesis, and Preliminary Pharmacological Evaluation of N–Acyl–3–aminoglutarimides as Broad–Spectrum Chemokine Inhibitors in Vitro and Anti–inflammatory Agents in Vivo", *J. Med. Chem.*, 45, (2002), pp. 360–370.

Frecker, M., et al., "Immunological Associations in Familial and Non–Familial Alzheimer Patients and Their Families", *The Canadian Journal of Neurological Sciences*, 21, (1994), pp. 112–119.

Ivacko, J., et al., "Hypoxic–Ischemic Injury Induces Monocyte Chemoattractant Protein–1 Expression in Neonatal Rat Brain", *Journal of Cerebral Blood Flow and Metabolism*, 17, (1997),pp. 759–770.

Jin, D., et al., "Complement 4 Locus II Gene Deletion and DQA1*0301 Gene: Genetic Risk Factors for IgA Nephropathy and Henoch–Schonlein Nephritis", *Nephron*, 73, (1996), pp. 390–395.

Karpus, W., et al., "An Important Role for the Chemokine Macrophage Inflammatory Protein–1alpha in the Pathogenesis of the T Cell–Mediated Autoimmune Disease., Experimental Autoimmune Encephalomyelltis", *The Journal of Immunology*, (1995),pp. 5003–5010.

Kunkel, S., et al., "The role of chemokines in inflammatory joint disease", *Journal of Leukocyte Biology*, 59, (1996),pp. 6–12.

Lucchinetti, C., et al., "Risk factors for developing multiple sclerosis after childhood optic neuritis", *The American Academy of Neurology*, 49, (1997),pp. 1413–1418.

Marone, M., et al., "Influence of body composition on the bone mass of post menopausal women", *Sao Paulo Medical Journal*, 115(6), (1997),pp. 1580–1588.

Marra, F., et al., "Increased Expression of Monocyte Chemotactic Protein–1 during Active Hepatic Fibrogenesis", *American Journal of Pathology*, 152, (1998),423–430.

McGeer, P., et al., "The inflammatory response system of brain: implications for thereapy of Alzheimer and other neurodegenerative diseases", *Brain Research Reviews*, 21, (1995),pp. 195–218.

Naldi, L., et al., "Dietary factors and the risk of psoriasis. Results of an Italian case–control study", *British Journal of Dermatology*, 134, (1996),pp. 101–106.

Ono, K., et al., "Prevention of Myocardial Reperfusion Injury in Rats by an Antibody against Monocyte Chemotactic and Activating Factor/Monocyte Chemoattractant Protein–1", *Laboratory Investigation*, 79, (1999),pp. 195–203.

Paul, W. M., *Fundamental Immunology, Fourth Edition*, Lippincott–Raven Publ., Philadelphia,(1999),184–185.

Paul, William E., "Fundamental Immunology", *3rd Edition*, (1993),pp250, 1311–1312.

Rewers, M, et al., "Newborn screening for HLA markers associated with IDDM: Diabetes Autoimmunity Study in the Young (DAISY)", *Diabetologia*, 39, (1996),pp. 807–812.

Spence, J., "Advances in atherosclerosis", *Bailliere's Clinical Neurology*, 4(2), (1995),pp. 191–205.

Suda, T., et al., "Modulation of Osteoclast Differentiation by Local Factors", *Bone*, 17(2), (1995),pp. 87S–91S.

Verma, M., et al., "Chemokines in acute anterior uveitis", *Current Eye Research*, (1997),pp. 1202–1208.

Watanabe, T., et al.; "Atherosclerosis and inflammation Mononuclear cell recruitment and adhesion molecules with reference to the implication of ICAM–1/LFA pathway in atherogenesis", *International Journal of Cardiology*, 66, (1998),pp. S45–S53.

* cited by examiner

SEQUENCE LISTING

<160> NUMBER OF SEQ ID NOS: 85

<210> SEQ ID NO 1
<211> LENGTH: 12
<212> TYPE: PRT
<213> ORGANISM: Homo sapiens

<400> SEQUENCE: 1

Glu Ile Cys Ala Asp Pro Lys Gln Lys Trp Val Gln
1               5                   10

<210> SEQ ID NO 2
<211> LENGTH: 13
<212> TYPE: PRT
<213> ORGANISM: Homo sapiens

<400> SEQUENCE: 2

Ala Gln Pro Asp Ala Ile Asn Ala Pro Val Thr Cys Cys
1               5                   10

<210> SEQ ID NO 3
<211> LENGTH: 15
<212> TYPE: PRT
<213> ORGANISM: Homo sapiens

<400> SEQUENCE: 3

Ser Tyr Arg Arg Ile Thr Ser Ser Lys Cys Pro Lys Glu Ala Val
1               5                   10                  15

<210> SEQ ID NO 4
<211> LENGTH: 15
<212> TYPE: PRT
<213> ORGANISM: Homo sapiens

<400> SEQUENCE: 4

His Leu Lys Ile Leu Asn Thr Pro Asn Cys Ala Leu Gln Ile Val

<210> SEQ ID NO 5
<211> LENGTH: 14
<212> TYPE: PRT
<213> ORGANISM: Homo sapiens

<400> SEQUENCE: 5

Asp Tyr Phe Glu Thr Ser Ser Gln Cys Ser Lys Pro Gly Val
1               5                   10

<210> SEQ ID NO 6
<211> LENGTH: 15
<212> TYPE: PRT
<213> ORGANISM: Homo sapiens

<400> SEQUENCE: 6

Glu Leu Arg Val Ile Glu Ser Gly Pro His Cys Ala Asn Thr Glu
1               5                   10                  15

<210> SEQ ID NO 7
<211> LENGTH: 10
<212> TYPE: PRT
<213> ORGANISM: Homo sapiens

<400> SEQUENCE: 7

Cys Ala Asp Pro Lys Gln Lys Trp Val Gln
1               5                   10

<210> SEQ ID NO 8
<211> LENGTH: 6
<212> TYPE: PRT
<213> ORGANISM: Homo sapiens

<400> SEQUENCE: 8

Glu Ile Cys Ala Asp Pro
1               5

<210> SEQ ID NO 9
<211> LENGTH: 6
<212> TYPE: PRT
<213> ORGANISM: Homo sapiens

<400> SEQUENCE: 9

Lys Gln Lys Trp Val Gln
1               5

<210> SEQ ID NO 10
<211> LENGTH: 12
<212> TYPE: PRT
<213> ORGANISM: Homo sapiens

<400> SEQUENCE: 10

Glu Ile Cys Leu Asp Pro Lys Gln Lys Trp Val Gln
1               5                   10

<210> SEQ ID NO 11
<211> LENGTH: 12
<212> TYPE: PRT
<213> ORGANISM: Homo sapiens

<400> SEQUENCE: 11

Glu Ile Cys Ala Asp Pro Ser Gln Lys Trp Val Gln
1               5                   10

<210> SEQ ID NO 12
<211> LENGTH: 12
<212> TYPE: PRT
<213> ORGANISM: Homo sapiens

<400> SEQUENCE: 12

Glu Ile Cys Ala Asp Pro Ser Glu Glu Trp Val Gln
 1               5                  10

<210> SEQ ID NO 13
<211> LENGTH: 12
<212> TYPE: PRT
<213> ORGANISM: Homo sapiens

<400> SEQUENCE: 13

Glu Ile Cys Ala Asp Pro Lys Gln Lys Trp Ile Gln
 1               5                  10

<210> SEQ ID NO 14
<211> LENGTH: 12
<212> TYPE: PRT
<213> ORGANISM: Homo sapiens

<400> SEQUENCE: 14

Glu Ile Cys Leu Asp Pro Lys Gln Lys Trp Ile Gln
 1               5                  10

<210> SEQ ID NO 15
<211> LENGTH: 12
<212> TYPE: PRT
<213> ORGANISM: Homo sapiens

<400> SEQUENCE: 15

Cys Pro Ser Leu Glu Asp Ser Phe Ile Gln Val Ala
 1               5                  10

<210> SEQ ID NO 16
<211> LENGTH: 99
<212> TYPE: PRT
<213> ORGANISM: Homo sapiens

<400> SEQUENCE: 16

Met Lys Val Ser Ala Ala Leu Leu Cys Leu Leu Leu Ile Ala Ala Thr
 1               5                  10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                85                  90                  95

Pro Lys Thr

<210> SEQ ID NO 17
<211> LENGTH: 77
<212> TYPE: PRT
<213> ORGANISM: Homo sapiens

<400> SEQUENCE: 17

-continued

```
Ala Gln Pro Asp Ser Val Ser Ile Pro Ile Thr Cys Cys Phe Asn Val
 1               5                  10                  15

Ile Asn Arg Lys Ile Pro Ile Gln Arg Leu Glu Ser Tyr Thr Arg Ile
             20                  25                  30

Thr Asn Ile Gln Cys Pro Lys Glu Ala Val Ile Phe Lys Thr Lys Arg
         35                  40                  45

Gly Lys Glu Val Cys Ala Asp Pro Lys Glu Arg Trp Val Arg Asp Ser
 50                  55                  60

Met Lys His Leu Asp Gln Ile Phe Gln Asn Leu Lys Pro
 65                  70                  75
```

<210> SEQ ID NO 18
<211> LENGTH: 99
<212> TYPE: PRT
<213> ORGANISM: Homo sapiens

<400> SEQUENCE: 18

```
Met Lys Ala Ser Ala Ala Leu Leu Cys Leu Leu Thr Ala Ala Ala
 1               5                  10                  15

Phe Ser Pro Gln Gly Leu Ala Gln Pro Val Gly Ile Asn Thr Ser Thr
             20                  25                  30

Thr Cys Cys Tyr Arg Phe Ile Asn Lys Lys Ile Pro Lys Gln Arg Leu
         35                  40                  45

Glu Ser Tyr Arg Arg Thr Thr Ser Ser His Cys Pro Arg Glu Ala Val
 50                  55                  60

Ile Phe Lys Thr Lys Leu Asp Lys Glu Ile Cys Ala Asp Pro Thr Gln
 65                  70                  75                  80

Lys Trp Val Gln Asp Phe Met Lys His Leu Asp Lys Lys Thr Gln Thr
                 85                  90                  95

Pro Lys Leu
```

<210> SEQ ID NO 19
<211> LENGTH: 92
<212> TYPE: PRT
<213> ORGANISM: Homo sapiens

<400> SEQUENCE: 19

```
Met Gln Val Ser Thr Ala Ala Leu Ala Val Leu Leu Cys Thr Met Ala
 1               5                  10                  15

Leu Cys Asn Gln Phe Ser Ala Ser Leu Ala Ala Asp Thr Pro Thr Ala
             20                  25                  30

Cys Cys Phe Ser Tyr Thr Ser Arg Gln Ile Pro Gln Asn Phe Ile Ala
         35                  40                  45

Asp Tyr Phe Glu Thr Ser Ser Gln Cys Ser Lys Pro Gly Val Ile Phe
 50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                 85                  90
```

<210> SEQ ID NO 20
<211> LENGTH: 92
<212> TYPE: PRT
<213> ORGANISM: Homo sapiens

<400> SEQUENCE: 20

```
Met Lys Leu Cys Val Thr Val Leu Ser Leu Leu Met Leu Val Ala Ala
 1               5                  10                  15
```

```
                 1               5                  10                 15
Phe Cys Ser Pro Ala Leu Ser Ala Pro Met Gly Ser Asp Pro Pro Thr
                20                 25                 30

Ala Cys Cys Phe Ser Tyr Thr Ala Arg Lys Leu Pro Arg Asn Phe Val
                35                 40                 45

Val Asp Tyr Tyr Glu Thr Ser Ser Leu Cys Ser Gln Pro Ala Val Val
 50                 55                 60

Phe Gln Thr Lys Arg Ser Lys Gln Val Cys Ala Asp Pro Ser Glu Ser
 65                 70                 75                 80

Trp Val Gln Glu Tyr Val Tyr Asp Leu Glu Leu Asn
                85                 90

<210> SEQ ID NO 21
<211> LENGTH: 91
<212> TYPE: PRT
<213> ORGANISM: Homo sapiens

<400> SEQUENCE: 21

Met Lys Val Ser Ala Ala Arg Leu Ala Val Ile Leu Ile Ala Thr Ala
 1               5                  10                 15

Leu Cys Ala Pro Ala Ser Ala Ser Pro Tyr Ser Ser Asp Thr Thr Pro
                20                 25                 30

Cys Cys Phe Ala Tyr Ile Ala Arg Pro Leu Pro Arg Ala His Ile Lys
                35                 40                 45

Glu Tyr Phe Tyr Thr Ser Gly Lys Cys Ser Asn Pro Ala Val Val Phe
 50                 55                 60

Val Thr Arg Lys Asn Arg Gln Val Cys Ala Asn Pro Glu Lys Lys Trp
 65                 70                 75                 80

Val Arg Glu Tyr Ile Asn Ser Leu Glu Met Ser
                85                 90

<210> SEQ ID NO 22
<211> LENGTH: 89
<212> TYPE: PRT
<213> ORGANISM: Homo sapiens

<400> SEQUENCE: 22

Met Asn Ala Lys Val Val Val Val Leu Val Leu Val Leu Thr Ala Leu
 1               5                  10                 15

Cys Leu Ser Asp Gly Lys Pro Val Ser Leu Ser Tyr Arg Cys Pro Cys
                20                 25                 30

Arg Phe Phe Glu Ser His Val Ala Arg Ala Asn Val Lys His Leu Lys
                35                 40                 45

Ile Leu Asn Thr Pro Asn Cys Ala Leu Gln Ile Val Ala Arg Leu Lys
 50                 55                 60

Asn Asn Asn Arg Gln Val Cys Ile Asp Pro Lys Leu Lys Trp Ile Gln
 65                 70                 75                 80

Glu Tyr Leu Glu Lys Ala Leu Asn Lys
                85

<210> SEQ ID NO 23
<211> LENGTH: 99
<212> TYPE: PRT
<213> ORGANISM: Homo sapiens

<400> SEQUENCE: 23

Met Thr Ser Lys Leu Ala Val Ala Leu Leu Ala Ala Phe Leu Ile Ser
 1               5                  10                 15
```

```
Ala Ala Leu Cys Glu Gly Ala Val Leu Pro Arg Ser Ala Lys Glu Leu
         20                  25                  30

Arg Cys Gln Cys Ile Lys Thr Tyr Ser Lys Pro Phe His Pro Lys Phe
         35                  40                  45

Ile Lys Glu Leu Arg Val Ile Glu Ser Gly Pro His Cys Ala Asn Thr
     50                  55                  60

Glu Ile Ile Val Lys Leu Ser Asp Gly Arg Glu Leu Cys Leu Asp Pro
 65                  70                  75                  80

Lys Glu Asn Trp Val Gln Arg Val Val Glu Lys Phe Leu Lys Arg Ala
                 85                  90                  95

Glu Asn Ser

<210> SEQ ID NO 24
<211> LENGTH: 107
<212> TYPE: PRT
<213> ORGANISM: Homo sapiens

<400> SEQUENCE: 24

Met Ala Arg Ala Ala Leu Ser Ala Ala Pro Ser Asn Pro Arg Leu Leu
 1               5                  10                  15

Arg Val Ala Leu Leu Leu Leu Leu Val Ala Ala Gly Arg Arg Ala
         20                  25                  30

Ala Gly Ala Ser Val Ala Thr Glu Leu Arg Cys Gln Cys Leu Gln Thr
         35                  40                  45

Leu Gln Gly Ile His Pro Lys Asn Ile Gln Ser Val Asn Val Lys Ser
     50                  55                  60

Pro Gly Pro His Cys Ala Gln Thr Glu Val Ile Ala Thr Leu Lys Asn
 65                  70                  75                  80

Gly Arg Lys Ala Cys Leu Asn Pro Ala Ser Pro Ile Val Lys Lys Ile
                 85                  90                  95

Ile Glu Lys Met Leu Asn Ser Asp Lys Ser Asn
                100                 105

<210> SEQ ID NO 25
<211> LENGTH: 97
<212> TYPE: PRT
<213> ORGANISM: Homo sapiens

<400> SEQUENCE: 25

Met Lys Val Ser Ala Ala Leu Leu Trp Leu Leu Leu Ile Ala Ala Ala
 1               5                  10                  15

Phe Ser Pro Gln Gly Leu Ala Gly Pro Ala Ser Val Pro Thr Thr Cys
         20                  25                  30

Cys Phe Asn Leu Ala Asn Arg Lys Ile Pro Leu Gln Arg Leu Glu Ser
         35                  40                  45

Tyr Arg Arg Ile Thr Ser Gly Lys Cys Pro Gln Lys Ala Val Ile Phe
     50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                 85                  90                  95

Pro

<210> SEQ ID NO 26
<211> LENGTH: 148
<212> TYPE: PRT
```

<213> ORGANISM: Mus musculus

<400> SEQUENCE: 26

```
Met Gln Val Pro Val Met Leu Leu Gly Leu Leu Phe Thr Val Ala Gly
  1               5                  10                  15

Trp Ser Ile His Val Leu Ala Gln Pro Asp Ala Val Asn Ala Pro Leu
             20                  25                  30

Thr Cys Cys Tyr Ser Phe Thr Ser Lys Met Ile Pro Met Ser Arg Leu
         35                  40                  45

Glu Ser Tyr Lys Arg Ile Thr Ser Ser Arg Cys Pro Lys Glu Ala Val
 50                  55                  60

Val Phe Val Thr Lys Leu Lys Arg Glu Val Cys Ala Asp Pro Lys Lys
 65                  70                  75                  80

Glu Trp Val Gln Thr Tyr Ile Lys Asn Leu Asp Arg Asn Gln Met Arg
                 85                  90                  95

Ser Glu Pro Thr Thr Leu Phe Lys Thr Ala Ser Ala Leu Arg Ser Ser
            100                 105                 110

Ala Pro Leu Asn Val Lys Leu Thr Arg Lys Ser Glu Ala Asn Ala Ser
        115                 120                 125

Thr Thr Phe Ser Thr Thr Thr Ser Ser Thr Ser Val Gly Val Thr Ser
130                 135                 140

Val Thr Val Asn
145
```

<210> SEQ ID NO 27
<211> LENGTH: 10
<212> TYPE: PRT
<213> ORGANISM: Homo sapiens

<400> SEQUENCE: 27

```
Cys Leu Asp Pro Lys Lys Glu Trp Ile Gln
  1               5                  10
```

<210> SEQ ID NO 28
<211> LENGTH: 825
<212> TYPE: DNA
<213> ORGANISM: Homo sapiens
<220> FEATURE:
<221> NAME/KEY: CDS
<222> LOCATION: (34)...(327)

<400> SEQUENCE: 28

```
acattgtgaa atctccaact cttaaccttc aac atg aaa gtc tct gca gtg ctt        54
                                    Met Lys Val Ser Ala Val Leu
                                      1               5 ctg tgc ctg ctg ctc atg aca gca gct ttc aac ccc cag gga ctt gct       102
Leu Cys Leu Leu Leu Met Thr Ala Ala Phe Asn Pro Gln Gly Leu Ala
            10                  15                  20 cag cca gat gca ctc aac gtc cca tct act tgc tgc ttc aca ttt agc       150
Gln Pro Asp Ala Leu Asn Val Pro Ser Thr Cys Cys Phe Thr Phe Ser
     25                  30                  35 agt aag aag atc tcc ttg cag agg ctg aag agc tat gtg atc acc acc       198
Ser Lys Lys Ile Ser Leu Gln Arg Leu Lys Ser Tyr Val Ile Thr Thr
 40                  45                  50                  55 agc agg tgt ccc cag aag gct gtc atc ttc aga acc aaa ctg ggc aag       246
Ser Arg Cys Pro Gln Lys Ala Val Ile Phe Arg Thr Lys Leu Gly Lys
                 60                  65                  70 gag atc tgt gct gac cca aag gag aag tgg gtc cag aat tat atg aaa       294
Glu Ile Cys Ala Asp Pro Lys Glu Lys Trp Val Gln Asn Tyr Met Lys
             75                  80                  85
```

| | | |
|---|---|---|
| cac ctg ggc cgg aaa gct cac acc ctg aag act tgaactctgc taccccact | | 347 |
| His Leu Gly Arg Lys Ala His Thr Leu Lys Thr | | |
| 90 95 | | | gaaatcaagc tggagtacgt gaaatgactt ttccattctc ctctggcctc ctcttctatg  407 ctttggaata cttctaccat aattttcaaa taggatgcat tcggttttgt gattcaaaat  467 gtactatgtg ttaagtaata ttggctatta tttgacttgt tgctggtttg gagtttattt  527 gagtattgct gatcttttct aaagcaaggc cttgagcaag taggttgctg tctctaagcc  587 cccttccctt ccactatgag ctgctggcag tgggttgtat tcggttccca ggggttgaga  647 gcatgcctgt gggagtcatg gacatgaagg gatgctgcaa tgtaggaagg agagctcttt  707 gtgaatgtga ggttgttgct aaattattgt ttattgtgga aagatgaatg caatagtagg  767 actgctgaca ttttgcagaa aatacatttt atttaaaatc tcctaaaaaa aaaaaaaa   825

<210> SEQ ID NO 29
<211> LENGTH: 3524
<212> TYPE: DNA
<213> ORGANISM: Homo sapiens
<220> FEATURE:
<221> NAME/KEY: CDS
<222> LOCATION: (80)...(358)

<400> SEQUENCE: 29
tctccgtcag ccgcattgcc cgctcggcgt ccggcccccg accgtgctc gtccgcccgc  60

| | | |
|---|---|---|
| ccgcccgccc gcccgcgcc atg aac gcc aag gtc gtg gtc gtg ctg gtc ctc | | 112 |
| Met Asn Ala Lys Val Val Val Val Leu Val Leu | | |
| 1 5 10 | | |
| gtg ctg acc gcg ctc tgc ctc agc gac ggg aag ccc gtc agc ctg agc | | 160 |
| Val Leu Thr Ala Leu Cys Leu Ser Asp Gly Lys Pro Val Ser Leu Ser | | |
| 15 20 25 | | |
| tac aga tgc cca tgc cga ttc ttc gaa agc cat gtt gcc aga gcc aac | | 208 |
| Tyr Arg Cys Pro Cys Arg Phe Phe Glu Ser His Val Ala Arg Ala Asn | | |
| 30 35 40 | | |
| gtc aag cat ctc aaa att ctc aac act cca aac tgt gcc ctt cag att | | 256 |
| Val Lys His Leu Lys Ile Leu Asn Thr Pro Asn Cys Ala Leu Gln Ile | | |
| 45 50 55 | | |
| gta gcc cgg ctg aag aac aac aac aga caa gtg tgc att gac ccg aag | | 304 |
| Val Ala Arg Leu Lys Asn Asn Asn Arg Gln Val Cys Ile Asp Pro Lys | | |
| 60 65 70 75 | | |
| cta aag tgg att cag gag tac ctg gag aaa gct tta aac aag agg ttc | | 352 |
| Leu Lys Trp Ile Gln Glu Tyr Leu Glu Lys Ala Leu Asn Lys Arg Phe | | |
| 80 85 90 | | |
| aag atg tgagagggtc agacgcctga ggaacccta cagtaggagc ccagctctga | | 408 |
| Lys Met | | | aaccagtgtt agggaagggc ctgccacagc ctccctgcc agggcaggc cccaggcatt  468 gccaagggct ttgttttgca cactttgcca tattttcacc atttgattat gtagcaaaat  528 acatgacatt tatttttcat ttagtttgat tattcagtgt cactggcgac acgtagcagc  588 ttagactaag gccattattg tacttgcctt attagagtgt cttccacgg agccactcct  648 ctgactcagg gctcctgggt tttgtattct ctgagctgtg caggtgggga gactgggctg  708 agggagcctg gccccatggt cagccctagg gtggagagcc accagaggg acgcctgggg  768 gtgccaggac cagtcaacct gggcaaagcc tagtgaaggc ttctctctgt gggatgggat  828 ggtggagggc cacatgggag gctcacccc ttctccatcc acatgggagc cgggtctgcc  888 tcttctggga gggcagcagg gctaccctga gctgaggcag cagtgtgagg ccagggcaga  948

-continued

```
gtgagaccca gccctcatcc cgagcacctc cacatcctcc acgttctgct catcattctc    1008
tgtctcatcc atcatcatgt gtgtccacga ctgtctccat ggccccgcaa aaggactctc    1068
aggaccaaag ctttcatgta aactgtgcac caagcaggaa atgaaaatgt cttgtgttac    1128
ctgaaaacac tgtgcacatc tgtgtcttgt gtggaatatt gtccattgtc caatcctatg    1188
tttttgttca aagccagcgt cctcctctgt gaccaatgtc ttgatgcatg cactgttccc    1248
cctgtgcagc cgctgagcga ggagatgctc cttgggccct tgagtgcag tcctgatcag     1308 agccgtggtc ctttggggtg aactaccttg gttcccccac tgatcacaaa aacatggtgg    1368
gtccatgggc agagcccaag ggaattcggt gtgcaccagg gttgacccca gaggattgct    1428
gccccatcag tgctccctca catgtcagta ccttcaaact agggccaagc ccagcactgc    1488
ttgaggaaaa caagcattca caacttgttt ttggtttta aaacccagtc cacaaaataa     1548
ccaatcctgg acatgaagat tctttcccaa ttcacatcta acctcatctt cttcaccatt    1608
tggcaatgcc atcatctcct gccttcctcc tgggccctct ctgctctgcg tgtcacctgt    1668
gcttcgggcc cttcccacag gacatttctc taagagaaca atgtgctatg tgaagagtaa    1728
gtcaacctgc ctgacatttg gagtgttccc ctcccactga gggcagtcga tagagctgta    1788
ttaagccact taaaatgttc acttttgaca aaggcaagca cttgtgggtt tttgttttgt    1848
ttttcattca gtcttacgaa tacttttgcc ctttgattaa agactccagt taaaaaaaat    1908
tttaatgaag aaagtggaaa acaaggaagt caaagcaagg aaactatgta acatgtagga    1968
agtaggaagt aaattatagt gatgtaatct tgaattgtaa ctgttcgtga atttaataat    2028
ctgtagggta attagtaaca tgtgttaagt attttcataa gtatttcaaa ttggagcttc    2088
atggcagaag gcaaacccat caacaaaaat tgtcccttaa acaaaaatta aaatcctcaa    2148
tccagctatg ttatattgaa aaaatagagc ctgagggatc tttactagtt ataaagatac    2208
agaactcttt caaaaccttt tgaaattaac ctctcactat accagtataa ttgagttttc    2268 agtgggcag tcattatcca ggtaatccaa gatatttaa aatctgtcac gtagaacttg      2328
gatgtacctg cccccaatcc atgaaccaag accattgaat tcttggttga ggaaacaaac    2388
atgaccctaa atcttgacta cagtcaggaa aggaatcatt tctatttctc ctccatggga    2448
gaaaatagat aagagtagaa actgcaggga aaattatttg cataacaatt cctctactaa    2508
caatcagctc cttcctggag actgcccagc taaagcaata tgcatttaaa tacagtcttc    2568
catttgcaag ggaaaagtct cttgtaatcc gaatctcttt ttgctttcga actgctagtc    2628
aagtgcgtcc acgagctgtt tactagggat ccctcatctg tccctccggg acctggtgct    2688
gcctctacct gacactccct tgggctccct gtaacctctt cagaggccct cgctgccagc    2748
tctgtatcag gacccagagg aagggccag aggctcgttg actggctgtg tgttgggatt     2808
gagtctgtgc cacgtgtatg tgctgtggtg tgtcccctc tgtccaggca ctgagatacc     2868
agcgaggagg ctccagaggg cactctgctt gttattagag attacctcct gagaaaaaag    2928
cttccgcttg gagcagaggg gctgaatagc agaaggttgc acctccccca accttagatg    2988
ttctaagtct ttccattgga tctcattgga cccttccatg gtgtgatcgt ctgactggtg    3048
ttatcaccgt gggctccctg actgggagtt gatcgccttt cccaggtgct acacccttt     3108 ccagctggat gagaatttga gtgctctgat ccctctacag agcttccctg actcattctg    3168
aaggagcccc attcctggga atattccct agaaacttcc aaatcccta agcagaccac      3228 tgataaaacc atgtagaaaa tttgttattt tgcaacctcg ctggactctc agtctctgag    3288
cagtgaatga ttcagtgtta aatgtgatga atactgtatt ttgtattgtt tcaagtgcat    3348
```

```
ctcccagata atgtgaaaat ggtccaggag aaggccaatt cctatacgca gcgtgcttta    3408
aaaaataaat aagaaacaac tctttgagaa acaacaattt ctactttgaa gtcataccaa    3468
tgaaaaaatg tatatgcact tataattttc ctaataaagt tctgtactca aatgta        3524

<210> SEQ ID NO 30
<211> LENGTH: 4259
<212> TYPE: DNA
<213> ORGANISM: Mus musculus
<220> FEATURE:
<221> NAME/KEY: CDS
<222> LOCATION: (2070)...(2130)
<220> FEATURE:
<221> NAME/KEY: CDS
<222> LOCATION: (2669)...(2795)
<220> FEATURE:
<221> NAME/KEY: CDS
<222> LOCATION: (2990)...(3079)
<220> FEATURE:
<221> NAME/KEY: CDS
<222> LOCATION: (3491)...(3506)

<400> SEQUENCE: 30
gaattcggag gtctacctgc ctctgcctcc caagtactgg aattactctt acggcttact      60
tttcctcaag ggtcttcaaa gcacttctga ccatagggag cggactctta ggaaattcca    120
tatagattct tttatttcag tcatttgaca ttaactttat agtcataaat tttgatattt    180
ttttacagat ctgaatatgt ttgaagaaat gttcattttt ccctagcca caaaaatccc    240 atgacatgta taccatactt gccataacct gctataattc agtgcaaaat ggcctgttct    300
agtcaaaggg ctgctttcaa gtacgagtga ctatttactg gatacaatgt atgtatacta    360
cagtaacttt cattttagca tgaaattctg tgtaaaacaa gtccaattta acccccttct    420
aggtgtttag ttccagaaac accaagaaa catcaaagat aacttcagcc aagcagacac      480
aggcaagtct ggagcctgaa ccaaggatct gctctttgga gacactgcat aaccaagtgt    540
ttgagagcgt gggctacaga gatggagttt ctggattcct agagggttga atgagggaaa    600
actcttgact aacagatgct taacactacg caatagttac taaactcttt tctcctcagt    660
aagggactat atatccactt gctaactgtt ttttcttaac atcctcaaat ctgtttttcc    720
ttcacatctt gactgagaac ttgtacaata acaaaataaa ataaaactgt caccatgtat    780
ctttctttat tgtttaatgt aaaactgctc agcacctctt tccactctaa aattctgagg    840
ttcctacagc gcagcgtcta ttctgcagaa gcaggttggg agagactgct catggcgtcc    900
tctcacagta gccttctccc agcagaaggt tgcaaaacga aagtctcttg gcttgtctct    960
gcccccattc ccttctgtct gtccttccag attccacggc tgtcccgtga tttgctccct   1020
tgaaagctta gctctgttct agtccttgga ctacatcaat gtggattttg ctctctagaa   1080
atttctatct ttcccaagca gcaactccct tcctgttctg gtgacagctc ctgtttccca   1140
gttcccattg gtgggtagag gtttcactct tggcctctgt tgtcaagttt tgaaccggta   1200
cactccaggc tcctgtccca ttcccaggat gagtcacctc catcccctc atcactgtca    1260 cctctatgcg agatctatgt aacctcacct actcttccag gtcccaggta tctgctgcct    1320
tgggtgctct gcagagtgac atccacattc actttcatcc ttgaccctgt taccacacac   1380
tcacaaagaa gacaatcaaa gcatccctga gagaatcagc acgggcaac aattagcttt     1440 gcaattcctc ttgtaacttg taaacattag tgtgacactt ccggcttctg ttctgaatgc   1500
ctgctctaac tgttcactaa gttgtataga ctttggatct ggctaaattt ggcatgtgat   1560
```

```
                                                       -continued
tttttttta  aagtttattc  caagtatttt  ataataaagc  ctatgaagta  aaaagcaaaa    1620
ataaacagtg  taaacacaac  aaatgtaaaa  accatggtta  gaacctgact  tagatatcag    1680
ctctgtgttt  tatttatgag  agaaggaaga  tgagaattaa  agccatttcc  agacttattc    1740
tgcaaggcac  tcatctgatt  tctcaaacag  ctcacgcttt  ggaaagtgaa  acctacctca    1800
ctcgttaaaa  attaaaagga  gcacaagagg  ggagagggaa  attccaagtt  catgggtcac    1860
aataaacaca  agcaatgccc  tcggtttaca  ggggacttcc  ctcggttgc   ggagccttgc    1920 tgagtcatct  ccaaagtcag  ccaatcagga  ctcagggagg  gaaactcttt  gcagataaat    1980
actcctcagc  agccggcact  cgagaagcgc  ttcatccacc  gctgagagac  atcccgagcc    2040
aaccttccgg  aagcctcccc  atcagcacc  atg aac cca agt gct gcc gtc att         2093
                                   Met Asn Pro Ser Ala Ala Val Ile
                                     1               5 ttc tgc ctc atc ctg ctg ggt ctg agt ggg act caa g gtaagggaca              2140
Phe Cys Leu Ile Leu Leu Gly Leu Ser Gly Thr Gln
    10              15                  20 ccaaggccat  ttaattaacg  aagtcagaag  tcagacgatt  aagctcagtt  ctaaacacag    2200
catgtattta  agctttaatg  tgtgtaccta  taaagaagag  ggaagcagga  agaaatccct    2260
tcagcttgca  gagtttatca  taggctggtt  gaagtcagag  aaaaatagaa  taaaagaaaa    2320
ggaacgaaga  agggaagaaa  gggagaaaag  gaggagggag  gaggaagaag  gagggaagag    2380
agagtcagga  gaaagggcga  aagagtggga  tggggtaagg  catggatgcc  tccttgcctg    2440
agcctaacca  atactgtgag  cagtgcataa  atgcaggatt  tcgtaactga  caagttgcag    2500
atctctcttt  accatgacca  agatattcaa  acactcagcc  ctatgatacg  atgggatgcg    2560
tctctccaca  gatcagacag  ggtctgctaa  acactacctc  atccatttta  agtgcctaaa    2620
atgaaaccgt  gtgctgacct  tcctggctct  cccctctct  tcctgcag gg atc cct        2676
                                                        Gly Ile Pro ctc gca agg acg gtc cgc tgc aac tgc atc cat atc gat gac ggg cca          2724
Leu Ala Arg Thr Val Arg Cys Asn Cys Ile His Ile Asp Asp Gly Pro
    25                  30                  35 gtg aga atg agg gcc ata ggg aag ctt gaa atc atc cct gcg agc cta          2772
Val Arg Met Arg Ala Ile Gly Lys Leu Glu Ile Ile Pro Ala Ser Leu
40                  45                  50                  55 tcc tgc cca cgt gtt gag atc at gtgagtacaa gcccacctgc cgataaacgt          2825
Ser Cys Pro Arg Val Glu Ile Ile
                60 ccctcccgta  accacacagt  aaataagtga  gggaaaccag  gaaagatggg  gacgggtctg    2885 tgactctaac  taaggcacag  tgcctgaact  ctgacatgga  cctgcagggc  catcagctct    2945 gttggcctga  cgttaatctg  agtatctcac  tcttatttct  atag t gcc acg atg        2999
                                                  Ala Thr Met
                                                     65 aaa aag aat gat gag cag aga tgt ctg aat ccg gaa tct aag acc atc          3047
Lys Lys Asn Asp Glu Gln Arg Cys Leu Asn Pro Glu Ser Lys Thr Ile
        70                  75                  80 aag aat tta atg aaa gcg ttt agc caa aaa ag gtaggtttga tgttgctttt         3099
Lys Asn Leu Met Lys Ala Phe Ser Gln Lys Arg
        85                  90 tcaggaaatg  gtggtctggg  gagcagcgcc  tgccctgggc  tttgctgtgg  gcatctgccc    3159
taaactcatg  gcaccggcat  gtgcctttgt  ctctccattt  acacagacac  tgaggtgcct    3219
tcttaggtca  tacattccta  gtgtctagaa  gtggagcagt  tattatacct  gtcacgggta    3279
aagctgccaa  atgcccaccc  ccccacttcc  tcacttaaaa  aaaaaaaacc  aaaaacaaac    3339
```

-continued

```
aaacccattc tgtccctca acccccaccc acccgtgacc catggagatt gtgtagcaga       3399
ggaaaatgca ccaggcctt tgccccaggg tctttgggtt ccaaagtgaa agcagagtct      3459
atccgctcaa tacagtttcc tcttcctaca g g tct aaa agg gct cct              3506
                                   Ser Lys Arg Ala Pro
                                            95 taactggaga gaagccacgc acacaccccg gtgctgtgat ggacagcaga gagcctgtct     3566 ctccatcact cccctttacc cagtggatgg ctagtcctaa ttgcccttgg tcttctgaaa     3626 ggtgaccagc cgtggtcaca tcagctgcta ctcctcctgc aggatgatgg ttaagccatg    3686 gtcctgagac aaaagtaact gccgaagcaa gaattcttta agggctggtc tgagtcctca    3746 ctcaagtggc tgggatggct gtcctagctc tgtactgtaa gctatgtgga ggtgcgacgc    3806 ccttcaccat gtgccacgcc ccaggctgct ccccacaccc tccttgtcct ccctagctca    3866 ggctcgtcag ttctgagttt acctgagctc ttttatttca gatgtaagac tacaaattta    3926 agtttgtaag gacaaactta accaccatct tcccaagggg ttatcaagat actcagagga    3986 acctggaaat gtatgtgtaa atactattta atgaacgact gtacaaagta gaattcctag    4046 atgtattttt tgtatgcttt gcattgtata tggaagaact tgtgtcatca agtatgtatc    4106 aatgggtagt taaagtttat ttttaaaacc gtccaatacc ttttgtatta tgtaacattc    4166 aaaagacaat gtactgtatt gaaagtagta agagacccaa aatgtaataa agtaataata    4226 actgacatga aatggtcatg tgactgagaa ttc                                  4259

<210> SEQ ID NO 31
<211> LENGTH: 1081
<212> TYPE: DNA
<213> ORGANISM: Homo sapiens
<220> FEATURE:
<221> NAME/KEY: CDS
<222> LOCATION: (43)...(363)

<400> SEQUENCE: 31
ctctcctcct cgcacagccg ctcgaaccgc ctgctgagcc cc atg gcc cgc gcc         54
                                              Met Ala Arg Ala
                                                1 acg ctc tcc gcc gcc ccc agc aat ccc cgg ctc ctg cgg gtg gcg ctg      102
Thr Leu Ser Ala Ala Pro Ser Asn Pro Arg Leu Leu Arg Val Ala Leu
  5                  10                  15                  20 ctg ctc ctg ctc ctg gtg gcc gcc agc cgg cgc gca gca gga gcg ccc      150
Leu Leu Leu Leu Leu Val Ala Ala Ser Arg Arg Ala Ala Gly Ala Pro
             25                  30                  35 ctg gcc act gaa ctg cgc tgc cag tgc ttg cag acc ctg cag gga att      198
Leu Ala Thr Glu Leu Arg Cys Gln Cys Leu Gln Thr Leu Gln Gly Ile
         40                  45                  50 cac ctc aag aac atc caa agt gtg aag gtg aag tcc ccc gga ccc cac      246
His Leu Lys Asn Ile Gln Ser Val Lys Val Lys Ser Pro Gly Pro His
     55                  60                  65 tgc gcc caa acc gaa gtc ata gcc aca ctc aag aat ggg cag aaa gct      294
Cys Ala Gln Thr Glu Val Ile Ala Thr Leu Lys Asn Gly Gln Lys Ala
 70                  75                  80 tgt ctc aac ccc gca tcg ccc atg gtt aag aaa atc atc gaa aag atg      342
Cys Leu Asn Pro Ala Ser Pro Met Val Lys Lys Ile Ile Glu Lys Met
 85                  90                  95                 100 ctg aaa aat ggc aaa tcc aac tgaccagaag gaaggaggaa gcttattggt          393
Leu Lys Asn Gly Lys Ser Asn
             105 ggctgttcct gaaggaggcc ctgcccttac aggaacagaa gaggaaagag agacacagct    453
```

| | | |
|---|---|---|
| gcagaggcca cctggattgc gcctaatgtg tttgagcatc acttaggaga agtcttctat | | 513 |
| ttatttattt atttatttat ttgtttgttt tagaagattc tatgttaata ttttatgtgt | | 573 |
| aaaataaggt tatgattgaa tctacttgca cactctccca ttatatttat tgtttatttt | | 633 |
| aggtcaaacc caagttagtt caatcctgat tcatatttaa tttgaagata gaaggtttgc | | 693 |
| agatattctc tagtcatttg ttaatatttc ttcgtgatga catatcacat gtcagccact | | 753 |
| gtgatagagg ctgaggaatc caagaaaatg ccagtgaga tcaatgtgac ggcagggaaa | | 813 |
| tgtatgtgtg tctattttgt aactgtaaag atgaatgtca gttgttattt attgaaatga | | 873 |
| tttcacagtg tgtggtcaac atttctcatg ttgaagcttt aagaactaaa atgttctaaa | | 933 |
| tatcccttgg acattttatg tctttcttgt aaggcatact gccttgttta atgttaatta | | 993 |
| tgcagtgttt ccctctgtgt tagagcagag aggtttcgat atttattgat gttttcacaa | | 1053 |
| agaacaggaa aataaaatat ttaaaaat | | 1081 |

<210> SEQ ID NO 32
<211> LENGTH: 1173
<212> TYPE: DNA
<213> ORGANISM: Homo sapiens
<220> FEATURE:
<221> NAME/KEY: CDS
<222> LOCATION: (107)...(448)

<400> SEQUENCE: 32

```
cggcacgagc acagtgctcc ggatcctcca atcttcgctc ctccaatctc cgctcctcca      60
cccagttcag gaacccgcga ccgctcgcag cgctctcttg accact atg agc ctc        115
                                                    Met Ser Leu
                                                     1 ctg tcc agc cgc gcg gcc cgt gtc ccc ggt cct tcg agc tcc ttg tgc      163
Leu Ser Ser Arg Ala Ala Arg Val Pro Gly Pro Ser Ser Ser Leu Cys
  5                  10                  15 gcg ctg ttg gtg ctg ctg ctg ctg acg cag cca ggg ccc atc gcc          211
Ala Leu Leu Val Leu Leu Leu Leu Thr Gln Pro Gly Pro Ile Ala
 20                  25                  30                  35 agc gct ggt cct gcc gct gct gtg ttg aga gag ctg cgt tgc gtt tgt      259
Ser Ala Gly Pro Ala Ala Ala Val Leu Arg Glu Leu Arg Cys Val Cys
                 40                  45                  50 tta cag acc acg cag gga gtt cat ccc aaa atg atc agt aat ctg caa      307
Leu Gln Thr Thr Gln Gly Val His Pro Lys Met Ile Ser Asn Leu Gln
             55                  60                  65 gtg ttc gcc ata ggc cca cag tgc tcc aag gtg gaa gtg gta gcc tcc      355
Val Phe Ala Ile Gly Pro Gln Cys Ser Lys Val Glu Val Val Ala Ser
         70                  75                  80 ctg aag aac ggg aag gaa att tgt ctt gat cca gaa gcc cct ttt cta      403
Leu Lys Asn Gly Lys Glu Ile Cys Leu Asp Pro Glu Ala Pro Phe Leu
     85                  90                  95 aag aaa gtc atc cag aaa att ttg gac ggt gga aac aag gaa aac          448
Lys Lys Val Ile Gln Lys Ile Leu Asp Gly Gly Asn Lys Glu Asn
100                 105                 110 tgattaagag aaatgagcac gcatggaaaa gtttcccagt ctacagcaga gaagttttct    508
ggaggtctct gaacccaggg aagacaagaa ggaaagattt tgttgttgtt tgtttatttg    568
gtttccccag tagttagctt tcttccctgg attcctcact tttgaagagt gtgaggaaaa    628
cctatgtttg gcgcttaagc tttcagctca gcttaatgaa gtgtttagca tagtacctct    688
gctatttgct gttattttat ctgctatgct attgaagttt tggcaattga ctatagtgtg    748
agccaggaat cactggctgt taatcttaca aagtgtcttg gaattgtagg tgactattat    808
```

```
ttttccaaga aatatccctt aagatattaa ctgagaaggc tgggggttta atgtggaaat      868
gatgtttcaa aaggaatcct gtgatggaaa tacaactggt atcttcactt ttttaggaat      928
tgggaaatat tttaatgttt cttggggaat atgttagaga attcccttac tcttgattgt      988
gggatactat ttaattattt cactttagaa agctgagtgt ttcacacctt atctatgtag     1048
aatatatttc cttattcaga atttctaaaa gtttaagttc tatgagggct aatatcttat     1108
cttcctataa ttttagacat tgctttaact ttttagtaaa aaaaaaaaa aaaaaaaaa       1168 aaaaa                                                                 1173

<210> SEQ ID NO 33
<211> LENGTH: 825
<212> TYPE: DNA
<213> ORGANISM: Homo sapiens
<220> FEATURE:
<221> NAME/KEY: CDS
<222> LOCATION: (34)...(327)

<400> SEQUENCE: 33
acattgtgaa atctccaact cttaaccttc aac atg aaa gtc tct gca gtg ctt        54
                                     Met Lys Val Ser Ala Val Leu
                                       1               5 ctg tgc ctg ctg ctc atg aca gca gct ttc aac ccc cag gga ctt gct       102
Leu Cys Leu Leu Leu Met Thr Ala Ala Phe Asn Pro Gln Gly Leu Ala
         10                  15                  20 cag cca gat gca ctc aac gtc cca tct act tgc tgc ttc aca ttt agc       150
Gln Pro Asp Ala Leu Asn Val Pro Ser Thr Cys Cys Phe Thr Phe Ser
     25                  30                  35 agt aag aag atc tcc ttg cag agg ctg aag agc tat gtg atc acc acc       198
Ser Lys Lys Ile Ser Leu Gln Arg Leu Lys Ser Tyr Val Ile Thr Thr
 40                  45                  50                  55 agc agg tgt ccc cag aag gct gtc atc ttc aga acc aaa ctg ggc aag       246
Ser Arg Cys Pro Gln Lys Ala Val Ile Phe Arg Thr Lys Leu Gly Lys
                 60                  65                  70 gag atc tgt gct gac cca aag gag aag tgg gtc cag aat tat atg aaa       294
Glu Ile Cys Ala Asp Pro Lys Glu Lys Trp Val Gln Asn Tyr Met Lys
             75                  80                  85 cac ctg ggc cgg aaa gct cac acc ctg aag act tgaactctgc tacccctact    347
His Leu Gly Arg Lys Ala His Thr Leu Lys Thr
         90                  95 gaaatcaagc tggagtacgt gaaatgactt tccattctc ctctggcctc ctcttctatg      407
ctttggaata cttctaccat aattttcaaa taggatgcat tcggttttgt gattcaaaat     467
gtactatgtg ttaagtaata ttggctatta tttgacttgt tgctggtttg gagtttattt     527
gagtattgct gatcttttct aaagcaaggc cttgagcaag taggttgctg tctctaagcc     587
cccttccctt ccactatgag ctgctggcag tgggttgtat tcggttccca ggggttgaga     647
gcatgcctgt gggagtcatg gacatgaagg gatgctgcaa tgtaggaagg agagctcttt     707
gtgaatgtga ggttgttgct aaattattgt ttattgtgga aagatgaatg caatagtagg     767
actgctgaca ttttgcagaa aatacatttt atttaaaatc tcctaaaaaa aaaaaaaa      825

<210> SEQ ID NO 34
<211> LENGTH: 3112
<212> TYPE: DNA
<213> ORGANISM: Homo sapiens
<220> FEATURE:
<221> NAME/KEY: CDS
<222> LOCATION: (1192)...(1267)
<220> FEATURE:
<221> NAME/KEY: CDS
```

```
<222> LOCATION: (1953)...(2067)
<220> FEATURE:
<221> NAME/KEY: CDS
<222> LOCATION: (2488)...(2575)

<400> SEQUENCE: 34
ttagagactt aataataaag gatcttgtgg ataatttatc attccctgat agagaaaaat      60
ttagctttgc ttatttaga gttataaatg atgctgggtc aggtatcttt atgtttgaag     120
atggctccat atttgggttg tttccacaga actctttccc agaaatgctt tttctaggtt    180
aatggctaca catatttcta ggcacctgac atactgacac ccacctctaa agtattttta    240
tgatccacaa ctagcgttta acacagcgcc ccagtcactc cgagactaat aaatagacaa    300
atgactgaaa cgtgacctca tgctttctat tcctccagct ttcattgagt tcctttcctc    360
tgggaggact gggggttgtc tagccctcca cagcatcagc ccattgaccc tatccttgtg    420
gttatagcag ctgaggaagc agaattacag ctctgtggga aggaatgggg ctggagagtt    480
catgcataga ccaattcttt ttttttttt tttttgagat ggagtttcac ttttgttgcc     540
caggctggag tgcaatggca tgatctcagc tcaccacagc ccccacctcc tgggttcaag    600
cgattctcct gccctcagcc tcccgagtag ctgggattac aggcatgtgc caccacgcct    660 gactacttt gtatttttag tagagatgga gtttctcttt cttggtcagg ttggtctcaa     720
actcctgacc tcaggtgatc cgcagcctcg gcctcccaaa gtgttgggat tacaggtgtg    780
agcgaccatg cctggctgca tagaccagtt cttatgagaa gggatcaact aagaatagcc    840
ttgggttgac acacacccct cttcacactc acaggagaaa ccccatgaag ctagaaccag    900
tcatgagttg agagctgaga gttagagagt agctcagaga tgctattctt ggatatcctg    960
agcccctgtg gtcaccaggg accctgagtt gtgcaacact cagcatgaca gcatcactac   1020
acttaaaaat ttccctcctc accccagat tccatttccc catccgccag ggctgcctat   1080
aaagaggaga gatggcttca gacatcagaa ggacgcaggc agcaaagagt agtcagtccc   1140
ttcttggctc tgctgacact cgagcccaca ttccatcacc tgctcccaat c atg cag    1197
                                                        Met Gln
                                                         1 gtc tcc act gct gcc ctt gcc gtc ctc ctc tgc acc atg gct ctc tgc     1245
Val Ser Thr Ala Ala Leu Ala Val Leu Leu Cys Thr Met Ala Leu Cys
 5              10                  15 aac cag gtc ctc tct gca cca c gtgagtccat gttgttgttg tgggtatcac      1297
Asn Gln Val Leu Ser Ala Pro
 20              25 cactctctgg ccatggttag accacatcag tcttttttg cggcctgaga gccccgaaga   1357
gaaaagaagg aagttcttaa agcgctgcca aacaccttgg tcttttttctt cacaactttt   1417 atttttatct ctagaagggg tcttagccct cctagtctcc aggtatgaga atctaggcag   1477 gggcaggggga gttacagtcc cttgtacaga tagaaaaaca gggttcaaaa cgaatcagtt   1537
tgcaagaggc agaatccagg gctgcttact tcccagtggg gtctgttgtt cactctccag   1597
ctcaccctag gtctcccagg agccctgtcc cttggatgtc ttatgagaga tgtccagggc   1657
ttctcttggg ctggggtatg acttcttgaa ccgacaaaat tccatgaaga gagctaagag   1717
aacagtccat tcaggtatct ggatcacata gagaaacaga gaacccacta tgaagagtca   1777
aggggaaaga ggaatataga cagaaacaaa gagacatttc tctgcaaaac cccccaaatg   1837
ccttgcagtc acttggtctg agcaagcctg ccctcctcaa ccactcaggg atcagaagct   1897
gcctggcctt ttcttctgag ctgtgactcg ggcttattct ctcctttctc cgcag tt     1954
                                                               Leu
```

-continued

```
gct gct gac acg ccg acc gcc tgc tgc ttc agc tac acc tcc cga cag      2002
Ala Ala Asp Thr Pro Thr Ala Cys Cys Phe Ser Tyr Thr Ser Arg Gln
        30                  35                  40 att cca cag aat ttc ata gct gac tac ttt gag acg agc agc cag tgc      2050
Ile Pro Gln Asn Phe Ile Ala Asp Tyr Phe Glu Thr Ser Ser Gln Cys
    45                  50                  55 tcc aag ccc agt gtc at gtaagtgcca gtcttcctgc tcacctctag              2097
Ser Lys Pro Ser Val Ile
60 ggaggtaggg agtgtcaggg tgggggcaga acaggccag aaggccatcc tggaaaggcc     2157 cagccttcag gagcctatcg gggatacagg acgcagggca ctgaggtgtg acctgacttg    2217 gggctggagt gaggtgggtg ttacagagtc aggaagggct gccccaggcc agaggaaagg    2277 aacaggaaga aggaggcagc aggacactct gagggcccc ttgcctggag tcactgagag     2337 aagctctcta gacggagata ggcaggggc ccctgagaga ggagcaggcc ttgagctgcc     2397 caggacagag agcaggatgt caggccatgg tgggcccagg attccccggc tggattcccc    2457 agtgcttaac tcttcctccc ttctccacag c ttc cta acc aag aga ggc cgg       2509
                                 Phe Leu Thr Lys Arg Gly Arg
                                         65                  70 cag gtc tgt gct gac ccc agt gag gag tgg gtc cag aaa tac gtc agt      2557
Gln Val Cys Ala Asp Pro Ser Glu Glu Trp Val Gln Lys Tyr Val Ser
        75                  80                  85 gac ctg gag ctg agt gcc tgaggggtcc agaagcttcg aggcccagcg             2605
Asp Leu Glu Leu Ser Ala
            90 acctcagtgg gcccagtggg gaggagcagg agcctgagcc ttgggaacat gcgtgtgacc    2665 tctacagcta cctcttctat ggactggtta ttgccaaaca gccacactgt gggactcttc    2725 ttaacttaaa ttttaattta tttatactat ttagttttta taatttattt ttgatttcac    2785 agtgtgtttg tgattgtttg ctctgagagt tccccctgtc ccctccacct tccctcacag    2845 tgtgtctggt gacgaccgag tggctgtcat cggcctgtgt aggcagtcat ggcaccaaag    2905 ccaccagact gacaaatgtg tatcagatgc ttttgttcag ggctgtgatc ggcctgggga    2965 aataataaag atgttctttt aaacggtaaa ccagtattga gtttggtttt gtttttctgg    3025 caaatcaaaa tcactagtta agaggaatca taggcaaaga ttaggaagag gtgaaatgga    3085 gggaaactgg gagagatggg gagcgct                                        3112
```

<210> SEQ ID NO 35
<211> LENGTH: 481
<212> TYPE: DNA
<213> ORGANISM: Homo sapiens
<220> FEATURE:
<221> NAME/KEY: CDS
<222> LOCATION: (55)...(333)

<400> SEQUENCE: 35

```
agcctctgaa gctcccacca ggccagctct cctcccacaa cagcttccca cagc atg      57
                                                              Met
                                                              1 aag atc tcc gtg gct gcc att ccc ttc ttc ctc ctc atc acc atc gcc      105
Lys Ile Ser Val Ala Ala Ile Pro Phe Phe Leu Leu Ile Thr Ile Ala
    5                   10                  15 cta ggg acc aag act gaa tcc tcc tca cgg gga cct tac cac ccc tca      153
Leu Gly Thr Lys Thr Glu Ser Ser Ser Arg Gly Pro Tyr His Pro Ser
        20                  25                  30 gag tgc tgc ttc acc tac act acc tac aag atc ccg cgt cag cgg att      201
```

-continued

```
Glu Cys Cys Phe Thr Tyr Thr Thr Tyr Lys Ile Pro Arg Gln Arg Ile
     35                  40                  45 atg gat tac tat gag acc aac agc cag tgc tcc aag ccc gga att gtc    249
Met Asp Tyr Tyr Glu Thr Asn Ser Gln Cys Ser Lys Pro Gly Ile Val
 50                  55                  60                  65 ttc atc acc aaa agg ggc cat tcc gtc tgt acc aac ccc agt gac aag    297
Phe Ile Thr Lys Arg Gly His Ser Val Cys Thr Asn Pro Ser Asp Lys
             70                  75                  80 tgg gtc cag gac tat atc aag gac atg aag gag aac tgagtgaccc         343
Trp Val Gln Asp Tyr Ile Lys Asp Met Lys Glu Asn
         85                  90 agaagggtg gcgaaggcac agctcagaga cataaagaga agatgccaag gccccctcct   403
ccacccaccc ctaactctca gccccagtca ccctcttgga gcttccctgc tttgaattaa   463
agaccactca tgctcttc                                                 481
```

<210> SEQ ID NO 36
<211> LENGTH: 3709
<212> TYPE: DNA
<213> ORGANISM: Homo sapiens
<220> FEATURE:
<221> NAME/KEY: CDS
<222> LOCATION: (885)...(960)
<220> FEATURE:
<221> NAME/KEY: CDS
<222> LOCATION: (2149)...(2260)
<220> FEATURE:
<221> NAME/KEY: CDS
<222> LOCATION: (3383)...(3482)

<400> SEQUENCE: 36

```
tctagaaaaa aaaaaacaaa aagggaaaat tcccctggca ggactctcag atgctgctga    60
gtagctctca gtcctctctg taacccaaac ataacacatc tatctccgtg cttacactgg   120
gtggctttca cttgtttatc tgtgaattga agagaagttg cttgaggtca ggcagtgctc   180
ctcattggta actgccttct ctggggctaa ccaaggacct agaacagaat aagctattga   240
aaattgttga ggattgaaaa aaatagaaaa aatagaaatg gcaaatatct aggccagtca   300
ctggacatag agaatgttat ttaattctta tcgcacgtcc ttgagacatg tattgctatt   360
tgcattttgt gtgaatatgc atttgggtaa gtttatgtaa tccctcctct gcagaactgg   420
gattcaaatg caggtgtatc tctgttcagg tccagactct tctgccctga agcagtagta   480
cttggatgga atgacgtagg gttggacaag ccacacagag gccacttcct ctcacttact   540
tttctttgct tcccactcaa ccaggacagt tcccacgcac tttttcaaga ttcttatctg   600
ctcccacact tggggaagtt cccaatgcaa cctatcaatc catcaccacc acgaatacca   660
gccaggagag gtggggaaag gagtttacca catggtcgct gggtgtgagc aactgttccc   720
tgtccctatg gcttcccact gtggctcccc accatggcct ggagttttgg gtggagtttt   780
tcaaataaaa gccctcagca ttgcaggacg gcacagtggt gagctcttag cttccaccagg   840 ctcatcaaag ctgctccagg aaggcccaag ccagaccaga agac atg cag atc atc   896
                                                 Met Gln Ile Ile
                                                   1
```

```
acc aca gcc ctg gtg tgc ttg ctg cta gct ggg atg tgg ccg gaa gat   944
Thr Thr Ala Leu Val Cys Leu Leu Leu Ala Gly Met Trp Pro Glu Asp
  5                  10                  15                  20 gtg gac agc aag agc a gtgagtgtgg caggcatcat tttgcttctc tctggggagg   1000
Val Asp Ser Lys Ser
             25 gcagaaacgt ggtcagccac tctggggttg gagcaggctt ctccttgaac tcaccaactc   1060
```

-continued

```
tatctcccct cttcctacct aaagaggagg aatggtgaac ttggacaggc tggggtgagg    1120
gctagtagga gaaccatgag ttggggcaaa cacagagaac tgaactgaca gcttcagtac    1180
aaggagctct gcttcatcca gacccaagga agggaacctg tgaggttact cgggtaaagc    1240
tgggaggccc aagtccagg ggacagcctg ggtgtagctt ctacagtgtg acagacacca     1300
agtagagtca gaaggcaaga ccgggctcta acaattggtc actcttgggc aagtcacttt    1360
agctctcaaa ctctactttc tctatcagtg aaatggagtt gatgatgtct gccctccaag    1420
actgtttgga gaataccaac ctagtaagag gcatgaaagg gggtgcaaac agaaaaacta    1480
ggaggaagaa gctgggattg gaatgcaggt ctcttgcggg atgtggtgtg ggaggagaat    1540
gcacaaatgg acagagtggg ggttgggggc tgggaaagag ctaaggacca gggcaggagg    1600
ggattcaaga gactgagtag ggcagctagc tagttcctgg gagctcttcc cttgtcatct    1660
catcagtttg gactcctcga acaattccta atcttcccca gatcaggtct gtgaactgtg    1720
gaccactgtg tcctgcatca gactaaccag gtccccaggg tgtggggtcc agagcccttg    1780
gacatgaata ctggggcaga accatgcaca tgtggtgaaa taccaaaact ggatgagcct    1840
ttagaaacca ggctccaaaa agttttattt tacagatggg aagtctgggg ccagggtgaa    1900
ggcacatctt cctcagggcc actcagctgg ggtgcgggga gctcagatct gaaccccaat    1960
cttctgactc tttacctagc cccagaacaa ggtggctgat gaggcagagc tatgccggca    2020
ccgtctggat gtggtcccca agccagggct tgtcctggga ggcgtttttt tgtttgtttt    2080
ttaaaaattg tgctacaggt gagaggttga gaaatggatg caaaccatcg tctgtgttcc    2140 tcttctag tg cag gta ccc ttc tcc aga tgt tgc ttc tca ttt gcg gag     2189
         Met Gln Val Pro Phe Ser Arg Cys Cys Phe Ser Phe Ala Glu
                 30              35 caa gag att ccc ctg agg gca atc ctg tgt tac aga aat acc agc tcc     2237
Gln Glu Ile Pro Leu Arg Ala Ile Leu Cys Tyr Arg Asn Thr Ser Ser
 40              45              50              55 atc tgc tcc aat gag ggc tta at gtaagtgatc acctgctcaa tctctcccta    2290
Ile Cys Ser Asn Glu Gly Leu Ile
                 60 gagaacagaa ccccgccagc ctggaattac aagagtagac actagatgac agtatttac    2350 tggaataagg tttctaaacc cagagctgcc agcacctggg tgcaagccac acttgggcgc    2410 tagagggagc gctgagcttc ctagcaggtg tgaggaagga tgcatctgtg ctcctgcagt    2470 ggcttgtgtt tcctgaaact ccaaggtgcc aagtattgta tcccagcatt atgagctcag    2530 aggtttaaca aaagcatgag gggttattgt gcactggaaa gagcaaggga accaggatga    2590 gttcctgccc ctggatttgg aacccatagt cttgggtgac cgtggacagg taactccttt    2650 gtactgaatt gtctgtgtat ccttctgtat tccttatctg tgaagggtca taaacatagc    2710 tgcatcacag ggtctttaca aacttaattg gagtagcttt cacataccag tcagtatttt    2770 aaggcttttt catgtatatt ctctctgtcg atcctcttgg ggcacatatt tttgttatca    2830 tgaaaagtga ggttcaggaa ggtagagata tttgtctaag atcaaccaga tagtaagaga    2890 tagagttggt ctatagattg gacaatagtc cagtttagga agtagacaga tcagaagaga    2950 aaaatacaca cccacacaca cacacaaggc gcgcgcacac acacacacac aaacacatga    3010 gtccaacgca acaagtaagg ccccagatgg acacagaaac attaaagttg gtgcaaagag    3070 ctattccagg atgggaattt ctcatctcac ctaatcgtca gaatgttttc agctgttcag    3130 ccccacccctg atacaccaaa ttgaaaccag gagagggtc caggaaattc aattcataag    3190
```

```
ctcctggtgc tttggctgtt ccccagcgtg caaaccacac atcctgtgca gcaacttcat      3250
ttacagaggg gagcccaagg cctagcaaga gcagtttagg ggacctggca gccggaggag      3310
gcggggcttg tgcgttgccc acccagtggt ggcttgggtg gctcagcctt ctctcttatt      3370
ctctgttcac ag a ttc aag ctg aag aga ggc aaa gag gcc tgc gcc ttg        3419
              Phe Lys Leu Lys Arg Gly Lys Glu Ala Cys Ala Leu
                  65                  70                  75 gac aca gtt gga tgg gtt cag agg cac aga aaa atg ctg agg cac tgc        3467
Asp Thr Val Gly Trp Val Gln Arg His Arg Lys Met Leu Arg His Cys
                80                  85                  90 ccg tca aaa aga aaa tgagcagatt tctttccatt gtgggctctg gaaaccacat        3522
Pro Ser Lys Arg Lys
            95 ggcttcacct gtccccgaaa ctaccagccc tacaccattc cttctgccct gcttttgcta      3582 ggtcacagag gatctgcttg gtcttgataa gctatgttgt tgcactttaa acatttaaat      3642 tatacaatca tcaaccccca accctctggg ctcttggatt tcagagtgaa aacttgatgg      3702 cattgag                                                                3709

<210> SEQ ID NO 37
<211> LENGTH: 673
<212> TYPE: DNA
<213> ORGANISM: Homo sapiens
<220> FEATURE:
<221> NAME/KEY: CDS
<222> LOCATION: (67)...(450)

<400> SEQUENCE: 37
gggcaactca ccctcactca gaggtcttct ggttctggaa acaactctag ctcagccttc        60 tccacc atg agc ctc aga ctt gat acc acc cct tcc tgt aac agt gcg        108
       Met Ser Leu Arg Leu Asp Thr Thr Pro Ser Cys Asn Ser Ala
         1               5                  10 aga cca ctt cat gcc ttg cag gtg ctg ctg ctt ctg tca ttg ctg ctg        156
Arg Pro Leu His Ala Leu Gln Val Leu Leu Leu Leu Ser Leu Leu Leu
 15                  20                  25                  30 act gct ctg gct tcc tcc acc aaa gga caa act aag aga aac ttg gcg        204
Thr Ala Leu Ala Ser Ser Thr Lys Gly Gln Thr Lys Arg Asn Leu Ala
                35                  40                  45 aaa ggc aaa gag gaa agt cta gac agt gac ttg tat gct gaa ctc cgc        252
Lys Gly Lys Glu Glu Ser Leu Asp Ser Asp Leu Tyr Ala Glu Leu Arg
            50                  55                  60 tgc atg tgt ata aag aca acc tct gga att cat ccc aaa aac atc caa        300
Cys Met Cys Ile Lys Thr Thr Ser Gly Ile His Pro Lys Asn Ile Gln
65                  70                  75 agt ttg gaa gtg atc ggg aaa gga acc cat tgc aac caa gtc gaa gtg        348
Ser Leu Glu Val Ile Gly Lys Gly Thr His Cys Asn Gln Val Glu Val
        80                  85                  90 ata gcc aca ctg aag gat ggg agg aaa atc tgc ctg gac cca gat gct        396
Ile Ala Thr Leu Lys Asp Gly Arg Lys Ile Cys Leu Asp Pro Asp Ala
    95                 100                 105                 110 ccc aga atc aag aaa att gta cag aaa aaa ttg gca ggt gat gaa tct        444
Pro Arg Ile Lys Lys Ile Val Gln Lys Lys Leu Ala Gly Asp Glu Ser
                115                 120                 125 gct gat taatttgttc tgtttctgcc aaacttcttt aactcccagg aagggtagaa        500
Ala Asp ttttgaaacc ttgatttttct agagttctca tttattcagg atacctattc ttactgtatt      560
aaaatttgga tatgtgtttc attctgtctc aaaaatcaca ttttattctg agaaggttgg      620
ttaaaagatg gcagaaagaa gatgaaaata ataagcctg gtttcaaccc tct              673
```

-continued

<210> SEQ ID NO 38
<211> LENGTH: 12
<212> TYPE: PRT
<213> ORGANISM: Homo sapiens

<400> SEQUENCE: 38

Gln Val Cys Ile Asp Pro Lys Leu Lys Trp Ile Gln
 1               5                  10

<210> SEQ ID NO 39
<211> LENGTH: 2545
<212> TYPE: DNA
<213> ORGANISM: Homo sapiens
<220> FEATURE:
<221> NAME/KEY: CDS
<222> LOCATION: (40)...(414)

<400> SEQUENCE: 39

```
atccaataca ggagtgactt ggaactccat tctatcact atg aag aaa agt ggt         54
                                           Met Lys Lys Ser Gly
                                            1               5 gtt ctt ttc ctc ttg ggc atc atc ttg ctg gtt ctg att gga gtg caa       102
Val Leu Phe Leu Leu Gly Ile Ile Leu Leu Val Leu Ile Gly Val Gln
             10                  15                  20 gga acc cca gta gtg aga aag ggt cgc tgt tcc tgc atc agc acc aac       150
Gly Thr Pro Val Val Arg Lys Gly Arg Cys Ser Cys Ile Ser Thr Asn
         25                  30                  35 caa ggg act atc cac cta caa tcc ttg aaa gac ctt aaa caa ttt gcc       198
Gln Gly Thr Ile His Leu Gln Ser Leu Lys Asp Leu Lys Gln Phe Ala
     40                  45                  50 cca agc cct tcc tgc gag aaa att gaa atc att gct aca ctg aag aat       246
Pro Ser Pro Ser Cys Glu Lys Ile Glu Ile Ile Ala Thr Leu Lys Asn
 55                  60                  65 gga gtt caa aca tgt cta aac cca gat tca gca gat gtg aag gaa ctg       294
Gly Val Gln Thr Cys Leu Asn Pro Asp Ser Ala Asp Val Lys Glu Leu
 70                  75                  80                  85 att aaa aag tgg gag aaa cag gtc agc caa aag aaa aag caa aag aat       342
Ile Lys Lys Trp Glu Lys Gln Val Ser Gln Lys Lys Lys Gln Lys Asn
             90                  95                 100 ggg aaa aaa cat caa aaa aag aaa gtt ctg aaa gtt cga aaa tct caa       390
Gly Lys Lys His Gln Lys Lys Lys Val Leu Lys Val Arg Lys Ser Gln
        105                 110                 115 cgt tct cgt caa aag aag act aca taagagacca cttaccaat aagtattctg       444
Arg Ser Arg Gln Lys Lys Thr Thr
        120                 125 tgttaaaaat gttctatttt aattataccg ctatcattcc aaaggaggat ggcatataat     504
acaaaggctt attaatttga ctagaaaatt taaaacatta ctctgaaatt gtaactaaag     564
ttagaaagtt gattttaaga atccaaacgt taagaattgt taaaggctat gattgtcttt     624
gttcttctac cacccaccag ttgaatttca tcatgcttaa ggccatgatt ttagcaatac     684
ccatgtctac acagatgttc acccaaccac atcccactca caacagctgc ctggaagagc     744
agccctaggc ttccacgtac tgcagcctcc agagagtatc tgaggcacat gtcagcaagt     804
cctaagcctg ttagcatgct ggtgagccaa gcagtttgaa attgagctgg acctcaccaa     864
gctgctgtgg ccatcaacct ctgtatttga atcagcctac aggcctcaca cacaatgtgt     924
ctgagagatt catgctgatt gttattgggt atcaccactg gagatcacca gtgtgtggct     984
ttcagagcct cctttctggc tttggaagcc atgtgattcc atcttgcccg ctcaggctga    1044
```

```
ccactttatt tcttttttgtt cccctttgct tcattcaagt cagctcttct ccatcctacc    1104
acaatgcagt gcctttcttc tctccagtgc acctgtcata tgctctgatt tatctgagtc    1164
aactcctttc tcatcttgtc cccaacaccc cacagaagtg ctttcttctc ccaattcatc    1224
ctcactcagt ccagcttagt tcaagtcctg cctcttaaat aaacctttt  ggacacacaa    1284 attatcttaa aactcctgtt tcacttggtt cagtaccaca tgggtgaaca ctcaatggtt    1344
aactaattct tgggtgttta tcctatctct ccaaccagat tgtcagctcc ttgagggcaa    1404
gagccacagt atatttccct gtttcttcca cagtgcctaa taatactgtg aactaggtt     1464 ttaataattt tttaattgat gttgttatgg gcaggatggc aaccagacca ttgtctcaga    1524
gcaggtgctg gctctttcct ggctactcca tgttggctag cctctggtaa cctcttactt    1584
attatcttca ggacactcac tacagggacc agggatgatg caacatcctt gtcttttat    1644 gacaggatgt ttgctcagct tctccaacaa taagaagcac gtggtaaaac acttgcggat    1704
attctggact gttttaaaa  aatatacagt ttaccgaaaa tcatataatc ttacaatgaa    1764 aaggactta  tagatcagcc agtgaccaac cttttcccaa ccatacaaaa attccttttc    1824
ccgaaggaaa agggctttct caataagcct cagctttcta agatctaaca agatagccac    1884
cgagatcctt atcgaaactc attttaggca aatatgagtt ttattgtccg tttacttgtt    1944
tcagagtttg tattgtgatt atcaattacc acaccatctc ccatgaagaa agggaacggt    2004
gaagtactaa gcgctagagg aagcagccaa gtcggttagt ggaagcatga ttggtgccca    2064
gttagcctct gcaggatgtg gaaacctcct tccaggggag gttcagtgaa ttgtgtagga    2124
gaggttgtct gtggccagaa tttaaaccta tactcacttt cccaaattga atcactgctc    2184
acactgctga tgatttagag tgctgtccgg tggagatccc acccgaacgt cttatctaat    2244
catgaaactc cctagttcct tcatgtaact tccctgaaaa atctaagtgt ttcataaatt    2304
tgagagtctg tgacccactt accttgcatc tcacaggtag acagtatata actaacaacc    2364
aaagactaca tattgtcact gacacacacg ttataatcat ttatcatata tatacataca    2424
tgcatacact ctcaaagcaa ataatttttc acttcaaaac agtattgact tgtatacctt    2484
gtaatttgaa atattttctt tgttaaaata gaatggtatc aataaataga ccattaatca    2544
g                                                                   2545
```

<210> SEQ ID NO 40
<211> LENGTH: 12
<212> TYPE: PRT
<213> ORGANISM: Homo sapiens

<400> SEQUENCE: 40

Glu Leu Cys Leu Asp Pro Lys Glu Asn Trp Val Gln
1               5                   10

<210> SEQ ID NO 41
<211> LENGTH: 12
<212> TYPE: PRT
<213> ORGANISM: Homo sapiens

<400> SEQUENCE: 41

Glu Ile Cys Leu Asp Pro Glu Ala Pro Phe Leu Lys
1               5                   10

<210> SEQ ID NO 42
<211> LENGTH: 12
<212> TYPE: PRT
<213> ORGANISM: Homo sapiens

```
<400> SEQUENCE: 42

Gln Val Cys Ala Asp Pro Ser Glu Glu Trp Val Gln
 1               5                  10

<210> SEQ ID NO 43
<211> LENGTH: 12
<212> TYPE: PRT
<213> ORGANISM: Homo sapiens

<400> SEQUENCE: 43

Gln Val Cys Ala Asp Pro Ser Glu Ser Trp Val Gln
 1               5                  10

<210> SEQ ID NO 44
<211> LENGTH: 12
<212> TYPE: PRT
<213> ORGANISM: Homo sapiens

<400> SEQUENCE: 44

Gln Val Cys Ala Asp Pro Ser Glu Ser Trp Val Gln
 1               5                  10

<210> SEQ ID NO 45
<211> LENGTH: 125
<212> TYPE: PRT
<213> ORGANISM: Homo sapiens

<400> SEQUENCE: 45

Met Lys Lys Ser Gly Val Leu Phe Leu Leu Gly Ile Ile Leu Leu Val
 1               5                  10                  15

Leu Ile Gly Val Gln Gly Thr Pro Val Val Arg Lys Gly Arg Cys Ser
             20                  25                  30

Cys Ile Ser Thr Asn Gln Gly Thr Ile His Leu Gln Ser Leu Lys Asp
         35                  40                  45

Leu Lys Gln Phe Ala Pro Ser Pro Ser Cys Glu Lys Ile Glu Ile Ile
     50                  55                  60

Ala Thr Leu Lys Asn Gly Val Gln Thr Cys Leu Asn Pro Asp Ser Ala
 65                  70                  75                  80

Asp Val Lys Glu Leu Ile Lys Lys Trp Glu Lys Gln Val Ser Gln Lys
                 85                  90                  95

Lys Lys Gln Lys Asn Gly Lys Lys His Gln Lys Lys Val Leu Lys
             100                 105                 110

Val Arg Lys Ser Gln Arg Ser Arg Gln Lys Lys Thr Thr
         115                 120                 125

<210> SEQ ID NO 46
<211> LENGTH: 128
<212> TYPE: PRT
<213> ORGANISM: Homo sapiens

<400> SEQUENCE: 46

Met Ser Leu Arg Leu Asp Thr Thr Pro Ser Cys Asn Ser Ala Arg Pro
 1               5                  10                  15

Leu His Ala Leu Gln Val Leu Leu Leu Ser Leu Leu Leu Thr Ala
             20                  25                  30

Leu Ala Ser Ser Thr Lys Gly Gln Thr Lys Arg Asn Leu Ala Lys Gly
         35                  40                  45

Lys Glu Glu Ser Leu Asp Ser Asp Leu Tyr Ala Glu Leu Arg Cys Met
     50                  55                  60
```

-continued

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
            100                 105                 110

Ile Lys Lys Ile Val Gln Lys Leu Ala Gly Asp Glu Ser Ala Asp
            115                 120                 125

<210> SEQ ID NO 47
<211> LENGTH: 96
<212> TYPE: PRT
<213> ORGANISM: Homo sapiens

<400> SEQUENCE: 47

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
                20                  25                  30

Cys Cys Phe Ser Phe Ala Glu Gln Glu Ile Pro Leu Arg Ala Ile Leu
            35                  40                  45

Cys Tyr Arg Asn Thr Ser Ser Ile Cys Ser Asn Glu Gly Leu Ile Phe
        50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95

<210> SEQ ID NO 48
<211> LENGTH: 93
<212> TYPE: PRT
<213> ORGANISM: Homo sapiens

<400> SEQUENCE: 48

Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
                20                  25                  30

Ser Glu Cys Cys Phe Thr Tyr Thr Thr Tyr Lys Ile Pro Arg Gln Arg
            35                  40                  45

Ile Met Asp Tyr Tyr Glu Thr Asn Ser Gln Cys Ser Lys Pro Gly Ile
        50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 49
<211> LENGTH: 93
<212> TYPE: PRT
<213> ORGANISM: Homo sapiens

<400> SEQUENCE: 49

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

-continued

```
Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
 50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90
```

<210> SEQ ID NO 50
<211> LENGTH: 98
<212> TYPE: PRT
<213> ORGANISM: Homo sapiens

<400> SEQUENCE: 50

```
Met Lys Val Ser Ala Val Leu Leu Cys Leu Leu Met Thr Ala Ala
 1               5                  10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
        35                  40                  45

Lys Ser Tyr Val Ile Thr Thr Ser Arg Cys Pro Gln Lys Ala Val Ile
 50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr
```

<210> SEQ ID NO 51
<211> LENGTH: 839
<212> TYPE: DNA
<213> ORGANISM: Homo sapiens
<220> FEATURE:
<221> NAME/KEY: CDS
<222> LOCATION: (54)...(344)

<400> SEQUENCE: 51

```
caacccagaa accaccacct ctcacgccaa agctcacacc ttcagcctcc aac atg      56
                                                            Met
                                                             1 aag gtc tcc gca gca ctt ctg tgg ctg ctc ata gca gct gcc ttc        104
Lys Val Ser Ala Ala Leu Leu Trp Leu Leu Ile Ala Ala Ala Phe
              5                  10                  15 agc ccc cag ggg ctc gct ggg cca gct tct gtc cca acc acc tgc tgc    152
Ser Pro Gln Gly Leu Ala Gly Pro Ala Ser Val Pro Thr Thr Cys Cys
             20                  25                  30 ttt aac ctg gcc aat agg aag ata ccc ctt cag cga cta gag agc tac    200
Phe Asn Leu Ala Asn Arg Lys Ile Pro Leu Gln Arg Leu Glu Ser Tyr
         35                  40                  45 agg aga atc acc agt ggc aaa tgt ccc cag aaa gct gtg atc ttc aag    248
Arg Arg Ile Thr Ser Gly Lys Cys Pro Gln Lys Ala Val Ile Phe Lys
 50                  55                  60                  65 acc aaa ctg gcc aag gat atc tgt gcc gac ccc aag aag aag tgg gtg    296
Thr Lys Leu Ala Lys Asp Ile Cys Ala Asp Pro Lys Lys Lys Trp Val
                 70                  75                  80 cag gat tcc atg aag tat ctg gac caa aaa tct cca act cca aag cca    344
Gln Asp Ser Met Lys Tyr Leu Asp Gln Lys Ser Pro Thr Pro Lys Pro
             85                  90                  95
```

| | |
|---|---|
| taaataatca ccatttttga aaccaaacca gagcctgagt gttgcctaat ttgttttccc | 404 |
| ttcttacaat gcattctgag gtaacctcat tatcagtcca aagggcatgg gttttattat | 464 |
| atatatatat atatatttt ttttaaaaaa aaacgtattg catttaattt attgaggctt | 524 |
| taaaacttat cctccatgaa tatcagttat ttttaaactg taaagctttg tgcagattct | 584 |
| ttaccccctg ggagcccaa ttcgatcccc tgtcacgtgt gggcaatgtt ccccctctcc | 644 |
| tctcttcctc cctggaatct tgtaaaggtc ctggcaaaga tgatcagtat gaaaatgtca | 704 |
| ttgttcttgt gaacccaaag tgtgactcat taaatggaag taatgttgtt ttaggaatac | 764 |
| ataaagtatg tgcatatttt attatagtca ctagttgtaa ttttttttgtg ggaaatccac | 824 |
| actgagctga ggggg | 839 |

<210> SEQ ID NO 52
<211> LENGTH: 114
<212> TYPE: PRT
<213> ORGANISM: Homo sapiens

<400> SEQUENCE: 52

Met Ser Leu Leu Ser Ser Arg Ala Ala Arg Val Pro Gly Pro Ser Ser
 1               5                  10                  15

Ser Leu Cys Ala Leu Leu Val Leu Leu Leu Leu Thr Gln Pro Gly
            20                  25                  30

Pro Ile Ala Ser Ala Gly Pro Ala Ala Val Leu Arg Glu Leu Arg
        35                  40                  45

Cys Val Cys Leu Gln Thr Thr Gln Gly Val His Pro Lys Met Ile Ser
50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn

<210> SEQ ID NO 53
<211> LENGTH: 107
<212> TYPE: PRT
<213> ORGANISM: Homo sapiens

<400> SEQUENCE: 53

Met Ala Arg Ala Thr Leu Ser Ala Ala Pro Ser Asn Pro Arg Leu Leu
 1               5                  10                  15

Arg Val Ala Leu Leu Leu Leu Leu Val Ala Ala Ser Arg Arg Ala
            20                  25                  30

Ala Gly Ala Pro Leu Ala Thr Glu Leu Arg Cys Gln Cys Leu Gln Thr
        35                  40                  45

Leu Gln Gly Ile His Leu Lys Asn Ile Gln Ser Val Lys Val Lys Ser
    50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105

<210> SEQ ID NO 54
<211> LENGTH: 98
<212> TYPE: PRT
<213> ORGANISM: Homo sapiens

<400> SEQUENCE: 54

```
Met Asn Pro Ser Ala Ala Val Ile Phe Cys Leu Ile Leu Leu Gly Leu
 1               5                  10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
         35                 40                  45

Glu Ile Ile Pro Ala Ser Leu Ser Cys Pro Arg Val Glu Ile Ile Ala
 50                  55                  60

Thr Met Lys Lys Asn Asp Glu Gln Arg Cys Leu Asn Pro Glu Ser Lys
65                  70                  75                  80

Thr Ile Lys Asn Leu Met Lys Ala Phe Ser Gln Lys Arg Ser Lys Arg
                85                  90                  95

Ala Pro
```

<210> SEQ ID NO 55
<211> LENGTH: 1041
<212> TYPE: DNA
<213> ORGANISM: Homo sapiens
<220> FEATURE:
<221> NAME/KEY: CDS
<222> LOCATION: (18)...(338)

<400> SEQUENCE: 55

```
cccgcctgct gagcccc atg gcc cgc gct gct ctc tcc gcc gcc ccc agc      50
                   Met Ala Arg Ala Ala Leu Ser Ala Ala Pro Ser
                    1               5                   10 aat ccc cgg ctc ctg cga gtg gca ctg ctg ctc ctg ctc ctg gta gcc     98
Asn Pro Arg Leu Leu Arg Val Ala Leu Leu Leu Leu Leu Leu Val Ala
             15                  20                  25 gct ggc cgg cgc gca gca gga gcg tcc gtg gcc act gaa ctg cgc tgc    146
Ala Gly Arg Arg Ala Ala Gly Ala Ser Val Ala Thr Glu Leu Arg Cys
         30                  35                  40 cag tgc ttg cag acc ctg cag gga att cac ccc aag aac atc caa agt    194
Gln Cys Leu Gln Thr Leu Gln Gly Ile His Pro Lys Asn Ile Gln Ser
 45                  50                  55 gtg aac gtg aag tcc ccc gga ccc cac tgc gcc caa acc gaa gtc ata    242
Val Asn Val Lys Ser Pro Gly Pro His Cys Ala Gln Thr Glu Val Ile
 60                  65                  70                  75 gcc aca ctc aag aat ggg cgg aaa gct tgc ctc aat cct gca tcc ccc    290
Ala Thr Leu Lys Asn Gly Arg Lys Ala Cys Leu Asn Pro Ala Ser Pro
                 80                  85                  90 ata gtt aag aaa atc atc gaa aag atg ctg aac agt gac aaa tcc aac    338
Ile Val Lys Lys Ile Ile Glu Lys Met Leu Asn Ser Asp Lys Ser Asn
             95                  100                 105 tgaccagaag ggaggaggaa gctcactggt ggctgttcct gaaggaggcc ctgcccttat    398
aggaacagaa gaggaaagag agacacagct gcagaggcca cctggattgt gcctaatgtg    458
tttgagcatc gcttaggaga agtcttctat ttatttattt attcattagt tttgaagatt    518
ctatgttaat attttaggtg taaataatt aagggtatga ttaactctac ctgcacactg     578
tcctattata ttcattcttt tgaaatgtc aaccccaagt tagttcaatc tggattcata     638
tttaatttga aggtagaatg ttttcaaatg ttctccagtc attatgttaa tatttctgag    698
gagcctgcaa catgccagcc actgtgatag aggctggcgg atccaagcaa atggccaatg    758
```

| | | |
|---|---|---|
| agatcattgt gaaggcaggg gaatgtatgt gcacatctgt tttgtaactg tttagatgaa | 818 |
| tgtcagttgt tatttattga aatgatttca cagtgtgtgg tcaacatttc tcatgttgaa | 878 |
| actttaagaa ctaaaatgtt ctaaatatcc cttggacatt ttatgtcttt cttgtaaggc | 938 |
| atactgcctt gtttaatggt agttttacag tgtttctggc ttagaacaaa ggggcttaat | 998 |
| tattgatgtt ttcatagaga atataaaaat aaagcactta tag | 1041 |

<210> SEQ ID NO 56
<211> LENGTH: 93
<212> TYPE: PRT
<213> ORGANISM: Homo sapiens

<400> SEQUENCE: 56

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 57
<211> LENGTH: 107
<212> TYPE: PRT
<213> ORGANISM: Homo sapiens

<400> SEQUENCE: 57

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
                20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
        50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
                100                 105

<210> SEQ ID NO 58
<211> LENGTH: 1560
<212> TYPE: DNA
<213> ORGANISM: Homo sapiens
<220> FEATURE:
<221> NAME/KEY: CDS
<222> LOCATION: (102)...(398)

<400> SEQUENCE: 58

| | | |
|---|---|---|
| ctccataagg cacaaacttt cagagacagc agagcacaca agcttctagg acaagagcca | 60 |
| ggaagaaacc accggaagga accatctcac tgtgtgtaaa c atg act tcc aag ctg | 116 |

```
                    Met Thr Ser Lys Leu
                      1               5 gcc gtg gct ctc ttg gca gcc ttc ctg att tct gca gct ctg tgt gaa        164
Ala Val Ala Leu Leu Ala Ala Phe Leu Ile Ser Ala Ala Leu Cys Glu
             10                  15                  20 ggt gca gtt ttg cca agg agt gct aaa gaa ctt aga tgt cag tgc ata        212
Gly Ala Val Leu Pro Arg Ser Ala Lys Glu Leu Arg Cys Gln Cys Ile
         25                  30                  35 aag aca tac tcc aaa cct ttc cac ccc aaa ttt atc aaa gaa ctg aga        260
Lys Thr Tyr Ser Lys Pro Phe His Pro Lys Phe Ile Lys Glu Leu Arg
     40                  45                  50 gtg att gag agt gga cca cac tgc gcc aac aca gaa att att gta aag        308
Val Ile Glu Ser Gly Pro His Cys Ala Asn Thr Glu Ile Ile Val Lys
 55                  60                  65 ctt tct gat gga aga gag ctc tgt ctg gac ccc aag gaa aac tgg gtg        356
Leu Ser Asp Gly Arg Glu Leu Cys Leu Asp Pro Lys Glu Asn Trp Val
 70                  75                  80                  85 cag agg gtt gtg gag aag ttt ttg aag agg gct gag aat tca                398
Gln Arg Val Val Glu Lys Phe Leu Lys Arg Ala Glu Asn Ser
             90                  95 taaaaaaatt cattctctgt ggtatccaag aatcagtgaa gatgccagtg aaacttcaag      458
caaatctact tcaacacttc atgtattgtg tgggtctgtt gtagggttgc cagatgcaat      518
acaagattcc tggttaaatt tgaatttcag taaacaatga atagttttc attgtaccat       578
gaaatatcca gaacatactt atatgtaaag tattatttat ttgaatctac aaaaaacaac      638
aaataatttt taaatataag gattttccta gatattgcac gggagaatat acaaatagca      698
aaattgggcc aagggccaag agaatatccg aactttaatt tcaggaattg aatgggtttg      758
ctagaatgtg atatttgaag catcacataa aaatgatggg acaataaatt ttgccataaa      818
gtcaaattta gctggaaatc ctggattttt ttctgttaaa tctggcaacc ctagtctgct      878
agccaggatc cacaagtcct tgttccactg tgccttggtt tctcctttat ttctaagtgg      938
aaaaagtatt agccaccatc ttacctcaca gtgatgttgt gaggacatgt ggaagcactt      998
taagtttttt catcataaca taaattattt tcaagtgtaa cttattaacc tatttattat     1058
ttatgtattt atttaagcat caaatatttg tgcaagaatt tggaaaaata gaagatgaat     1118
cattgattga atagttataa agatgttata gtaaatttat tttattttag atattaaatg     1178
atgttttatt agataaattt caatcagggt ttttagatta aacaaacaaa caattgggta     1238
cccagttaaa ttttcatttc agatatacaa caaataattt tttagtataa gtacattatt     1298
gtttatctga aattttaatt gaactaacaa tcctagtttg atactcccag tcttgtcatt     1358
gccagctgtg ttggtagtgc tgtgttgaat tacggaataa tgagttagaa ctattaaaac     1418
agccaaaact ccacagtcaa tattagtaat ttcttgctgg ttgaaacttg tttattatgt     1478
acaaatagat tcttataata ttatttaaat gactgcattt ttaaatacaa ggctttatat     1538
ttttaacttt aaaaaaaacc gg                                              1560

<210> SEQ ID NO 59
<211> LENGTH: 15
<212> TYPE: PRT
<213> ORGANISM: Homo sapiens

<400> SEQUENCE: 59

Asn Leu Gln Val Phe Ala Ile Gly Pro Gln Cys Ser Lys Val Glu
 1               5                  10                  15
```

```
<210> SEQ ID NO 60
<211> LENGTH: 14
<212> TYPE: PRT
<213> ORGANISM: Homo sapiens

<400> SEQUENCE: 60

Val Asp Tyr Tyr Glu Thr Ser Ser Leu Cys Ser Gln Pro Ala
 1               5                  10

<210> SEQ ID NO 61
<211> LENGTH: 15
<212> TYPE: PRT
<213> ORGANISM: Homo sapiens

<400> SEQUENCE: 61

Val Asp Tyr Tyr Glu Thr Ser Ser Leu Cys Ser Gln Pro Ala Val
 1               5                  10                  15

<210> SEQ ID NO 62
<211> LENGTH: 15
<212> TYPE: PRT
<213> ORGANISM: Homo sapiens

<400> SEQUENCE: 62

Glu Ser Tyr Arg Arg Ile Thr Asn Ile Gln Cys Pro Lys Glu Ala
 1               5                  10                  15

<210> SEQ ID NO 63
<211> LENGTH: 15
<212> TYPE: PRT
<213> ORGANISM: Homo sapiens

<400> SEQUENCE: 63

Glu Ser Tyr Arg Arg Thr Thr Ser Ser His Cys Pro Arg Glu Ala
 1               5                  10                  15

<210> SEQ ID NO 64
<211> LENGTH: 15
<212> TYPE: PRT
<213> ORGANISM: Homo sapiens

<400> SEQUENCE: 64

Lys Ser Tyr Val Ile Thr Thr Ser Arg Cys Pro Gln Lys Ala Val
 1               5                  10                  15

<210> SEQ ID NO 65
<211> LENGTH: 12
<212> TYPE: PRT
<213> ORGANISM: Homo sapiens

<400> SEQUENCE: 65

Glu Ile Cys Ala Asp Pro Lys Glu Lys Trp Val Gln
 1               5                  10

<210> SEQ ID NO 66
<211> LENGTH: 12
<212> TYPE: PRT
<213> ORGANISM: Homo sapiens

<400> SEQUENCE: 66

Glu Ile Cys Ala Asp Pro Thr Gln Lys Trp Val Gln
 1               5                  10

<210> SEQ ID NO 67
<211> LENGTH: 12
```

```
<212> TYPE: PRT
<213> ORGANISM: Homo sapiens

<400> SEQUENCE: 67

Glu Ile Cys Ala Asp Pro Lys Glu Arg Trp Val Arg
 1               5                  10

<210> SEQ ID NO 68
<211> LENGTH: 16
<212> TYPE: PRT
<213> ORGANISM: Homo sapiens
<220> FEATURE:
<221> NAME/KEY: SITE
<222> LOCATION: (1)...(16)
<223> OTHER INFORMATION: Xaa = any amino acid

<400> SEQUENCE: 68

Met Ile Cys Ala Asp Pro Lys Xaa Ala Ala Xaa Ala Ala Trp Val Gln
 1               5                  10                  15

<210> SEQ ID NO 69
<211> LENGTH: 15
<212> TYPE: PRT
<213> ORGANISM: Homo sapiens

<400> SEQUENCE: 69

Ser Val Asn Val Lys Ser Pro Gly Pro His Cys Ala Gln Thr Glu
 1               5                  10                  15

<210> SEQ ID NO 70
<211> LENGTH: 15
<212> TYPE: PRT
<213> ORGANISM: Homo sapiens

<400> SEQUENCE: 70

Ser Val Lys Val Lys Ser Pro Gly Pro His Cys Ala Gln Thr Glu
 1               5                  10                  15

<210> SEQ ID NO 71
<211> LENGTH: 15
<212> TYPE: PRT
<213> ORGANISM: Homo sapiens

<400> SEQUENCE: 71

Ser Val Asn Val Arg Ser Pro Gly Pro His Cys Ala Gln Thr Glu
 1               5                  10                  15

<210> SEQ ID NO 72
<211> LENGTH: 12
<212> TYPE: PRT
<213> ORGANISM: Homo sapiens

<400> SEQUENCE: 72

Lys Ala Cys Leu Asn Pro Ala Ser Pro Ile Val Lys
 1               5                  10

<210> SEQ ID NO 73
<211> LENGTH: 12
<212> TYPE: PRT
<213> ORGANISM: Homo sapiens

<400> SEQUENCE: 73

Lys Ala Cys Leu Asn Pro Ala Ser Pro Met Val Lys
 1               5                  10
```

```
<210> SEQ ID NO 74
<211> LENGTH: 12
<212> TYPE: PRT
<213> ORGANISM: Homo sapiens

<400> SEQUENCE: 74

Lys Ala Cys Leu Asn Pro Ala Ser Pro Met Val Gln
 1               5                  10

<210> SEQ ID NO 75
<211> LENGTH: 12
<212> TYPE: PRT
<213> ORGANISM: Homo sapiens

<400> SEQUENCE: 75

Lys Ser Tyr Lys Ile Ile Thr Ser Ser Lys Cys Pro
 1               5                  10

<210> SEQ ID NO 76
<211> LENGTH: 661
<212> TYPE: DNA
<213> ORGANISM: Homo sapiens
<220> FEATURE:
<221> NAME/KEY: CDS
<222> LOCATION: (32)...(331)

<400> SEQUENCE: 76
tcaaactgaa gctcgcactc tcgcctccag c atg aaa gtc tct gcc gcc ctt         52
                                   Met Lys Val Ser Ala Ala Leu
                                    1               5 ctg tgc ctg ctg ctc ata gca gcc acc ttc att ccc caa ggg ctc gct       100
Leu Cys Leu Leu Leu Ile Ala Ala Thr Phe Ile Pro Gln Gly Leu Ala
         10                  15                  20 cag cca gat gca atc aat gcc cca gtc acc tgc tgc tat aac ttc acc       148
Gln Pro Asp Ala Ile Asn Ala Pro Val Thr Cys Cys Tyr Asn Phe Thr
     25                  30                  35 aat agg aag atc tca gtg cag agg ctc gcg agc tat aga aga atc acc       196
Asn Arg Lys Ile Ser Val Gln Arg Leu Ala Ser Tyr Arg Arg Ile Thr
 40                  45                  50                  55 agc agc aag tgt ccc aaa gaa gct gtg atc ttc aag acc att gtg gcc       244
Ser Ser Lys Cys Pro Lys Glu Ala Val Ile Phe Lys Thr Ile Val Ala
                 60                  65                  70 aag gag atc tgt gct gac ccc aag cag aag tgg gtt cag gat tcc atg       292
Lys Glu Ile Cys Ala Asp Pro Lys Gln Lys Trp Val Gln Asp Ser Met
             75                  80                  85 gac cac ctg gac aag caa acc caa act ccg aag act tga acactcactc       341
Asp His Leu Asp Lys Gln Thr Gln Thr Pro Lys Thr  *
         90                  95 cacaacccaa gaatctgcag ctaacttatt ttcccctagc tttccccaga catcctgttt     401
tattttatta taatgaattt tgtttgttga tgtgaaacat tatgccttaa gtaatgttaa     461
ttcttattta agttattgat gttttaagtt tatctttcat ggtactagtg ttttttagat     521
acagagactt ggggaaattg cttttcctct tgaaccacag ttctacccct gggatgtttt     581
gagggtcttt gcaagaatca ttttttttaac attccaatgc atttaataca aagaattgct     641
aaaatattat tgtggaaatg                                                  661

<210> SEQ ID NO 77
<211> LENGTH: 1847
<212> TYPE: DNA
<213> ORGANISM: Homo sapiens
<220> FEATURE:
<221> NAME/KEY: CDS
```

<222> LOCATION: (80)...(346)

<400> SEQUENCE: 77

```
tctccgtcag ccgcattgcc cgctcggcgt ccggcccccg acccgtgctc gtccgcccgc      60
ccgcccgccc gcccgcgcc atg aac gcc aag gtc gtg gtc gtg ctg gtc ctc     112
                     Met Asn Ala Lys Val Val Val Val Leu Val Leu
                      1               5                  10 gtg ctg acc gcg ctc tgc ctc agc gac ggg aag ccc gtc agc ctg agc      160
Val Leu Thr Ala Leu Cys Leu Ser Asp Gly Lys Pro Val Ser Leu Ser
         15                  20                  25 tac aga tgc cca tgc cga ttc ttc gaa agc cat gtt gcc aga gcc aac      208
Tyr Arg Cys Pro Cys Arg Phe Phe Glu Ser His Val Ala Arg Ala Asn
 30                  35                  40 gtc aag cat ctc aaa att ctc aac act cca aac tgt gcc ctt cag att      256
Val Lys His Leu Lys Ile Leu Asn Thr Pro Asn Cys Ala Leu Gln Ile
         45                  50                  55 gta gcc cgg ctg aag aac aac aac aga caa gtg tgc att gac ccg aag      304
Val Ala Arg Leu Lys Asn Asn Asn Arg Gln Val Cys Ile Asp Pro Lys
 60                  65                  70                  75 cta aag tgg att cag gag tac ctg gag aaa gct tta aac aag              346
Leu Lys Trp Ile Gln Glu Tyr Leu Glu Lys Ala Leu Asn Lys
                 80                  85 taagcacaac agccaaaaag gactttccgc tagaccccact cgaggaaaac taaaaccttg    406
tgagagatga aagggcaaag acgtgggggga gggggccttaa ccatgagga ccaggtgtgt   466
```

(continuing with non-coding sequence, positions 466–1846 as shown)

```
gtgtggggtg ggcacattga tctgggatcg ggcctgaggt ttgcagcatt tagaccctgc    526
atttatagca tacggtatga tattgcagct tatattcatc catgccctgt acctgtgcac    586
gttggaactt ttattactgg ggttttttcta agaaagaaat tgtattatca acagcatttt   646
caagcagtta gttccttcat gatcatcaca atcatcatca ttctcattct catttttaa    706
atcaacgagt acttcaagat ctgaatttgg cttgtttgga gcatctcctc tgctcccctg    766
gggagtctgg gcacagtcag gtggtggctt aacagggagc tggaaaaagt gtcctttctt    826
cagacactga ggctcccgca gcagcgcccc tcccaagagg aaggcctctg tggcactcag    886
ataccgactg gggctggggc gccgccactg ccttcacctc ctctttcaaa cctcagtgat    946
tggctctgtg ggctccatgt agaagccact attactggga ctgtctcaga gacccctctc   1006
ccagctattc ctactctctc cccgactccg agagcatgct taatcttgct tctgcttctc   1066
atttctgtag cctgatcagc gccgcaccag ccgggaagag ggtgattgct ggggctcgtg   1126
ccctgcatcc ctctcctccc agggcctgcc ccacagctcg ggccctctgt gagatccgtc   1186
tttggcctcc tccagaatgg agctggccct ctcctgggga tgtgtaatgg tcccctgct    1246
tacccgcaaa agacaagtct ttacagaatc aaatgcaatt ttaaatctga gagctcgctt   1306
gagtgactgg gtttgtgatt gcctctgaag cctatgtatg ccatggaggc actaacaaac   1366
tctgaggttt ccgaaatcag aagcgaaaaa atcagtgaat aaaccatcat cttgccacta   1426
cccccctcctg aagccacagc agggggttcag gttccaatca gaactgttgg caaggtgaca   1486
tttccatgca tagatgcgat ccacagaagg tcctggtggt atttgtaact ttttgcaagg   1546
cattttttta tatatatttt tgtgcacatt ttttttttacg attctttaga aaacaaatgt   1606
atttcaaaat atatttatag tcgaacaagt catatatatg aatgagagcc atatgaatgt   1666
cagtagttta tacttctcta ttatctcaaa ctactggcaa tttgtaaaga aatatatatg   1726
atatataaat gtgattgcag cttttcaatg ttagccacag tgtatttttt cacttgtact   1786
aaaattgtat caaatgtgac attatatgca ctagcaataa aatgctaatt gtttcatggt   1846
```

```
a                                                                    1847

<210> SEQ ID NO 78
<211> LENGTH: 1160
<212> TYPE: DNA
<213> ORGANISM: Homo sapiens
<220> FEATURE:
<221> NAME/KEY: CDS
<222> LOCATION: (27)...(299)

<400> SEQUENCE: 78
cctccgacag cctctccaca ggtacc atg aag gtc tcc gcg gca cgc ctc gct       53
                             Met Lys Val Ser Ala Ala Arg Leu Ala
                              1               5 gtc atc ctc att gct act gcc ctc tgc gct cct gca tct gcc tcc cca      101
Val Ile Leu Ile Ala Thr Ala Leu Cys Ala Pro Ala Ser Ala Ser Pro
 10                  15                  20                  25 tat tcc tcg gac acc aca ccc tgc tgc ttt gcc tac att gcc cgc cca      149
Tyr Ser Ser Asp Thr Thr Pro Cys Cys Phe Ala Tyr Ile Ala Arg Pro
                 30                  35                  40 ctg ccc cgt gcc cac atc aag gag tat ttc tac acc agt ggc aag tgc      197
Leu Pro Arg Ala His Ile Lys Glu Tyr Phe Tyr Thr Ser Gly Lys Cys
             45                  50                  55 tcc aac cca gca gtc gtc ttt gtc acc cga aag aac cgc caa gtg tgt      245
Ser Asn Pro Ala Val Val Phe Val Thr Arg Lys Asn Arg Gln Val Cys
         60                  65                  70 gcc aac cca gag aag aaa tgg gtt cgg gag tac atc aac tct ttg gag      293
Ala Asn Pro Glu Lys Lys Trp Val Arg Glu Tyr Ile Asn Ser Leu Glu
     75                  80                  85 atg agc taggatggag agtccttgaa cctgaactta cacaaatttg cctgtttctg       349
Met Ser
 90 cttgctcttg tcctagcttg ggaggcttcc cctcactatc ctaccccacc cgctccttga    409 agggcccaga ttctgaccac gacgagcagc agttacaaaa accttcccca ggctggacgt    469 ggtggctcag ccttgtaatc ccagcacttt gggaggccaa ggtgggtgga tcacttgagg    529 tcaggagttc gagacagcct ggccaacatg atgaaacccc atgtgtacta aaatacaaa     589 aaattagccg ggcgtggtag cgggcgcctg tagtcccagc tactcgggag gctgaggcag    649 gagaatggcg tgaacccggg agcggagctt gcagtgagcc gagatcgcgc cactgcactc    709 cagcctgggc gacagagcga gactccgtct caaaaaaaaa aaaaaaaaa aaaaaaatac     769 aaaaattagc cgcgtggtgg cccacgcctg taatcccagc tactcgggag gctaaggcag    829 gaaaattgtt tgaacccagg aggtggaggc tgcagtgagc tgagattgtg ccacttcact    889 ccagcctggg tgacaaagtg agactccgtc acaacaacaa caacaaaaag cttccccaac    949 taaagcctag aagagcttct gaggcgctgc tttgtcaaaa ggaagtctct aggttctgag   1009 ctctggcttt gccttggctt tgcaagggct ctgtgacaag gaaggaagtc agcatgcctc   1069 tagaggcaag gaagggagga acactgcact cttaagcttc cgccgtctca accctcaca   1129 ggagcttact ggcaaacatg aaaaatcggg g                                 1160

<210> SEQ ID NO 79
<211> LENGTH: 696
<212> TYPE: DNA
<213> ORGANISM: Homo sapiens
<220> FEATURE:
<221> NAME/KEY: CDS
<222> LOCATION: (109)...(384)
```

```
<400> SEQUENCE: 79
ttcccccccc cccccccccc cccgcccga gcacaggaca cagctgggtt ctgaagcttc         60
tgagttctgc agcctcacct ctgagaaaac ctcttttcca ccaatacc atg aag ctc        117
                                                     Met Lys Leu
                                                       1 tgc gtg act gtc ctg tct ctc ctc atg cta gta gct gcc ttc tgc tct        165
Cys Val Thr Val Leu Ser Leu Leu Met Leu Val Ala Ala Phe Cys Ser
      5                  10                  15 cca gcg ctc tca gca cca atg ggc tca gac cct ccc acc gcc tgc tgc        213
Pro Ala Leu Ser Ala Pro Met Gly Ser Asp Pro Pro Thr Ala Cys Cys
 20                  25                  30                  35 ttt tct tac acc gcg agg aag ctt cct cgc aac ttt gtg gta gat tac        261
Phe Ser Tyr Thr Ala Arg Lys Leu Pro Arg Asn Phe Val Val Asp Tyr
                 40                  45                  50 tat gag acc agc agc ctc tgc tcc cag cca gct gtg gta ttc caa acc        309
Tyr Glu Thr Ser Ser Leu Cys Ser Gln Pro Ala Val Val Phe Gln Thr
             55                  60                  65 aaa aga agc aag caa gtc tgt gct gat ccc agt gaa tcc tgg gtc cag        357
Lys Arg Ser Lys Gln Val Cys Ala Asp Pro Ser Glu Ser Trp Val Gln
         70                  75                  80 gag tac gtg tat gac ctg gaa ctg aac tgagctgctc agagacagga              404
Glu Tyr Val Tyr Asp Leu Glu Leu Asn
     85                  90 agtcttcagg gaaggtcacc tgagcccgga tgcttctcca tgagacacat ctcctccata      464
ctcaggactc ctctccgcag ttcctgtccc ttctcttaat ttaatctttt ttatgtgccg      524
tgttattgta ttaggtgtca tttccattat ttatattagt ttagccaaag gataagtgtc      584
ctatggggat ggtccactgt cactgttcct ctgctgttgc aaatacatgg ataacacatt      644
tgattctgtg tgttttccat aataaaactt taaaataaaa tgcagacagt ta              696

<210> SEQ ID NO 80
<211> LENGTH: 2738
<212> TYPE: DNA
<213> ORGANISM: Homo sapiens
<220> FEATURE:
<221> NAME/KEY: CDS
<222> LOCATION: (123)...(353)

<400> SEQUENCE: 80
gaacaaccca gaaaccttca cctctcatgc tgaagctcac acccttgccc tccaagatga       60
aggtttctgc agcgcttctg tgcctgctgc tcatggcagc cactttcagc cctcagggac      120 tt gct cag cca gat tca gtt tcc att cca atc acc tgc tgc ttt aac        167
   Ala Gln Pro Asp Ser Val Ser Ile Pro Ile Thr Cys Cys Phe Asn
    1               5                  10                  15 gtg atc aat agg aaa att cct atc cag agg ctg gag agc tac aca aga        215
Val Ile Asn Arg Lys Ile Pro Ile Gln Arg Leu Glu Ser Tyr Thr Arg
             20                  25                  30 atc acc aac atc caa tgt ccc aag gaa gct gtg atc ttc aag acc caa        263
Ile Thr Asn Ile Gln Cys Pro Lys Glu Ala Val Ile Phe Lys Thr Gln
         35                  40                  45 cgg ggc aag gag gtc tgt gct gac ccc aag gag aga tgg gtc agg gat        311
Arg Gly Lys Glu Val Cys Ala Asp Pro Lys Glu Arg Trp Val Arg Asp
     50                  55                  60 tcc atg aag cat ctg gac caa ata ttt caa aat ctg aag cca                353
Ser Met Lys His Leu Asp Gln Ile Phe Gln Asn Leu Lys Pro
 65                  70                  75 tgagccttca tacatggact gagagtcaga gcttgaagaa aagcttattt attttcccca      413
```

-continued

```
acctccccca ggtgcagtgt gacattattt tattataaca tccacaaaga gattattttt      473
aaataattta aagcataata tttcttaaaa agtatttaat tatatttaag ttgttgatgt      533
tttaactcta tctgtcatac atcctagtga atgtaaaatg caaaatcctg gtgatgtgtt      593
ttttgttttt gttttcctgt gagctcaact aagttcacgg caaaatgtca ttgttctccc      653
tcctacctgt ctgtagtgtt gtggggtcct cccatggatc atcaaggtga aacactttgg      713
tattctttgg caatcagtgc tcctgtaagt caaatgtgtg ctttgtactg ctgttgttga      773
aattgatgtt actgtatata actatggaat tttgaaaaaa aatttcaaaa agaaaaaaat      833
atatataatt taaaactaag aaaaaaaaaa aaaaaaaaa aaaaggtttt ctattgactt      893
gggttaatcg tgtgaccgcg gtggctggca cgaaattgac caaccctggg gttagtatag      953
cttagttaaa ctttcgttta ttgctaaagg ttaatcactg ctgtttcccg tggggtgtg      1013 gctaggctaa gcgttttgag ctgcattgct gcgtgcttga tgcttgtccc ttttgatcgt     1073
ggtgatttag agggtgaact cactggaatg gggatgcttg catgtgtaat cttactaaga     1133
gctaatagaa aggctaggac caaaccagaa acctccaatt ctcatgtgga agcccatgcc     1193
ctcaccctcc aacatgaaag cctctgcagc acttctgtgt ctgctgctca cagcagctgc     1253
tttcagcccc caggggcttg ctcagccagt tgggattaat acttcaacta cctgctgcta     1313
cagatttatc aataagaaaa tccctaagca gaggctggag agctacagaa ggaccaccag     1373
tagccactgt ccccgggaag ctgtaatctt caagaccaaa ctggacaagg agatctgtgc     1433
tgaccccaca cagaagtggg tccaggactt tatgaagcac ctggacaaga aacccaaac      1493 tccaaagctt tgaacattca tgactgaact gaaaacaagc catgacttga gaaacaaata     1553
atttgtatac cctgtccttt ctcagagtgg ttctgagatt attttaatct aattctaagg     1613
aatatgagct ttatgtaata atgtgaatca tggttttttct tagtagatttt taaaagttat    1673 taatatttta atttaatctt ccatggattt tggtgggttt tgaacataaa gccttggatg     1733
tatatgtcat ctcagtgctg taaaaactgt gggatgctcc tcccttctct acctcatggg     1793
ggtattgtat aagtccttgc aagaatcagt gcaaagattt gctttaattg ttaagatatg     1853
atgtccctat ggaagcatat tgttattata taattacata tttgcatatg tatgactccc     1913 aaatttcac ataaaataga ttttttgtata acaaaaaaaa aaaaaaaaaa aaggacacgg     1973
gcagcagaca gtggtcagtc ctttcttggc tctgctgaca ctcgagccca cattccgtca     2033
cctgctcaga atcatgcagg tctccactgc tgcccttgct gtcctcctct gcaccatggc     2093
tctctgcaac cagttctctg catcacttgc tgctgacacg ccgaccgcct gctgcttcag     2153 ctacaccctcc cggcagattc cacagaattt catagctgac tactttgaga cgagcagcca     2213
gtgctccaag cccggtgtca tcttcctaac caagcgaagc cggcaggtct gtgctgaccc     2273
cagtgaggag tgggtccaga aatatgtcag cgacctggag ctgagtgcct gagggtcca     2333 gaagcttcga ggcccagcga cctcggtggg cccagtgggg aggagcagga gcctgagcct     2393
tgggaacatg cgtgtgacct ccacagctac ctcttctatg gactggttgt tgccaaacag     2453
ccacactgtg ggactcttct taacttaaat tttaatttat ttatactatt tagttttgt      2513 aatttatttt cgatttcaca gtgtgtttgt gattgtttgc tctgagagtt ccctgtccc      2573 ctcccccttc cctcacaccg cgtctggtga caaccgagtg gctgtcatca gcctgtgtag     2633
gcagtcatgg caccaaagcc accagactga caaatgtgta tcggatgctt tgttcaggg      2693 ctgtgatcgg cctggggaaa taataaagat gctctttttaa aaggt                    2738
```

```
<210> SEQ ID NO 81
<211> LENGTH: 1085
<212> TYPE: DNA
<213> ORGANISM: Homo sapiens
<220> FEATURE:
<221> NAME/KEY: CDS
<222> LOCATION: (329)...(625)

<400> SEQUENCE: 81
ggtttctatt gacttgggtt aatcgtgtga ccgcggtggc tggcacgaaa ttgaccaacc      60
ctggggttag tatagcttag ttaaactttc gtttattgct aaaggttaat cactgctgtt     120
tcccgtgggg gtgtggctag gctaagcgtt ttgagctgca ttgctgcgtg cttgatgctt     180 gtccctttg atcgtggtga tttagagggt gaactcactg gaatggggat gcttgcatgt      240
gtaatcttac taagagctaa tagaaaggct aggaccaaac cagaaacctc caattctcat     300
gtggaagccc atgccctcac cctccaac atg aaa gcc tct gca gca ctt ctg        352
                                Met Lys Ala Ser Ala Ala Leu Leu
                                  1               5 tgt ctg ctg ctc aca gca gct gct ttc agc ccc cag ggg ctt gct cag       400
Cys Leu Leu Leu Thr Ala Ala Ala Phe Ser Pro Gln Gly Leu Ala Gln
         10                  15                  20 cca gtt ggg att aat act tca act acc tgc tgc tac aga ttt atc aat       448
Pro Val Gly Ile Asn Thr Ser Thr Thr Cys Cys Tyr Arg Phe Ile Asn
 25                  30                  35                  40 aag aaa atc cct aag cag agg ctg gag agc tac aga agg acc acc agt       496
Lys Lys Ile Pro Lys Gln Arg Leu Glu Ser Tyr Arg Arg Thr Thr Ser
                 45                  50                  55 agc cac tgt ccc cgg gaa gct gta atc ttc aag acc aaa ctg gac aag       544
Ser His Cys Pro Arg Glu Ala Val Ile Phe Lys Thr Lys Leu Asp Lys
             60                  65                  70 gag atc tgt gct gac ccc aca cag aag tgg gtc cag gac ttt atg aag       592
Glu Ile Cys Ala Asp Pro Thr Gln Lys Trp Val Gln Asp Phe Met Lys
         75                  80                  85 cac ctg gac aag aaa acc caa act cca aag ctt tgaacattca tgactgaact     645
His Leu Asp Lys Lys Thr Gln Thr Pro Lys Leu
         90                  95 gaaaacaagc catgacttga gaaacaaata atttgtatac cctgtccttt ctcagagtgg     705
ttctgagatt atttaatct aattctaagg aatatgagct ttatgtaata atgtgaatca      765 tggttttct tagtagattt taaagttat taatatttta atttaatctt ccatggattt       825
tggtgggttt tgaacataaa gccttggatg tatatgtcat ctcagtgctg taaaaactgt     885
gggatgctcc tcccttctct acctcatggg ggtattgtat aagtccttgc aagaatcagt     945
gcaaagattt gctttaattg ttaagatatg atgtccctat ggaagcatat tgttattata    1005
taattacata tttgcatatg tatgactccc aaattttcac ataaaataga ttttgtata    1065 acaaaaaaaa aaaaaaaaa                                                 1085

<210> SEQ ID NO 82
<211> LENGTH: 775
<212> TYPE: DNA
<213> ORGANISM: Homo sapiens
<220> FEATURE:
<221> NAME/KEY: CDS
<222> LOCATION: (84)...(359)

<400> SEQUENCE: 82
aaggacacgg gcagcagaca gtggtcagtc ctttcttggc tctgctgaca ctcgagccca      60
cattccgtca cctgctcaga atc atg cag gtc tcc act gct gcc ctt gct gtc    113
                          Met Gln Val Ser Thr Ala Ala Leu Ala Val
```

```
                    1               5                   10
ctc ctc tgc acc atg gct ctc tgc aac cag ttc tct gca tca ctt gct    161
Leu Leu Cys Thr Met Ala Leu Cys Asn Gln Phe Ser Ala Ser Leu Ala
                 15                  20                  25 gct gac acg ccg acc gcc tgc tgc ttc agc tac acc tcc cgg cag att    209
Ala Asp Thr Pro Thr Ala Cys Cys Phe Ser Tyr Thr Ser Arg Gln Ile
             30                  35                  40 cca cag aat ttc ata gct gac tac ttt gag acg agc agc cag tgc tcc    257
Pro Gln Asn Phe Ile Ala Asp Tyr Phe Glu Thr Ser Ser Gln Cys Ser
         45                  50                  55 aag ccc ggt gtc atc ttc cta acc aag cga agc cgg cag gtc tgt gct    305
Lys Pro Gly Val Ile Phe Leu Thr Lys Arg Ser Arg Gln Val Cys Ala
     60                  65                  70 gac ccc agt gag gag tgg gtc cag aaa tat gtc agc gac ctg gag ctg    353
Asp Pro Ser Glu Glu Trp Val Gln Lys Tyr Val Ser Asp Leu Glu Leu
 75                  80                  85                  90 agt gcc tgagggtcc agaagcttcg aggcccagcg acctcggtgg gcccagtggg      409
Ser Ala gaggagcagg agcctgagcc ttgggaacat gcgtgtgacc tccacagcta cctcttctat  469
ggactggttg ttgccaaaca gccacactgt gggactcttc ttaacttaaa ttttaattta  529
tttatactat ttagtttttg taatttattt tcgatttcac agtgtgtttg tgattgtttg  589
ctctgagagt tcccctgtcc cctccccctt ccctcacacc gcgtctggtg acaaccgagt  649
ggctgtcatc agcctgtgta ggcagtcatg gcaccaaagc caccagactg acaaatgtgt  709
atcggatgct tttgttcagg gctgtgatcg gcctggggaa ataataaaga tgctctttta  769
aaaggt                                                              775

<210> SEQ ID NO 83
<211> LENGTH: 98
<212> TYPE: PRT
<213> ORGANISM: Homo sapiens

<400> SEQUENCE: 83

Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
             20                  25                  30

Thr Cys Cys Phe Thr Phe Ser Ser Lys Lys Ile Ser Leu Gln Arg Leu
         35                  40                  45

Lys Ser Tyr Val Ile Thr Thr Ser Arg Cys Pro Gln Lys Ala Val Ile
     50                  55                  60

Phe Arg Thr Lys Leu Gly Lys Glu Ile Cys Ala Asp Pro Lys Glu Lys
 65                  70                  75                  80

Trp Val Gln Asn Tyr Met Lys His Leu Gly Arg Lys Ala His Thr Leu
                 85                  90                  95

Lys Thr

<210> SEQ ID NO 84
<211> LENGTH: 9
<212> TYPE: PRT
<213> ORGANISM: Artificial Sequence
<220> FEATURE:
<223> OTHER INFORMATION: A region within a peptide of a chemokine, a
      variant, or a derivative thereof.
<220> FEATURE:
<221> NAME/KEY: SITE
<222> LOCATION: 1
<223> OTHER INFORMATION: Xaa  is Ala or Leu
```

```
<220> FEATURE:
<221> NAME/KEY: SITE
<222> LOCATION: 4
<223> OTHER INFORMATION: Xaa is Lys, Ser or Thr
<220> FEATURE:
<221> NAME/KEY: SITE
<222> LOCATION: 5
<223> OTHER INFORMATION: Xaa is any amino acid
<220> FEATURE:
<221> NAME/KEY: SITE
<222> LOCATION: 6
<223> OTHER INFORMATION: Xaa is Lys, Glu, Ser or Arg
<220> FEATURE:
<221> NAME/KEY: SITE
<222> LOCATION: 8
<223> OTHER INFORMATION: Xaa is Val or Ile

<400> SEQUENCE: 84

Xaa Asp Pro Xaa Xaa Xaa Trp Xaa Gln
 1               5

<210> SEQ ID NO 85
<211> LENGTH: 10
<212> TYPE: PRT
<213> ORGANISM: Artificial Sequence
<220> FEATURE:
<223> OTHER INFORMATION: A chemokine variant

<400> SEQUENCE: 85

Cys Leu Asp Pro Lys Gln Lys Trp Ile Gln
 1               5                  10
```

COMPOUNDS AND METHODS TO INHIBIT OR AUGMENT AN INFLAMMATORY RESPONSE

BACKGROUND OF THE INVENTION

Macrophage/monocyte recruitment plays a role in the morbidity and mortality of a broad spectrum of diseases, including autoimmune diseases, granulomatous diseases, allergic diseases, infectious diseases, osteoporosis and coronary artery disease. For example, in atherosclerosis early during lipid lesion formation, circulating monocytes adhere to the activated endothelium overlying the incipient plaque. Under appropriate conditions, the monocytes then migrate into the developing intima. In the intima, macrophage accumulate lipoprotein and excrete an excess of proteases relative to protease inhibitors. If the lipoproteins are oxidized, they are toxic to macrophage, which results in macrophage cell death and an increase in an unstable, necrotic, extracellular lipid pool. An excess of proteases results in loss of extracellular matrix and destabilization of the fibrous plaque. Plaque instability is the acute cause of myocardial infarction.

Many molecules have been identified that are necessary for the recruitment of monocytes and other inflammatory cell types. These molecules represent targets for the inhibition of monocyte recruitment. One class of such molecules is adhesion molecules, e.g., receptors, for monocytes. Another class of molecules includes inflammatory mediators, such as TNF-A and related molecules, the interleukins, e.g., IL-1β, and chemokines, e.g., monocyte chemoattractant protein-1 (MCP-1).

As a result, agents which modulate the activity of chemokines are likely to be useful to prevent and treat a wide range of diseases. For example, Rollins et al. (U.S. Pat. No. 5,459,128) generally disclose analogs of MCP-1 that inhibit the monocyte chemoattractant activity of endogenous MCP-1. Analogs that are effective to inhibit endogenous MCP-1 are disclosed as analogs which are modified at 28-tyrosine, 24-arginine, 3-aspartate and/or in amino acids between residues 2–8 of MCP-1. In particular, Rollins et al. state that "[s]uccessful inhibition of the activity is found where MCP-1 is modified in one or more of the following ways: a) the 28-tyrosine is substituted by aspartate, b) the 24-arginine is substituted by phenylalanine, c) the 3-aspartate is substituted by alanine, and/or d) the 2–8 amino acid sequence is deleted" (col. 1, lines 49–54). The deletion of amino acids 2–8 of MCP-1 ("MCP-1(Δ2–8)") results in a polypeptide that is inactive, i.e., MCP-1 (Δ2–8) is not a chemoattractant (col. 5, lines 22–23). The only effective MCP-1 inhibitor disclosed in Rollins et al. is MCP-1 (Δ2–8).

Recent studies suggest that MCP-1(Δ2–8) exhibits a dominant negative effect, i.e., it forms heterodimers with wild-type MCP-1 that cannot elicit a biological effect (Zhang et al., *J. Biol. Chem.*, 269, 15918 (1994); Zhang et al., *Mol. Cell. Biol.*, 15, 4851 (1995)). Thus, MCP-1 (Δ2–8) does not exhibit properties of a classic receptor antagonist. Moreover, MCP-1 (Δ2–8) is unlikely to be widely useful for inhibition of MCP-1 activity in vivo, as MCP-1(Δ2–8) is a large polypeptide with undesirable pharmacodynamic properties. Furthermore, it is unknown whether MCP-1 (Δ2–8) is active as a dominant-negative inhibitor of other chemokines associated with inflammation.

Thus, there is a need to identify agents that inhibit chemokine-induced macrophage and/or monocyte recruitment which have desirable pharmacodynamic properties.

SUMMARY OF THE INVENTION

The invention provides a therapeutic agent comprising an isolated and purified chemokine peptide, chemokine peptide variant, chemokine analog, or a derivative thereof. Preferably, the therapeutic agent of the invention inhibits the activity of more than one chemokine, although the agent may not inhibit the activity of all chemokines to the same extent. Alternatively, a preferred therapeutic agent of the invention specifically inhibits the activity of one chemokine to a greater extent than other chemokines. Yet another preferred therapeutic agent of the invention mimics the activity of a chemokine, e.g., it acts as an agonist. Thus, therapeutic agents that are chemokine antagonists and agonists are within the scope of the invention. A further preferred therapeutic agent of the invention is an agent that does not inhibit or mimic the activity of a chemokine but binds to or near the receptor for that chemokine, i.e., it is a neutral agent.

A preferred embodiment of the invention is an isolated and purified CC chemokine peptide 3, e.g., a peptide derived from MCP-1 which corresponds to about residue 46 to about residue 67 of mature MCP-1 ("peptide 3[MCP-1]"), a variant, an analog, or a derivative thereof. It is contemplated that chemokine peptide 3, a variant, an analog or a derivative thereof is a chemokine receptor antagonist, although these therapeutic agents may exert their effect by a different mechanism, or by more than one mechanism.

A preferred peptide 3 of the invention is a compound of formula (I):

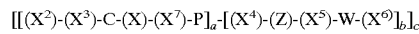

wherein $X^2$ is E, Q, D, N, L, P, I or M, wherein $X^3$ is I, V, M, A, P, norleucine or L, wherein X is A, L, V, M, P, norleucine or I, wherein $X^4$ is K, S, R, R, Q, N or T, wherein Z is Q, K, E, N, R, I, V, M, A, P, norleucine or L, wherein $X^7$ is D or P, wherein $X^5$ is K, E, R, S, Q, D, T, H or N, wherein $X^1$ is V, L, M, P, A, norleucine, or I, wherein $X^6$ is Q, N, K or R, wherein a is 0–6, wherein b is 0–6, and wherein c is 1–6, with the proviso that a and b cannot both be 0. The letters in formulas (I)–(III) that are not X, Y or Z represent peptidyl residues as shown in Table 2, hereinbelow. A more preferred peptide 3 of the invention is a compound of formula (I):

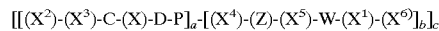

wherein $X^2$ is E, Q or M, wherein $X^3$ is I, V or L, wherein X is A, L or I, wherein $X^4$ is K, S or T, wherein Z is Q, K, E or L, wherein $X^5$ is K, E, R, S or T, wherein $X^1$ is V or I, wherein $X^6$ is Q or R, wherein a is 0–6, wherein b is 0–6, and wherein c is 1–6, with the proviso that a and b cannot both be 0.

Yet another preferred peptide 3 of the invention is a compound of formula (II):

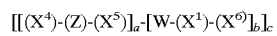

wherein $X^4$ is K, S or T, wherein Z is Q, K, E or L, wherein $X^5$ is K, E, R, S or T, wherein $X^1$ is V or I, wherein $X^6$ is Q or R, wherein a is 0–6, wherein b is 0–6, and wherein c is 1–6, with the proviso that a and b cannot both be 0.

Another preferred peptide 3 of the invention is a compound of formula (II):

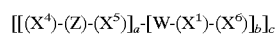

wherein $X^4$ is K, S, R, R, Q, N or T, wherein Z is Q, K, E, N, R, I, V, M, A, P, norleucine or L, wherein $X^5$ is K, E, R, S, Q, D, T, H or N, wherein $X^1$ is V, L, M, P, A, norleucine, or I, wherein $X^6$ is Q, N, K or R, wherein a is 0–6, wherein b is 0–6, and wherein c is 1–6, with the proviso that a and b cannot both be 0.

A preferred embodiment of the invention is an isolated and purified CC chemokine peptide 3, e.g., a peptide derived from MCP-1 which corresponds to SEQ ID NO:1 ("peptide 3(1–12)[MCP-1]"), a variant, an analog, or a derivative thereof. As described hereinbelow, peptide 3(1–12)[MCP-1](SEQ ID NO:1) is a pan-chemokine inhibitor, is bioavailable, and has desirable pharmacokinetics. Another preferred CC chemokine peptide 3 of the invention is peptide 3[MIP1α], and more preferably peptide 3(1–12)[MIP1α] which has an amino acid sequence corresponding to SEQ ID NO:42, a variant, an analog, a subunit or a derivative thereof.

Further preferred embodiments of the invention are a CC chemokine peptide 3 such as peptide 3(1–12)[MCP-4] (e.g., SEQ ID NO:65), peptide 3(1–12)[MCP-3](e.g., SEQ ID NO:66), peptide 3(1–12)[MCP-2] (e.g., SEQ ID NO:67), peptide 3(1–12)[eotaxin] (e.g., SEQ ID NO:68), peptide 3(1–12)[MIP1α],(e.g., SEQ ID NO:42), peptide 3(1–12)[MIP1β] (e.g., SEQ ID NO:43), peptide 3(1–12)[RANTES] (e.g., SEQ ID NO:44), or subunits thereof.

Another preferred embodiment of the invention includes a CXC chemokine peptide 3, a variant, an analog or a derivative thereof. A preferred CXC peptide 3 of the invention is a compound of formula (III):

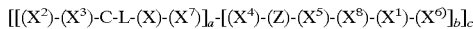

$$[[(X^2)\text{-}(X^3)\text{-}C\text{-}L\text{-}(X)\text{-}(X^7)]_a\text{-}[(X^4)\text{-}(Z)\text{-}(X^5)\text{-}(X^8)\text{-}(X^1)\text{-}(X^6)]_b]_c$$

wherein $X^2$ is E or K, wherein $X^3$ is I, A, R or L, wherein X is D or N, wherein $X^7$ is Q, P or L, wherein $X^4$ is E, K, D, A or Q, wherein Z is A, R, S or E, wherein $X^5$ is P, N or K, wherein $X^8$ is F, W, R, I, M, L or A, wherein $X^1$ is L, V, Y or I, wherein $X^6$ is K or Q, wherein a is 0–6, wherein b is 0–6, and wherein c is 1–6, with the proviso that a and b cannot both be 0.

Further preferred embodiments of the invention are a CXC chemokine peptide 3 such as peptide 3(1–12)[IL8] (e.g., SEQ ID NO:40), peptide 3(1–12)[SDF-1](e.g., SEQ ID NO:38), peptide 3(1–12)[ENA-78](e.g., SEQ ID NO:41), peptide 3(1–12)[GROα](e.g., SEQ ID NO:72), peptide 3(1–12)[GROβ](e.g., SEQ ID NO:73), peptide 3(1–12)[GROγ](e.g., SEQ ID NO:74), or subunits thereof.

Another preferred embodiment of the invention includes a chemokine peptide 3 that is at least a tripeptide, a variant thereof or a derivative thereof. A preferred embodiment of the invention is the MCP-1 tripeptide KQK (i.e., peptide 3(9–12)[MCP-1], which specifically inhibits MCP-1, but not MIP1α, IL8 and SDF1α, chemokine-induced activity. Other preferred embodiments of the invention include isolated and purified chemokine tripeptides that specifically inhibit IL8, MIP1α, SDF1, murine MCP-1, MCP-2, MCP-3, and MIP1β, e.g., KEN, SEE, KLK, KKE, KER, TQK, and SES, respectively. A further preferred embodiment of the invention is a chemokine peptide 3 tripeptide that inhibits the activity of more than one chemokine, e.g., WVQ or WIQ.

Another preferred embodiment of the invention is an isolated and purified CC chemokine peptide 2, such as a peptide corresponding to SEQ ID NO:3 ("peptide 2(1–15)[MCP-1]"), SEQ ID NO:5 ("peptide 2(1–14)[MIP1α]"), a variant, a subunit, an analog, or a derivative thereof. It is contemplated that chemokine peptide 2, a variant, an analog or a derivative thereof is a chemokine receptor agonist, although these therapeutic agents may exert their effect by a different mechanism, or by more than one mechanism.

Other preferred CC chemokine peptides 2 include peptide 2(1–14)[MIP1β] (e.g., SEQ ID NO:60), peptide 2(1–15) [RANTES] (e.g., SEQ ID NO:61), peptide 2(1–15)[MCP-2] (e.g., SEQ ID NO:62), peptide 2(1–15)[MCP-3](e.g., SEQ ID NO:63), peptide 2(1–15)[MCP-4] (e.g., SEQ ID NO:64), peptide 2(1–15)[eotaxin] (e.g., SEQ ID NO:75), or subunits thereof.

Another preferred embodiment of the invention includes a CXC chemokine peptide 2, a variant, an analog or a derivative thereof. Preferred CC chemokine peptide 2 includes peptide 2(1–15)[IL8] (e.g., SEQ ID NO:6), peptide 2(1–15)[SDF1] (e.g., SEQ ID NO:4), peptide 2(1–15) [ENA78] (e.g., SEQ ID NO:59), peptide 2(1–15)[GROα] (e.g., SEQ ID NO:69), peptide 2(1–15)[GROβ](e.g., SEQ ID NO:70), peptide 2(1–15)[GROγ] (e.g., SEQ ID NO:71), or a subunit thereof.

Also provided is an isolated and purified chemokine peptide variant, or a derivative thereof. A chemokine peptide variant has at least about 50%, preferably at least about 80%, and more preferably at least about 90% but less than 100%, amino acid sequence homology or identity to the amino acid sequence of the corresponding native chemokine, e.g., $Ser_7$ peptide 3(1–12)[MCP1] (SEQ ID NO: 11) has less than 100% homology to the corresponding amino acid sequence of MCP-1, i.e., a peptide having SEQ ID NO: 1. A preferred peptide 3 variant is $leu_4 ile_{11}$peptide 3(3–12)[MCP-1] (SEQ ID NO:27).

The invention also provides derivatives of chemokine peptides and peptide variants. A preferred derivative is a cyclic reverse sequence derivative (CRD) of a chemokine peptide or variant of the invention. For example, CRD-$Cys_{13}leu_4ile_{11}$peptide 3[MCP-1](3–12)[MCP-1] is a derivative of chemokine peptide 3 that is particularly useful in the practice of the methods of the invention.

Also provided are certain analogs of chemokines. In particular, analogs of chemokine peptide 2, chemokine peptide 3, or variants thereof are contemplated. A preferred analog of chemokine peptide 3 is an analog of WIQ. Thus, a preferred chemokine analog of the invention includes a compound of formula (IV):

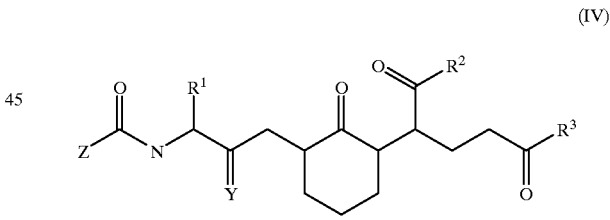

(IV)

wherein $R^1$ is aryl, heteroaryl, aryl($C_1$–$C_3$)alkyl, heteroaryl($C_1$–$C_3$)alkyl, coumaryl, coumaryl($C_1$–$C_3$) alkyl, chromanyl or chromanyl($C_1$–$C_3$)alkyl; wherein any aryl or heteroaryl group, or the benz-ring of any coumaryl or chromanyl group may optionally be substituted with one, two or three substituents selected from the group consisting of halo, nitro, cyano, hydroxy, ($C_1$–$C_6$)alkyl, ($C_1$–$C_6$)alkoxy, ($C_1$–$C_6$) alkanoyl, ($C_2$–$C_6$)alkanoyloxy, -C(=O)($C_1$–$C_6$) alkoxy, C(=O)NR$^g$R$^h$, NR$^i$R$^j$;

wherein $R^2$ is ($C_1$–$C_{10}$)alkyl, ($C_3$–$C_6$)cycloalkyl, ($C_3$–$C_6$) cycloalkyl($C_1$–$C_6$)alkyl, ($C_1$–$C_{10}$)alkoxy, ($C_3$–$C_6$) cycloalkyl($C_1$–$C_6$)alkoxy or N(R$^a$)(R$^b$);

wherein $R^3$ is ($C_1$–$C_{10}$)alkyl, ($C_3$–$C_6$)cycloalkyl, ($C_3$–$C_6$) cycloalkyl($C_1$–$C_6$)alkyl, ($C_1$–$C_{10}$)alkoxy, ($C_3$–$C_6$) cycloalkyl($C_1$–$C_6$)alkoxy or wherein Y is oxo or thioxo;
wherein Z is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy or $N(R^e)(R^f)$; and
wherein $R^a$-$R^j$ are each independently hydrogen, $(C_1-C_{10})$alkyl, $(C_1-C_{10})$alkanoyl, phenyl, benzyl, or phenethyl; or $R^a$ and $R^b$, $R^c$ and $R^d$, $R^e$ and $R^f$, $R^g$ and $R^h$, or $R^i$ and $R^j$ together with the nitrogen to which they are attached form a ring selected from pyrrolidino, piperidino, or morpholino; or a pharmaceutically acceptable salt thereof.

A preferred embodiment of a compound of formula (IV) includes a compound of a formula (IV) wherein $R^1$ is aryl, heteroaryl, coumaryl, or chromanyl. Preferably aryl is phenyl; and heteroaryl is indolyl or pyridinyl. Another preferred embodiment of a compound of formula (IV) includes a compound of a formula (IV) wherein $R^2$ is $N(R^a)(R^b)$; and $R^3$ is $N(R^c)(R^d)$. Yet another preferred embodiment of a compound of formula (IV) includes a compound of a formula (IV) wherein Z is $(C_1-C_{10})$alkyl.

A further preferred compound is a compound of formula (IV) wherein $R^1$ is indolyl; $R^2$ is $N(R^a)(R^b)$; $R^3$ is $N(R^c)(R^d)$; Y is S; Z is hydrogen; and $R^a$, $R^b$, $R^c$, and $R^d$ are each methyl.

Another preferred analog of chemokine peptide 3 is an analog of KQK (SEQ ID NO:51). Thus, the invention includes a compound of formula (V):

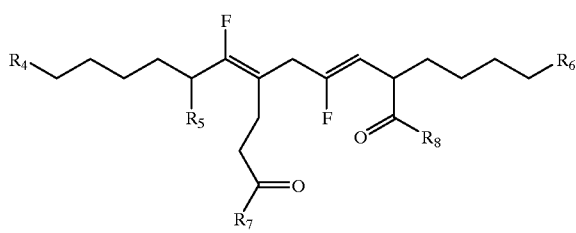

(V)

wherein $R^4$ is $NR_kR_l$;
wherein $R^5$ is $NR_mR_n$;
wherein $R^6$ is $NR_oR_p$;
wherein $R^7$ is $NR_qR_r$;
wherein $R^8$ is hydrogen, hydroxy, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, $NR_sR_t$, the amino terminus of an amino acid or the N-terminal residue of a peptide of 2 to about 25 amino acid residues;
wherein $R_k$, $R_l$, $R_o$, and $R_p$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkanoyl, phenyl, benzyl or phenethyl;
wherein $R_m$ are $R_n$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_1-C_{10})$alkanoyl, $(C_1-C_{10})$alkoxycarbonyl, 9-fluorenylmethoxycarbonyl, phenyl, benzyl, phenethyl, the C-terminal residue of an amino acid or a peptide of 2 to about 25 amino acid residues;
wherein $R_q$ are $R_r$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl;
wherein $R_s$ are $R_t$ are each independently hydrogen, $(C_1-C_{10})$alkyl, $(C_3-C_6)$cycloalkyl, $(C_3-C_6)$cycloalkyl $(C_1-C_6)$alkyl, phenyl, benzyl or phenethyl; or a pharmaceutically acceptable salt thereof.

Preferably $R_k$, $R_l$, $R_o$, and $R_p$ are each hydrogen; $R_m$ are $R_n$ are each independently hydrogen, acetyl, $(C_1-C_{10})$alkyl, $(C_3-C_6)$cycloalkyl, propoxy, butoxy, tert-butoxycarbonyl, 9-fluorenylmethoxycarbonyl or the C-terminal residue of an amino acid or a peptide of 2 to about 25 amino acid residues; and $R_q$ are $R_r$ are each independently hydrogen, $(C_1-C_{10})$alkyl, or $(C_3-C_6)$cycloalkyl.

Further provided are isolated and purified nucleic acid molecules, e.g., DNA molecules, comprising a preselected nucleic acid segment which encodes at least a portion of a chemokine, i.e., they encode a chemokine peptide or a variant thereof. For example, the invention provides an expression cassette comprising a preselected DNA segment which codes for an RNA molecule which is substantially identical (sense) to all or a portion of a messenger RNA ("target" mRNA), i.e., an endogenous or "native" chemokine mRNA. The preselected DNA segment in the expression cassette is operably linked to a promoter. As used herein, "substantially identical" in sequence means that two nucleic acid sequences have at least about 65%, preferably about 70%, more preferably about 90%, and even more preferably about 98%, sequence identity to each other.

The present invention also provides isolated and purified DNA molecules which provide "anti-sense" mRNA transcripts of the DNA segments that encode a chemokine which, when expressed from an expression cassette in a host cell, can alter chemokine expression. As used herein, the term "antisense" means a sequence of nucleic acid which is the reverse complement of at least a portion of a RNA molecule that codes for a chemokine. Preferably, the antisense sequences of the invention are substantially complementary to a DNA segment encoding a peptide or peptide variant of the invention. As used herein, "substantially complementary" means that two nucleic acid sequences have at least about 65%, preferably about 70%, more preferably about 90%, and even more preferably about 98%, sequence complementarity to each other. A substantially complementary RNA molecule is one that has sufficient sequence complementarity to the mRNA encoding a chemokine so as to result in a reduction or inhibition of the translation of the mRNA. It is envisioned that the duplex formed by the antisense sequence and the mRNA inhibits translation of the mRNA, as well as promotes RNA degradation, although anti-sense sequences may exert their effect by other mechanisms, or by a combination of mechanisms.

The introduction of chemokine sense or antisense nucleic acid into a cell ex vivo or in vivo can result in a molecular genetic-based therapy directed to controlling the expression of the chemokine. Thus, the introduced nucleic acid may be useful to correct or supplement the expression of the gene in patients with a chemokine-associated indication. For example, the administration of an expression vector encoding a peptide of the invention which is a chemokine receptor agonist may increase the chemokine signaling and thus be efficacious for diseases which are characterized by decreased levels of the chemokine. Likewise, the administration of an expression vector comprising antisense chemokine sequences may be useful to prevent or treat a disorder associated with increased chemokine expression. For example, an expression vector containing antisense peptide 3(1–12)[MCP-1] which is introduced into the lungs may be efficacious to prevent or treat asthma.

Also provided are pharmaceutical compositions, delivery systems, and kits comprising the therapeutic agents of the invention.

The invention also provides methods to treat chemokine-associated indications. For example, the invention provides a method of preventing or inhibiting an indication associated with chemokine-induced activity. The method comprises administering to a mammal afflicted with, or at risk of, the indication an amount of a chemokine peptide 3, a subunit thereof, a variant thereof, a derivative thereof, a compound of formula (IV), a compound of formula (V), or a combination thereof, effective to prevent or inhibit said activity. Preferably, the peptide is not an IL-8 peptide 3. Preferably, the administration is effective to inhibit the activity of more than one chemokine. Preferred pan-chemokine inhibitors are WVQ (SEQ ID NO:33), WIQ (SEQ ID NO:34), leu$_4$ile$_{11}$peptide 3 (3–12)[MCP-1], leu$_4$ile$_{11}$peptide 3 (1–12) [MCP-1] and CRD-Cys$_{13}$leu$_4$ile$_{11}$peptide 3 (3–12). These agents are useful to treat indications such as multiple sclerosis and autoimmune disorders.

The invention also provides a method of treating a mammal afflicted with, or at risk of, an indication associated with chemokine-induced activity, comprising: administering to the mammal an effective amount of a compound of formula (IV):

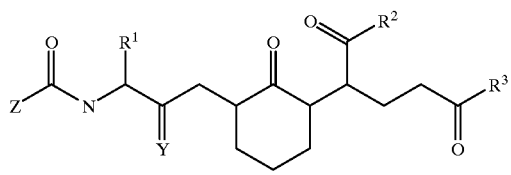

wherein $R^1$ is aryl, heteroaryl, coumaryl or chromanyl; wherein $R^2$ is $N(R^a)(R^b)$; wherein $R^3$ is $N(R^c)(R^d)$; wherein Y is oxo or thioxo; wherein Z is $(C_1-C_{10})$alkyl; wherein $R^a$-$R^d$ are each independently hydrogen, $(C_1-C_{10})$alkyl, $(C_1-C_{10})$alkanoyl, phenyl, benzyl or phenethyl; or wherein $R^a$ and $R^b$, or $R^c$ and $R^d$, together with the nitrogen to which they are attached form a pyrrolidino, piperidino or morpholino ring; or a pharmaceutically acceptable salt thereof.

Further provided is a method of treating a mammal afflicted with, or at risk of, an indication associated with chemokine-induced activity, comprising: administering to the mammal an effective amount of a compound of formula (V):

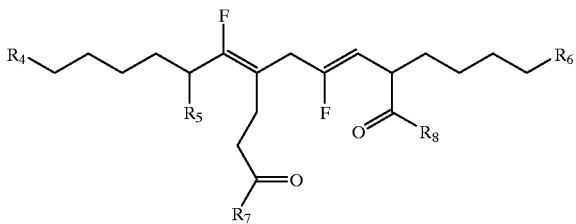

wherein $R^4$ is $NR_kR_l$; wherein $R^5$ is $NR_mR_n$; wherein $R^6$ is $NR_oP_p$; wherein $R^7$ is $NR_qR_r$; wherein $R^8$ is hydrogen, hydroxy, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, $NR_sR_t$, the N-terminal residue of an amino acid or a peptide of 2 to about 25 amino acid residues; wherein $R_k$, $R_l$, $R_o$, and $R_p$ are each hydrogen; wherein $R_m$ are $R_n$ are each independently hydrogen, acetyl, $(C_1-C_{10})$alkyl, $(C_3-C_6)$cycloalkyl, propoxy, butoxy, tert-butoxycarbonyl, 9-fluorenylmethoxycarbonyl or the C-terminal residue of an amino acid or a peptide of 2 to about 25 amino acid residues; wherein $R_q$ and $R_r$ are each independently hydrogen, $(C_1-C_{10})$alkyl, or $(C_3-C_6)$ cycloalkyl; and wherein $R_s$ are $R_t$ are each independently hydrogen, $(C_1-C_{10})$alkyl, $(C_3-C_6)$cycloalkyl, $(C_3-C_6)$ cycloalkyl$(C_1-C_6)$alkyl, phenyl, benzyl, or phenethyl; or a pharmaceutically acceptable salt thereof.

The invention further provides a method to increase, augment or enhance a chemokine-associated inflammatory response in a mammal, comprising: administering to the mammal an amount of a chemokine peptide 2, a variant thereof, a derivative thereof, or a combination thereof, effective to increase, augment or enhance said response. These therapeutic agents are useful to increase an inflammatory response to, for example, intracellular pathogens or parasites, which often are associated with a poor immune response. Thus, these agents may be useful to treat or prevent tuberculosis and malaria. Therefore, the invention also provides a therapeutic method to prevent or treat parasitic infection.

The invention also provides a method of preventing or inhibiting an indication associated with histamine release from basophils or mast cells. The method comprises administering to a mammal at risk of, or afflicted with, the indication an effective amount of a chemokine peptide 3, a variant thereof, a derivative thereof, a compound of formula (IV), a compound of formula (V), or a combination thereof.

Also provided is a method of preventing or inhibiting an indication associated with monocyte or macrophage recruitment. The method comprises administering an effective amount of a chemokine peptide 3, a variant thereof, a derivative thereof, a compound of formula (IV), a compound of formula (V), or a combination thereof. For example, a chemokine peptide 3, a variant thereof, a derivative thereof may be useful to prevent or treat vascular or granulomatous indications.

Further provided is a therapeutic method to prevent or treat vascular indications, comprising: administering to a mammal in need of such therapy an effective amount of a chemokine peptide 3, a variant thereof, a derivative thereof, a compound of formula (IV), a compound of formula (V), or a combination thereof, wherein the indication is coronary artery disease, myocardial infarction, unstable angina pectoris, atherosclerosis or vasculitis.

The invention also provides a method to prevent or treat an autoimmune disorder. The method comprises administering to a mammal in need of said therapy an effective amount of a chemokine peptide 3, a variant thereof, a derivative thereof, a compound of formula (IV), a compound of formula (V), or a combination thereof. A preferred variant of peptide 3 useful to prevent or treat autoimmune disorders is leu$_4$ile$_{11}$peptide 3(1–12)[MCP-1] (SEQ ID NO:14) WVQ. A preferred chemokine peptide 3 for use in preventing or treating multiple sclerosis includes SEE (SEQ ID NO:27) and peptide 3(1–14)[MIP1α] (SEQ ID NO:42).

Further provided is a method to modulate the chemokine-induced activity of a macrophage at a preselected physiological site. The method comprises administering a dosage form comprising an effective amount of a chemokine peptide 3, a variant thereof, a derivative thereof, a compound of formula (IV), a compound of formula (V), or a combination thereof, wherein the dosage form is linked, either covalently or noncovalently, to a targeting moiety. The targeting moiety binds to a cellular component at the preselected physiological site.

Also provided is a therapeutic method to augment an immune response. The method comprises administering to a mammal an immunogenic moiety and an amount of a chemokine peptide 2, a variant thereof, a derivative thereof, a compound of formula (IV), a compound of formula (V), or a combination thereof, wherein the amount is effective to augment the immune response of the mammal to the immunogenic moiety. Thus, the invention also provides a vaccine comprising an immunogenic moiety and an amount of a chemokine peptide 2, a variant thereof or a derivative thereof, a compound of formula (IV), a compound of formula (V), or a combination thereof. As used herein, an "immunogenic moiety" means an isolated or purified composition or compound (e.g., a purified virus preparation or a native or recombinant viral or bacterial antigen) that, when introduced into an animal, preferably a mammal, results in a humoral and/or cellular immune response by the animal to the composition or compound.

Further provided is a therapeutic method to prevent or inhibit lentiviral infection or replication. The method comprises administering to a mammal in need of such therapy an effective amount of a chemokine peptide 2, a variant thereof, a derivative thereof, a compound of formula (IV), a compound of formula (V), or a combination thereof. Preferably, the therapeutic agents are employed to prevent or treat HIV infection. More preferably, the agent is administered before, during or after the administration of an anti-viral agent, e.g., AZT or a non-nucleoside RT-inhibitors.

A therapeutic method to prevent or treat low bone mineral density is also provided. The method comprises administering to a mammal in need of such therapy an effective amount of a chemokine peptide 3, a variant thereof, a derivative thereof, a compound of formula (IV), a compound of formula (V), or a combination thereof. A preferred derivative of a variant of peptide 3 to prevent or treat low mineral bone density is CRD-$Cys_{13}leu_4ile_{11}$peptide 3[MCP-1]. A preferred subunit of SEQ ID NO: 1 useful in preventing or treating low mineral bone density is KQK (SEQ ID NO:31).

Also provided is a method of suppressing tumor growth in a vertebrate animal comprising administering to said vertebrate a therapeutically effective amount of a chemokine peptide 3, a variant thereof, a derivative thereof, a compound of formula (IV), a compound of formula (V), or a combination thereof. Preferably, the method increases or enhances a macrophage-associated activity at a tumor site.

Further provided is a method for preventing or treating psoriasis in a mammal, comprising: administering to the mammal an effective amount of a chemokine peptide 3, a variant thereof, a derivative thereof, a compound of formula (IV), a compound of formula (V), or a combination thereof. A preferred derivative to prevent or treat psoriasis is a CRD derivative of peptide 3.

Further provided is a method to enhance wound healing. The method comprises administering an effective amount of a chemokine peptide 3, a variant thereof, a derivative thereof, a compound of formula (IV), a compound of formula (V), or a combination thereof.

The invention also provides methods in which the nucleic acid molecules of the invention are administered to a mammal afflicted with, or at risk of, an indication associated with a chemokine-induced activity.

DETAILED DESCRIPTION OF THE INVENTION

Definitions

Figure 1:
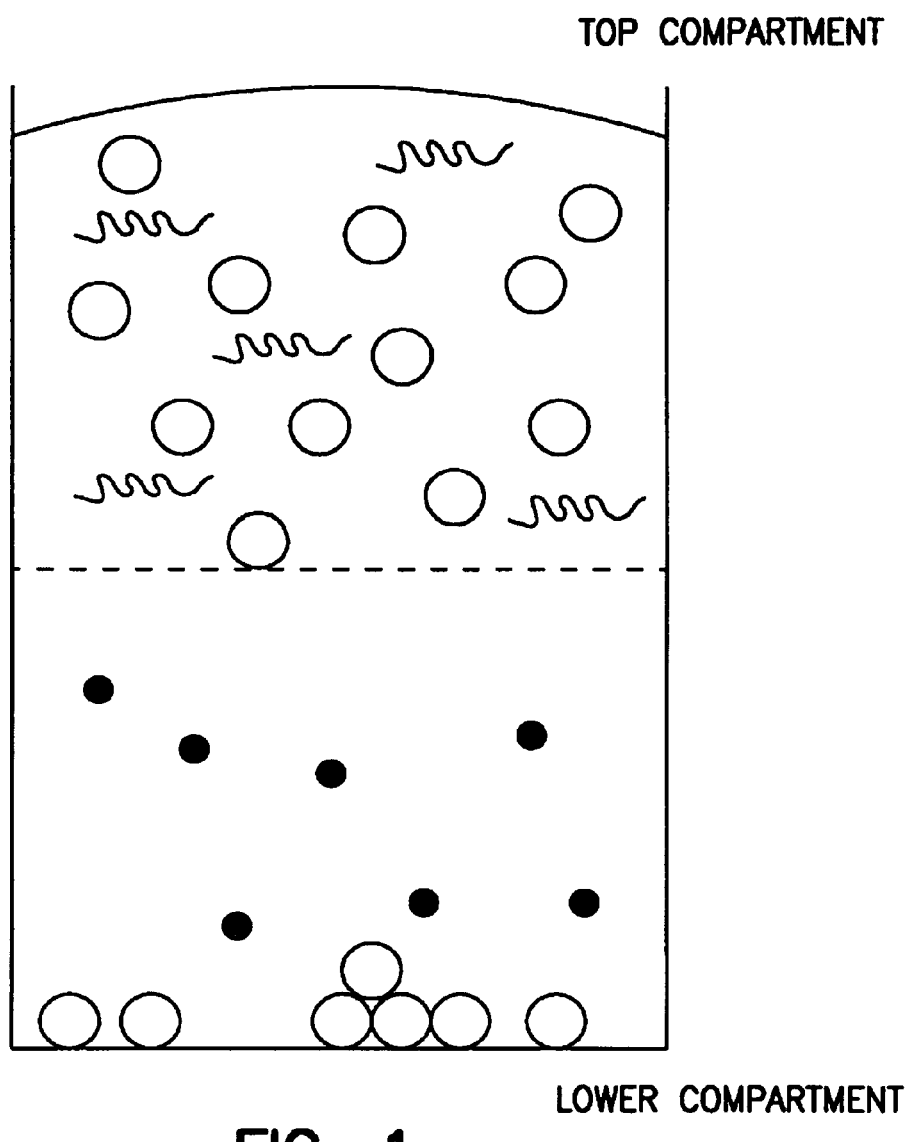
FIG. 1 is a schematic of the trans-well migration assay. In most experiments, the peptide (wavy line) is added to the upper well with about 50,000 cells (O). The upper and lower wells are separated by a 5 $\mu$m or 8 $\mu$m pore size PVP-free membrane (- - - -). Chemokine (●) is added to the lower well. After 4 hours, the number of cells that have migrated through the membrane are measured (O in lower well).

"Chemokines" refers to a family of proinflammatory signaling molecules. Chemokines include, but are not limited to, MCP-1 (SEQ ID NO:16), MCP-2 (SEQ ID NO: 17), MCP-3 (SEQ ID NO: 18), MIG (SEQ ID NO:45), MIP1$\alpha$ (SEQ ID NO:19), MIP1$\beta$ (SEQ ID NO:20), RANTES (SEQ ID NO:21), PF4 (SEQ ID NO:46), I-309 (SEQ ID NO:47), HCC-1 (SEQ ID NO:48), eotaxin (SEQ ID NO:25), C10 (SEQ ID NO:49), CCR-2 (SEQ ID NO:50), ENA-78 (SEQ ID NO:52), GRO$\alpha$ (SEQ ID NO:24), GRO$\beta$ (SEQ ID NO:53), IL-8 (SEQ ID NO:23), IP-10 (SEQ ID NO:54), SDF1$\alpha$ (SEQ ID NO:22), SDF1$\beta$ (SEQ ID NO:56), GRO$\alpha$ (SEQ ID NO:57), TARC, LARC, MIG, Ck$\beta$8, CCF18/MRP-2, and MIP1$\tau$. "CXC" or "$\alpha$" chemokines include, but are not limited to, IL-8, PF4, IP10, NAP-2, GRO$\alpha$, GRO$\beta$, GRO$\gamma$, SDF1, NAP-2 and ENA78. "CC" or "$\beta$" chemokines include, but are not limited to, MCP-1, MCP-2, MCP-3, MCP-4, RANTES, eotaxin, LARC, TARC, MIP1$\alpha$, MIP1$\beta$, 1309, HCC-1, CK$\beta$8, CCF18/MRP-2, and MIP1$\tau$.

"Peptide 3" refers to a peptide derived from a chemokine, which is generally located in the carboxy-terminal half of the chemokine, and which inhibits the activity of at least the corresponding native chemokine, as determined by methods well known to the art. Peptide 3 comprises no more than 30, preferably about 3 to about 25, more preferably about 3 to about 15, and even more preferably about 3 to about 10, peptidyl residues which have 100% amino acid sequence homology or identity to the amino acid sequence of the corresponding native chemokine. For example, a preferred peptide 3 of MCP-1 that inhibits at least the activity of MCP-1 is peptide 3(1–12)[MCP-1], e.g., a peptide which has an amino acid sequence corresponding to SEQ ID NO:1, or a subunit or derivative thereof. Another preferred embodiment of the invention is peptide 3(3–12)[MCP-1], more preferably a peptide 3(3–12)[MCP-1] which has an amino acid sequence corresponding to SEQ ID NO:7, or a subunit or derivative thereof.

An alignment of chemokine amino acid sequences, such as the alignment depicted in Table 3, provides a general method to identify the location of peptide 3 sequences in chemokines. Generally, peptide 3 in non-MCP-1 chemokines corresponds to about residue 46 to about residue 67 of mature human MCP-1. Moreover, it is envisioned that peptide 3 may comprise moieties other than the amino acid sequence which inhibits chemokine activity, e.g., amino acid residues not present in the native chemokine (i.e., a fusion protein), nucleic acid molecules or targeting moieties such as antibodies or fragments thereof or biotin, so long as these moieties do not substantially reduce the biological activity of peptide 3. A substantial reduction in activity means a reduction in activity of greater than about 99%.

"Peptide 2" refers to a peptide derived from a chemokine, which is generally located in the amino-terminal two-thirds of the chemokine, and which does not include the amino-terminal about 20 to about 24 amino acid residues of the native mature chemokine. Generally, peptide 2 is a chemokine agonist, but peptide 2 may also have neither agonist or antagonist activities (i.e., it is "neutral") so long as the peptide specifically binds to at least one chemokine receptor. Peptide 2 comprises no more than 30, preferably about 3 to about 25, more preferably about 10 to about 25, and even more preferably about 10 to about 16, peptidyl residues which have 100% amino acid sequence homology or identity to the amino acid sequence of the corresponding native chemokine. For example, a preferred peptide 2 of MCP-1 is peptide 2(1–15)[MCP-1], for example a peptide which has an amino acid sequence corresponding to SEQ ID NO:3, or a subunit or derivative thereof.

An alignment of chemokine amino acid sequences, such as the alignment depicted in Table 3, provides a general method to identify the location of peptide 2 sequences in other chemokines. Generally, peptide 2 in non-MCP-l chemokines corresponds to about residue 27 to about residue 45 on mature human MCP-1. It is also envisioned that peptide 2 may comprise moieties other than the amino acid sequence which mimics, enhances or does not affect (i.e., neutral) chemokine activity, e.g., amino acid residues not present in the native chemokine, nucleic acid molecules or targeting moieties such as those described above for peptide 3, so long as these moieties do not substantially alter the biological activity of peptide 2. A substantial alteration in activity means an alteration of greater than about 99%.

As used herein, the terms "isolated and/or purified" refer to in vitro preparation, isolation and/or purification of a therapeutic agent of the invention, so that it is not associated with in vivo substances.

An isolated "chemokine peptide variant" of peptide 3 or peptide 2 is a peptide comprising no more than 30, preferably about 3 to about 25, and more preferably about 3 to about 15, peptidyl residues which have at least 50%, preferably at least about 80%, and more preferably at least about 90% but less than 100%, amino acid sequence homology or identity to the amino acid sequence of the corresponding native chemokine, e.g., $Ser_7$ peptide 3(1–12)[MCP 1] (SEQ ID NO: 11) has less than 100% homology to the corresponding amino acid sequence of MCP-1, i.e., peptide 3(1–12)[MCP-1] (SEQ ID NO: 1). A variant of the invention may include amino acid residues not present in the corresponding native chemokine, and internal deletions relative to the corresponding native chemokine. Chemokine peptide variants include peptides having at least one D-amino acid.

Chemokine peptides or peptide variants which are subjected to chemical modifications, such as esterification, amidation, reduction, protection and the like, are referred to as chemokine "derivatives." For example, a modification known to improve the stability and bioavailability of peptides in vivo is the cyclization of the peptide, for example through one or more disulfide bonds. A preferred modification is the synthesis of a cyclic reverse sequence derivative (CRD) of a peptide of the invention. A linear peptide is synthesized with all D-form amino acids using the reverse (i.e., C-terminal to N-terminal) sequence of the peptide. If necessary, additional cysteine residues are added to the N and C termini (if the peptide sequence does not already have N and C terminal cys residues), thereby allowing oxidative cyclization. However, the term "CRD" includes cyclization by other mechanisms, e.g., via a peptidyl bond, and the like. A preferred derivative of the invention is CRD-$Cys_{13}leu_4ile_{11}$peptide 3[MCP-1].

Also included within the scope of the term "derivative" is linear reverse D (LRD) and cyclized forward L (CFL) derivatives. LRD derivatives have the reverse (i.e., C-terminal to N-terminal) sequence of the peptide with all D-form amino acids, but are not cyclized. CFL derivatives have the forward (i.e., N-terminal to C-terminal) sequence of the peptide with all L-form amino acids, but with additional N and C terminal cys residues (if the peptide sequence does not already have cys residues at either the N or the C terminal position), followed by oxidative cyclization, or cyclization by an alternative method.

A "chemokine analog" means a moiety that mimics or inhibits a chemokine-induced activity, or binds to or near a chemokine receptor but does not mimic or inhibit chemokine activity (neutral), wherein the portion of the moiety that mimics or inhibits the chemokine-induced activity, or binds to or near the receptor but is neutral, is not a peptide, and wherein the active portion of the analog is not a nucleic acid molecule. As used herein, the term "mimics" means that the moiety induces an activity that is induced by a native chemokine, but that the induction by the analog is not necessarily of the same magnitude as the induction of activity by the native chemokine. It is also envisioned that the chemokine analogs of the invention may comprise moieties other than the portion which inhibits or mimics chemokine activity, or binds to or near a chemokine receptor without eliciting or inhibiting signaling, e.g., peptide or polypeptide molecules, e.g., antibodies or fragments thereof or fusion proteins, nucleic acid molecules, sugars lipids, fats, small chemicals, metals, salts, synthetic polymers, e.g., polylactide and polyglycolide, surfactants and glycosaminoglycans, which preferably are covalently attached or linked to the portion of the analog that mimics or inhibits the chemokine-induced activity, so long as the other moieties do not alter the biological activity of the analog. Also envisioned is a chemokine analog that is non-covalently associated with peptide or polypeptide molecules, e.g., antibodies or fragments thereof or fusion proteins, nucleic acid molecules, sugars lipids, fats, small chemicals, metals, salts, synthetic polymers, e.g., polylactide and polyglycolide, surfactants and glycosaminoglycans.

A preferred chemokine analog of the invention is a compound of formula (IV):

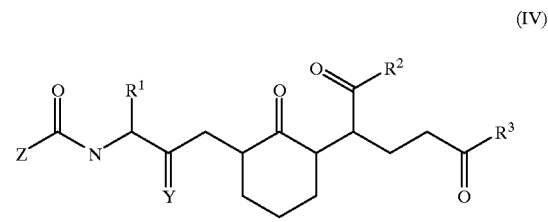

(IV)

wherein $R^1$ is aryl, heteroaryl, aryl($C_1$–$C_3$)alkyl, heteroaryl($C_1$–$C_3$)alkyl, coumaryl, coumaryl($C_1$–$C_3$) alkyl, chromanyl or chromanyl($C_1$–$C_3$)alkyl; wherein any aryl or heteroaryl group, or the benz-ring of any coumaryl or chromanyl group may optionally be substituted with one, two or three substituents selected from the group consisting of halo, nitro, cyano, hydroxy, ($C_1$–$C_6$)alkyl, ($C_1$–$C_6$)alkoxy, ($C_1$–$C_6$) alkanoyl, ($C_2$–$C_6$)alkanoyloxy, C(=O)($C_1$–$C_6$)alkoxy, C(=O)$NR^gR^h$, $NR^iR^j$;

wherein $R^2$ is ($C_1$–$C_{10}$)alkyl, ($C_3$–$C_6$)cycloalkyl, ($C_3$–$C_6$) cycloalkyl($C_1$–$C_6$)alkyl, ($C_1$–$C_{10}$)alkoxy, ($C_3$–$C_6$) cycloalkyl($C_1$–$C_6$)alkoxy or N($R^a$)($R^b$);

wherein $R^3$ is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy or $N(R^c)(R^d)$;

wherein Y is oxo or thioxo;

wherein Z is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy or $N(R^e)(R^f)$; and wherein $R^a$-$R^j$ are each independently hydrogen, $(C_1-C_{10})$alkyl, $(C_1-C_{10})$alkanoyl, phenyl, benzyl, or phenethyl; or $R^a$ and $R^b$, $R^c$ and $R^d$, $R^e$ and $R^f$, $R^g$ and $R^h$, or $R^i$ and $R^j$ together with the nitrogen to which they are attached form a ring selected from pyrrolidino, piperidino, or morpholino; or a pharmaceutically acceptable salt thereof.

A preferred embodiment of a compound of formula (IV) includes a compound of formula (IV) wherein $R^1$ is aryl, heteroaryl, coumaryl, or chromanyl. Preferably aryl is phenyl; and heteroaryl is indolyl or pyridinyl. Another preferred embodiment of a compound of formula (IV) includes a compound of a formula (IV) wherein $R^2$ is $N(R^a)(R^b)$; and $R^3$ is $N(R^c)(R^d)$. Yet another preferred embodiment of a compound of formula (IV) includes a compound of a formula (IV) wherein Z is $(C_1-C_{10})$alkyl.

A further preferred compound is a compound of formula (IV) wherein $R^1$ is indolyl; $R^2$ is $N(R^a)(R^b)$; $R^3$ is $N(R^c)(R^d)$; Y is S; Z is hydrogen; and $R^a$, $R^b$, $R^c$, and $R^d$ are each methyl.

Another preferred chemokine analog of the invention is a compound of formula (V):

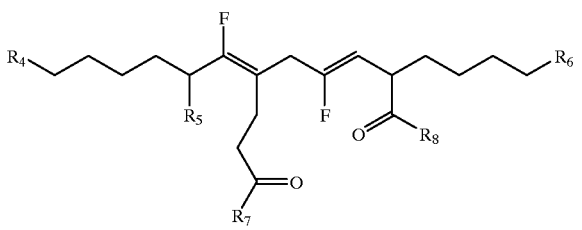

(V)

wherein $R^4$ is $NR_kR^l$;
wherein $R^5$ is $NR^mR^n$;
wherein $R^6$ is $NR_oR_p$;
wherein $R^7$ is $NR_qR^r$;
wherein $R^8$ is hydrogen, hydroxy, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, $NR_sR_t$, the amino terminus of an amino acid or the N-terminal residue of a peptide of 2 to about 25 amino acid residues;

wherein $R_k$, $R_l$, $R_o$, and $R_p$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkanoyl, phenyl, benzyl or phenethyl;

wherein $R_m$ are $R_n$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_1-C_{10})$alkanoyl, $(C_1-C_{10})$alkoxycarbonyl, 9-fluorenylmethoxycarbonyl, phenyl, benzyl, phenethyl, the C-terminal residue of an amino acid or a peptide of 2 to about 25 amino acid residues;

wherein $R_q$ are $R_r$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl;

wherein $R_s$ are $R_t$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; or a pharmaceutically acceptable salt thereof.

Preferably $R_k$, $R_l$, $R_o$, and $R_p$ are each hydrogen; $R_m$ are $R_n$ are each independently hydrogen, acetyl, $(C_1-C_{10})$alkyl, $(C_3-C_6)$cycloalkyl, propoxy, butoxy, tert-butoxycarbonyl, 9-fluorenylmethoxycarbonyl, the C-terminal residue of an amino acid or a peptide of 2 to about 25 amino acid residues; and $R_q$ are $R_r$ are each independently hydrogen, $(C_1-C_{10})$alkyl, or $(C_3-C_6)$cycloalkyl.

As used herein, halo is fluoro, chloro, bromo, or iodo. The terms alkyl and alkoxy denote both straight and branched groups, but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and $N(R^4)$ wherein $R^4$ is absent or is hydrogen, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of formula (IV) or (V) having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein. It is well known in the art how to prepare optically active forms (for example, by resolution of the racemic form by recrystallization techniques, by synthesis, from optically-active starting materials, by chiral synthesis, or by chromatographic separation using a chiral stationary phase). It is also well known to the art how to determine a compounds ability to inhibit chemokine-induced macrophage and/or monocyte recruitment activity using the standard tests described herein, or using other tests which are well known in the art.

Specific and preferred values listed herein for radicals, substituents, and ranges, are for illustration only and they do not exclude other defined values or other values within defined ranges for the radicals and substituents. Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; $(C_1-C_6)$alkyl can be methyl, ethyl, propyl, isopropyl, butyl, iso-butyl, sec-butyl, pentyl, 3-pentyl, or hexyl; $(C_1-C_3)$alkyl can be methyl, ethyl, or propyl; $(C_3-C_6)$cycloalkyl can be cyclopropyl, cyclobutyl, cyclopentyl, or cyclohexyl; $(C_1-C_{10})$alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy, or decyloxy; $(C_1-C_6)$alkoxy can be methoxy, ethoxy, propoxy, isopropoxy, butoxy, iso-butoxy, sec-butoxy, pentoxy, 3-pentoxy, or hexoxy; $(C_1-C_{10})$alkanoyl can be formyl, acetyl, propanoyl, butanoyl, pentanoyl, hexanoyl, heptanoyl, octanoyl, nonanoyl, or decanoyl; $(C_1-C_6)$alkanoyl can be formyl, acetyl, propanoyl, butanoyl, pentanoyl, or hexanoyl; $(C_2-C_6)$alkanoyloxy can be acetoxy, propanoyloxy, butanoyloxy, pentanoyloxy, or hexanoyloxy; aryl can be phenyl, indenyl, or naphthyl; and heteroaryl can be furyl, imidazolyl, tetrazolyl, pyridyl, (or its N-oxide), thienyl, pyrimidinyl (or its N-oxide), indolyl, or quinolyl (or its N-oxide).

Preferably, the therapeutic agents of the invention are biologically active. The biological activity of a chemokine peptide, peptide variant, analog or derivative thereof, can be measured by methods known to the art, some of which are described hereinbelow. For example, biologically active peptide 3[MCP-1] variants falling within the scope of the invention have at least about 1%, preferably at least about 10%, more preferably at least about 50%, and even more preferably at least about 90%, the activity of the corresponding native peptide sequence, e.g., peptide 3(1–12)[MCP-1] (SEQ ID NO:1), or the native chemokine, e.g., MCP-1 (SEQ ID NO:16). Thus, a peptide 3 variant, e.g., leu$_4$ile$_{11}$peptide 3(1–12)[MCP-1](SEQ ID NO:1), falling within the scope of the invention has an ED$_{50}$ for inhibition that is at least about 1%, preferably at least about 10%, more preferably at least about 50%, and even more preferably at least about 90%, the maximal activity of peptide 3(1–12)[MCP-1] (SEQ ID NO:1) at 100 µM.

Similarly, for example, peptide 2[MCP-1], variants, analogs or derivatives falling within the scope of the invention have an ED$_{50}$ for a chemokine-like activity which is at least about 1%, preferably at least about 10%, more preferably at least about 50%, and even more preferably at least about 90%, the maximal activity of SEQ ID NO:3 at 100 µM. Alternatively, peptide 2, variants, analogs or derivatives falling within the scope of the invention bind to cells having at least one chemokine receptor with an association constant that is at least about 1%, preferably at least about 10%, more preferably at least about 50%, and even more preferably at least about 90%, the affinity of peptide 2(1–15)[MCP-1] (SEQ ID NO:3) for the same receptor.

As used herein, "a chemokine-induced activity" includes, but is not limited to, an activity that is elicited through the binding of a chemokine, a therapeutic agent of the invention or other moiety, e.g., viral protein, to a chemokine receptor, or the binding of a therapeutic agent or other moiety in close physical proximity to the receptor so that the activity is altered. Chemokine receptors include, but are not limited to, CCR1, CCR2a, CCR2b, CCR3, CCR4, CCR5, IL8R1, IL8R2, CXCR1, CXCR2, CXCR3 and CXCR4.

As used herein, "indications associated with chemokine-induced activity" includes, but is not limited to, atherosclerosis and other forms of local or systemic vasculitis, diseases such as myocardial infarction and acute ischemia which are secondary to atherosclerosis; hypertension; reperfusion injury (Kumar et al., Circulation, 95, 693 (1997)); aortic aneurysms; stenosis or restenosis, particularly in patients undergoing angioplasty; pathologically low bone mineral density, such as osteoporosis; infection with human immunodeficiency virus (HIV), other lentiviruses or retroviruses with similar mechanisms of cell entry via chemokine receptor(s), or infection with other viruses, e.g., cytomegalovirus (Sozzani et al., J. Leukoc. Biol., 62, 30 (1997)); malaria and other consequences of infection by parasites related to plasmodium; autoimmune disorders, including, but not limited to, type I diabetes, Crohn's disease, multiple sclerosis, arthritis, rheumatoid arthritis (Ogata et al., J. Pathol., 182, 106 (1997); Gong et al., J. Exp. Med., 186, 131 (1997)) and systemic lupus erythematosus; as well as other disease states resulting from inappropriate inflammation, either local or systemic, for example, irritable or inflammatory bowel syndrome (Mazzucchelli et al., J. Pathol., 178, 201 (1996)), psoriasis (Gillitzer et al., Arch. Dermatol. Res., 284, 26 (1992); Yu et al., Lab Investig., 71, 226 (1994)), delayed type hypersensitivity, chronic pulmonary inflammation, gingival inflammation and osseous inflammation associated with lesions of endodontic origin (Volejnikova et al., Am. J. Pathol., 150, 1711 (1997)), hypersensitivity pneumonitis (Sugiyama et al., Eur. Respir. J., 8, 1084 (1995)), and inflammation related to histamine release from basophils (Dvorak et al., J. Allergy Clin. Immunol., 98, 355 (1996)), such as asthma, hay fever, histamine release from mast cells (Galli et al., Ciba Foundation Symposium, 147, 53(1989)), or mast cell tumors, types of type 1 hypersensitivity reactions (anaphylaxis, skin allergy, hives, allergic rhinitis, and allergic gastroenteritis); glomerulonephritis (Gesualdo et al., Kidney International, 51, 155 (1997)); and inflammation associated with peritoneal dialysis (Sach et al., Nephrol Dial. Transplant, 12, 315 (1997)).

Other indications falling within the scope of the invention include, but are not limited to, tumor growth; Kawasaki's disease; brain trauma (Ghimikar et al., J. Neurosci. Res., 46, 727 (1996)); strokes; pulmonary fibrosis; wound healing; bacterial infection, e.g., bacterial peritonitis; granulomatous diseases such as Mycobacteriosis, Pneumocystosis, Histoplasmosis, Blastomycosis, Coccidiomycosis, Cryptococcosis, Aspergillosis, granulomatous enteritis, Candidiasis, foreign body granulomas and peritonitis, pulmonary granulomatosis, Wegener's granulomatosis (Del Papa et al., Arthritis Rheum., 39, 758 (1996)), leprosy, syphilis, cat-scratch disease, schistosomiasis (Jacobs et al., Am. J. Pathol., 150, 2033 (1997)), silicosis, sarcoidosis (Iida et al., Thorax, 52, 431 (1997); Car et al., Am. J. Respir. Crit. Care Med., 149 655 (1994)) and berylliosis; lethal endotoxemia (Zisman et al., J. Clin. Invest., 99, 2832 (1997)); and indications associated with a weak inflammatory response, e.g., which occur in parasitic infection, e.g., Leishmaniasis Moll, trypanosome, Mycobacterium leprae or Mycobacterium tuberculosis infection.

In addition, to prevent or treat indications associated with a weak inflammatory response, the agents of the invention, i.e., peptide 2, its variants and derivatives, may be employed as vaccine adjuvants.

I. Identification of Therapeutic Agents Falling within the Scope of the Invention Agents useful in the practice of the invention include agents that inhibit or reduce (e.g., chemokine receptor antagonists), or increase, augment or enhance (e.g., chemokine receptor agonists), chemokine-induced activity, e.g., monocyte or macrophage recruitment. These agents can be identified by in vitro and in vivo assays, such as the assays described hereinbelow. It is recognized that not all agents falling within the scope of the invention can inhibit or enhance chemokine-induced activity in vitro and in vivo. The therapeutic agents of the invention may be direct receptor binding agonists and/or antagonists, or may act by a different mechanism, e.g., duplex formation of antisense nucleic acid with chemokine mRNA, or by more than one mechanism, so as to result in the alteration of chemokine-induced activity.

A. Peptides, Variants, Derivatives and Analogs
1. In vitro chemotaxis

To determine whether an agent inhibits a chemokine-induced activity, such as macrophage recruitment, varying amounts of the agent are mixed with cells in the presence of a known chemoattractant. For example, a range of known concentrations of an agent, e.g., a chemokine peptide, is incubated with a defined number (e.g., $10^4$–$10^6$) of human THP-1 monocyte cells in individual wells of the top compartment of a trans-well plate. Chemokine (such as MCP-1, MIP1α, IL8 or SDF-1α), at a concentration known to cause significant migration of THP-1 cells in the trans-well migration assay, is placed in the lower compartment (FIG. 1). Cells are then incubated at 37° C. for a period sufficient to allow migration, e.g., 4 hours. After incubation, the cells are gently removed from the top of the filter with a pipette, 20 µl of 20 mM EDTA in simple PBS is added into each top well, and incubated for 20 minutes at 4° C. The filter is carefully flushed with media using a gentle flow, and removed. A standard curve consisting of a two-fold dilution series of THP-1 cells (in 29 µl) is prepared to accurately quantify the number of cells that have migrated. Migrated cells are stained with 3 µl of MTT stock dye solution which is added directly into each well (5 mg/ml in RPMI-1640 without phenol red, Sigma Chemical Co.) and incubated at 37° C. for 4 hours. The media is carefully aspirated from each well, and the converted dye is solubilized by 20 µl of DMSO. Absorbance of converted dye is measured at a wavelength of 595 nm using an ELISA plate reader. The number of migrated cells in each well is then determined by interpolation of the standard curve (see also Imai et al., *J. Biol. Chem.*, 272, 15036 (1997)).

Any method suitable for counting cells can be used, for example, counting with a hemocytometer, incubation of the cells with MTT (see above), or FACS analysis. A negative control assay is also performed, using TGF-β or another non-chemokine chemoattractant (e.g., IL1β or TNFα). To assess whether the agent is cytotoxic, the same concentrations of agent are incubated with THP-1 cells. Agents which 1) are not cytotoxic at levels which inhibit migration, 2) are ineffective at inhibiting the negative control-induced migration, and 3) reduce or inhibit chemokine-induced THP-1 migration, are agents which fall within the scope of the invention.

Agents may also be screened in a chemotactic assay which employs human neutrophils, eosinophils, mast cells, basophils, platelets, lymphocytes or monocytes. For monocytes, 9 mls of fresh blood are transferred to a tube containing 1 ml of 3.8% sodium citrate, and left at room temperature for 15 minutes. Five mls of this anti-coagulated blood are carefully layered over 3.5 ml Polymorphprep® (Nycomed Pharma, Oslo), and centrifuged at 500 g for 35 minutes per the manufacturer's instructions. The top band at the sample/medium interface contains monocytes. The monocytes are carefully removed with a glass pipette, and reconstituted to the original volume (5 ml). The cells are washed with PBS plus 10% fetal calf serum, and centrifuged at 400 g for 10 minutes. The washing step is repeated three times before the cells are counted. Cells are resuspended at $1 \times 10^7$ cells/ml in RPMI-1640+10% fetal calf serum (FCS). The monocytes are cultured for two days at 37° C. in a humidified atmosphere of 5% $CO_2$.

On day 2, the cells are counted, spun down, and reconstituted to $1 \times 10^7$ cells/ml in Gey's balanced salt solution+1 mg/ml bovine serum albumin (BSA). Chemotaxis is induced in a 48 or 96-well disposable chemotaxis chamber fitted with a 5–8 µm polycarbonate filter for monocytes, neutrophils or eosinophils, or a 3 µm filter for lymphocytes (Uguccioni et al, *Eur. J. Immunol.*, 25, 64 (1995); Loetscher et al., *J. Exp. Med.*, 184, 569 (1996); Weber et al., *J. Immunol.*, 4166 (1995)) (PVP free, ChemoTX, Neuroprobe Inc., Cabin John, MD). Twenty-nine µl of chemoattractant or control are added to the lower compartment of each well. The framed filter is aligned with the holes in the corner of the filter frame and placed over the wells. Two and one-half×$10^5$ monocytes in 25 µl of Gey's balanced salt solution+1 mg/ml BSA are added to the upper compartment. The agent is dissolved in Milli Q water and then serially diluted in the Gey's balanced salt solution. In most cases, the serially diluted agent is added to the upper compartment of the chemotaxis chamber. The chamber is incubated at 37° C. in a humidified atmosphere of 5% $CO_2$ for 1.5 hours.

2. Enzme release

The release of N-acetyl-β-D-glucosaminidase from monocytes may be employed to determine whether a therapeutic agent inhibits a cytokine-associated activity. Samples of $1.2 \times 10^6$ monocytes in 0.3 ml of prewarmed medium (136 mM NaCl, 4.8 mM KCl, 1.2 mM $KH_2PO_4$, 1 mM $CaCl_2$, 20 mM Hepes, pH 7.4, 5 mM D-glucose, and 1 mg/ml fatty acid-free BSA) are pretreated for 2 minutes with cytochalasin B (2.7 mg/ml) and then stimulated with a chemokine in the presence or absence of the therapeutic agent. The reaction is stopped after 3 minutes by cooling on ice and centrifugation, and the enzyme activity is determined in the supernatant (Uguccioni et al., *Eur. J. Immunol.*, 25, 64 (1995)).

The release of elastase from neutrophils may also be employed to determine whether a therapeutic agent inhibits a cytokine-associated activity (Pereri et al., *J. Exp. Med.*, 1547 (1988); Clark-Lewis et al., *J. Biol. Chem.*, 269, 16075 (1994)).

3. Cytosolic free $Ca^{2+}$ concentration ($[Ca^{2+}]_i$) changes

Monocytes, eosinophils, neutrophils and lymphocytes loaded with Fura-2 (0.1 nmol/$10^5$ cells) are stimulated with a chemokine in the presence or absence of the therapeutic agent, and $[Ca^{2+}]_i$-related fluorescence changes are recorded (Von Tschanner et al., *Nature*, 324, 369 (1986)). For example, to determine cytosolic $Ca^{2+}$ concentrations in monocytes, monocytes are incubated with 0.5 µM Fura-2/AM for 30 minutes at 37° C. in HEPES-buffered saline (145 mM NaCl, 5 mM KCl, 1 mM $MgCl_2$, 10 mM HEPES, and 10 mM glucose), pH 7.4, at 37° C., supplemented with 1% albumin (w/v) and 1 mM $CaCl_2$. After loading with Fura-2, the cells are centrifuged for 5 minutes at 300×g and then resuspended in buffer containing no added albumin, to a cell density of $1.5 \times 10^6$ cells/ml, and kept at room temperature until use. This protocol results in a cytosolic Fura-2 concentration of about 100 µM. Serial dilutions of chemokines in PBS plus 0.1% albumin (w/v) (sterile filtered) are added to aliquots (0.7 ml) of cell suspension. The Fura-2 fluorescence of the monocyte suspension is measured at 37° C. in a single excitation, single emission (500 nm) wavelength Perkin-Elmer LS5 fluorometer. $[Ca^{2+}]_i$ is calculated from changes in fluorescence measured at a single excitation wavelength of 340 nm.

$[Ca^{2+}]_i$ measurements in cells that are stably transformed with a molecularly cloned chemokine receptor which is not expressed in the corresponding non-transformed cells are performed essentially as described above. After loading with Fura-2/AM, cells ($1 \times 10^6$/ml) are kept in ice-cold medium (118 mM NaCl, 4.6 mM KCl, 25 mM $NaHCO_3$, 1 mM $KH_2PO_4$, 11 mM glucose, 50 mM HEPES, 1 mM $MgCl_2$, 1 mM $CaCl_2$, 0.1% gelatin (pH 7.4). Aliquots (2 ml) of cell suspension are prewarmed at 37° C. for 5 minutes in 3-ml plastic cuvettes, and fluorescence is measured in a fluorometer (Johnson Foundation Biomedical Group) with magnetic stirring and temperature controlled at 37° C. Excitation is set at 340 nm, and emission is set at 510 nm. $[Ca^{2+}]_i$ is calculated as described above.

For studies in monocytes on cross-desensitization of calcium responses, chemokines are added sequentially with a 2-minute interval, and $[Ca^{2+}]_i$ transients are recorded. The concentrations used in these types of studies vary for each chemokine and are set at levels known to induce the maximal response for $[Ca^{2+}]_i$ mobilization (see Forssmann et al., *FEBS Lett.*, 408, 211 (1997); Sozzani et al., *J. Leukoc. Biol.*, 57, 788 (1995); Berkhout et al., *J. Biol. Chem.*, 272, 16404 (1997)).

4. Chemokine binding and binding displacement

In general, specific binding is calculated as the amount of labeled agent bound in the absence of cold competitor minus the amount of labeled agent bound in the presence of cold competitor. The amount of specific binding in the presence of varied amounts of cold competitor can be used to determine the association constant for the agent, as well as the number of binding sites on the cell for the agent, using, for example, Scatchard Analysis. The agent may be labeled by radiolabeling (e.g., iodination) or with a suitable biochemical tag (e.g., biotin) or by addition of a photoactivatable crosslinking group. Agents with an association constant lower than 100 $\mu$M (i.e., which bind more strongly than an agent with an association constant of 100 $\mu$M) and which have at least about 2,500, preferably at least about 10,000, and more preferably greater than 25,000, binding sites per cell for at least one cell type which expresses a chemokine receptor, fall under the scope of this invention. THP-1 cells have at least about 5,000 MCP-1 receptors/cell.

For example, monocytes are suspended in RPMI 1640 medium without bicarbonate containing 0.2% bovine serum albumin and 0.1% azide. Radiolabeled chemokine peptide is incubated with 1–2×10$^6$ cells, e.g., THP-1 cells, in the presence or absence of increasing concentrations of unlabeled chemokine (MCP-1, MCP-3, MCP-4, RANTES or MIP-1$\alpha$) for 15 minutes at 37° C. in a 96-well plate in a final volume of 0.2 ml (e.g., PBS+0.5% FCS). After the incubation, 0.5 ml of ice-cold wash buffer (20 mM Tris, 0.5 M NaCl, pH 7.4) is added, and cells are collected onto a polyethyleneimine-treated Whatman GF/C filter using a Brandall cell harvester. Filters are washed with 4 ml of cold wash buffer, and the radioactivity bound to the filters is counted in a $\gamma$-counter.

For competition studies, the IC$_{50}$ is calculated with a curve fitting program (GraFit, Erithacus Software, London), using a four-parameter logistic, $cpm_{bound} = cpm_{max}/(1+([L]/IC_{50})^s) + cpm_{ns}$, where $cpm_{max}$ represents the binding without competitor, [L] is the competitor concentration, $cpm_{ns}$ is the non-specific binding, and s is the slope factor. The $cmp_{bound}$ is corrected for "no cell" controls. To obtain the $K_d$ and capacity of binding specific binding, data from homologous displacement experiments are fitted into a single-site ligand binding equation using the GraFit best fit program.

Chemokine binding to cells stably transformed with a molecularly cloned chemokine receptor is performed essentially as described above except that radiolabeled agent is diluted with unlabeled chemokine. Cells are incubated with radiolabeled agent plus or minus unlabeled chemokines for 30 minutes at 37° C. (see also, Imai et al., supra; Sozzani et al. (1995), supra; Berkhout et al., supra; WO 97/22698).

5. Binding to the Duffy Antigen Receptor for Chemokines (DARC)

The affinity of the therapeutic agent to DARC may be determined by any method known in the art, e.g., the ability of the agent to inhibit the binding of radio-iodinated MCP-1 to red blood cells (see Example 3). Agents which bind to DARC with a lower association constant (i.e., stronger binding) than they bind to chemokine receptors (i.e., a DARC selectivity ratio of <1), and which bind to DARC with an association constant lower than 100 $\mu$M, preferably lower than 10 $\mu$M and more preferably lower than 1 $\mu$M, are useful in particular embodiments of the methods of the invention. In contrast, agents which do not bind DARC, or do not bind to DARC with an affinity that is greater than their affinity for chemokine receptors (i.e., a selectivity ratio>1), are useful in the practice of other embodiments of the methods of the invention.

6. Inhibition of the co-mitogenic activity of chemokines

Many chemokines are co-mitogenic with low concentrations of FCS, e.g., 50 ng/ml MCP-1+0.5% FCS is a mitogen for smooth muscle cells. Assays well known to the art for determination of DNA synthesis induced by any known chemokine plus a low concentration (<5%) of FCS on suitable cells (e.g., smooth muscle cells) in the presence and absence of the agent may be employed to screen agents for such inhibitory activity. See Porreca et al., *J. Vasc. Res.*, 34, 58 (1997), the disclosure of which is incorporated by reference herein.

7. Anti-lentiviral activity

To prepare cell lines that are susceptible to lentiviral infection as a result of the expression of a particular chemokine receptor, a molecularly cloned chemokine receptor is introduced into a cell line that does not otherwise express the chemokine receptor, e.g., HeLa-MAGI (Kimpton and Emerman, *J. Virol.*, 66(5), 3026 (1992)) or U373-MAGI (Harrington and Geballe, *J. Virol.*, 67, 5939 (1993)) cells, by infection with a retroviral vector. Expression of the chemokine receptor on the cell surface is demonstrated by immunostaining live cells using antibody. Expression of the RNA encoding the receptor is demonstrated by RT-PCR analysis. HeLa-MAGI and U373-MAGI express $\beta$-galactosidase after lentiviral infection. Incubation of infected cells with X-gal results in the deposit of a blue stain in these cells.

Infection of the chemokine receptor-stably transformed cell lines with HIV in the presence or absence of agent is performed in 12-well plates with 10-fold serial dilutions of 300 $\mu$l of virus in the presence of 30 $\mu$g/ml DEAE-Dextran as described (Kimpton and Emerman, supra). Viral stocks are normalized by ELISA or p24$^{gag}$ (Coulter Immunology) or p27$^{gag}$ (Coulter Immunology) for HIV-1 and HIV-2/SIV, respectively, using standards provided by the manufacturer.

Two days after infection, cells are fixed and stained for $\beta$-galactosidase activity with X-gal. The cells are stained for 50–120 minutes at 37° C. The infectious titer is the number of blue cells per well multiplied by the dilution of virus and normalized to 1 ml.

For other methods useful to determine whether an agent inhibits lentiviral infection and/or replication, see also Cocchi et al., *Science*, 270, 1811 (1995), and WO97/22698.

8. Agonists

To determine whether an agent of the invention is a chemokine receptor agonist, varying amounts of a labeled form of the agent, e.g., biotinylated, are mixed with cells that express the receptor, e.g., THP-1 cells express receptors for MCP-1, MIP1$\alpha$, SDF-1$\alpha$ and IL-8, while Jurkat cells express functional receptors for SDF-1. The affinity of the labeled agent for the cells is then determined. Agents that bind to receptors with a reasonable affinity and interact with the receptor by inducing signaling, are within the scope of the invention. While not encompassed by the term "agonist" or "antagonist", agents that bind to or near the receptor but elicit no response are also within the scope of the invention, and are termed "neutral" agents.

Agents with agonist activity may also be identified using the transwell migration assay, where the cells are placed in the upper compartment (see FIG. 1) in the absence of agent, and the agent, e.g. peptide 2[MCP-1], is placed at varying concentrations in the lower compartment in place of the chemokine. If the agent(s) have agonist activity, more cells are found in the lower compartment at the end of the assay in wells containing the agent(s) than in wells containing inactive control, i.e., agent or medium alone. Preferably, agents having agonist activity also stimulate migration of primary human cells, e.g., monocytes, in a transwell migration assay.

Moreover, weak agonists or neutral agonists (agents which bind to the receptor but do not inhibit binding of native chemokine and its subsequent signaling, nor do they induce signaling themselves) can be identified by screening the agents for ability to displace the binding of HIV gp120, specifically the V3 loop of gp120, to the surface of THP-1 cells or Jurkat cells. Cells are incubated with labeled (for example, radioiodinated) recombinant gp120 protein in an amount effective to bind to the virus receptor, in the presence and absence of various concentrations of the agent(s). Agents which reduce or abolish gp120 binding are agonists or neutral agonists within the scope of the invention.

B. Nucleic Acid Molecules of the Invention

1. Sources of the Nucleic Acid Molecules of the Invention

Sources of nucleotide sequences from which the present nucleic acid molecules encoding a chemokine peptide, a variant thereof or the nucleic acid complement thereof, include total or polyA$^+$RNA from any eukaryotic, preferably mammalian, cellular source from which cDNAs can be derived by methods known in the art. Other sources of the DNA molecules of the invention include genomic libraries derived from any eukaryotic cellular source. Moreover, the present DNA molecules may be prepared in vitro, e.g., by synthesizing an oligonucleotide of about 100, preferably about 75, more preferably about 50, and even more preferably about 40, nucleotides in length, or by subcloning a portion of a DNA segment that encodes a particular chemokine.

2. Isolation of a Gene Encoding a Chemokine

A nucleic acid molecule encoding a chemokine can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone chemokine cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, N.Y., 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other eukaryotic chemokines. One primer is prepared which is predicted to anneal to the antisense strand, and another primer prepared which is predicted to anneal to the sense strand, of a DNA molecule which encodes a chemokine.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode a chemokine is to screen a cDNA library. Screening for DNA fragments that encode all or a portion of a cDNA encoding a chemokine can be accomplished by probing the library with a probe which has sequences that are highly conserved between genes believed to be related to the chemokine, e.g., the homolog of a particular chemokine from a different species, or by screening of plaques for binding to antibodies that specifically recognize the chemokine. DNA fragments that bind to a probe having sequences which are related to the chemokine, or which are immunoreactive with antibodies to the chemokine, can be subcloned into a suitable vector and sequenced and/or used as probes to identify other cDNAs encoding all or a portion of the chemokine.

As used herein, the terms "isolated and/or purified" refer to in vitro isolation of a DNA or polypeptide molecule from its natural cellular environment, and from association with other components of the cell, such as nucleic acid or polypeptide, so that it can be sequenced, replicated, and/or expressed. For example, "isolated chemokine nucleic acid" is RNA or DNA containing greater than 9, preferably 36, and more preferably 45 or more, sequential nucleotide bases that encode at least a portion of a chemokine, or a variant thereof, or a RNA or DNA complementary thereto, that is complementary or hybridizes, respectively, to RNA or DNA encoding the chemokine and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated chemokine nucleic acid is RNA or DNA that encodes human MCP-1 and shares at least about 80%, preferably at least about 90%, and more preferably at least about 95%, sequence identity with the MCP-1 polypeptide having SEQ ID NO:16.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.,* 9, 6103 (1981), and Goeddel et al., *Nucleic Acids Res.,* 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3. Variants of the Nucleic Acid Molecules of the Invention

Nucleic acid molecules encoding amino acid sequence variants of a chemokine peptide are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the chemokine peptide.

Oligonucleotide-mediated mutagenesis is a preferred method for preparing amino acid substitution variants of a chemokine peptide. This technique is well known in the art as described by Adehnan et al., *DNA,* 2, 183 (1983). Briefly, chemokine DNA is altered by hybridizing an oligonucleotide encoding the desired mutation to a DNA template, where the template is the single-stranded form of a plasmid or bacteriophage containing the unaltered or native DNA sequence of the chemokine. After hybridization, a DNA polymerase is used to synthesize an entire second complementary strand of the template that will thus incorporate the oligonucleotide primer, and will code for the selected alteration in the chemokine DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.* 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.,* 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the chemokine, and the other strand (the original template) encodes the native, unaltered sequence of the chemokine. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a preselected DNA segment encoding peptide 3 (1–12)[MCP-1] having SEQ ID NO:1, wherein the DNA segment comprises SEQ ID NO:76, or variants of SEQ ID NO:76, having nucleotide substitutions which are "silent" (see Table 1). That is, when silent nucleotide substitutions are present in a codon, the same amino acid is encoded by the codon with the nucleotide substitution as is encoded by the codon without the substitution. For example, valine is encoded by the codon GTT, GTC, GTA and GTG. A variant of SEQ ID NO:76 at the tenth codon in the mature polypeptide (GTC in SEQ ID NO:79) includes the substitution of GTT, GTA or GTG for GTC. Other "silent" nucleotide substitutions in SEQ ID NO:76 which can encode peptide 3 (1–12)[MCP-1] having SEQ ID NO:1 can be ascertained by reference to Table 1 and page D1 in Appendix D in Sambrook et al., *Molecular Cloning: A Laboratory Manual* (1989). Nucleotide substitutions can be introduced into DNA segments by methods well known to the art. See, for example, Sambrook et al., supra. Likewise, nucleic acid molecules encoding other mammalian, preferably human, chemokines may be modified in a similar manner. Thus, nucleic acid molecules encoding at least a portion of MCP-2 (SEQ ID NO:80), MCP-3 (SEQ ID NO:81), MCP-4 (SEQ ID NO:28), MIP1α (SEQ ID NO:82), MIP1β (SEQ ID NO:79), RANTES (SEQ ID NO:78), SDF1α (SEQ ID NO:77), IL8 (SEQ ID NO:58), GROα (SEQ ID NO:55), eotaxin (SEQ ID NO:51), MIG (SEQ ID NO:39), PF-4 (SEQ ID NO:37), 1309 (SEQ ID NO:36), HCC-1 (SEQ ID NO:35), C10 (SEQ ID NO:34), CCR-2 (SEQ ID NO:33), ENA-78 (SEQ ID NO:32), GROβ (SEQ ID NO:31), IP10 (SEQ ID NO:30), SDF1β (SEQ ID NO:29) or GROα (SEQ ID NO:55), or the complement thereto, may be modified so as to yield nucleic acid molecules of the invention having silent nucleotide substitutions, or to yield nucleic acid molecules having nucleotide substitutions that result in amino acid substitutions (see peptide variants hereinbelow).

TABLE 1

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

C. In Vivo Studies

To further determine whether a particular agent is useful in the practice of the methods of the invention, an animal model is identified for a human disease. Transgenic animal models for human disease may also be employed to identify agents useful in the methods of the invention. For example, models of chemokine-induced macrophage recruitment associated with human atherosclerosis include, but are not limited to, mice with a homozygous deletion of the apolipoprotein E (apoE) gene, mice overexpressing human apoB and Watanabe heritable hyperlipidemic rabbits. Models for autoimmune disease include the collagen-induced arthritis in DBA/1 mice and myelin basic protein-induced experimental autoimmune encephalomyelitis. Models for osteoporosis include ovariectomized female rats, mice, monkeys, rats treated with heparin or with glucocorticoids as well as suspension-induced osteoporosis in rats. Models for HIV infection include infection of monkeys with SIV, SIV isolates, HIV or HIV isolates or rabbits with HIV or HIV isolates. Other animal models for lentiviral infection include cats infected with FIV, horses with EIAV, and goats infected with CAEV (which is also an animal model for arthritis).

The efficacy of an agent of the invention may be assessed by measuring the extent of inflammation, or the extent of macrophage infiltration of affected tissues. Macrophage infiltration can be detected by staining tissue sections with antibodies which specifically detect macrophages (e.g., mac-i antiserum). Inflammation or other symptoms of disease may be detected by measuring appropriate clinical parameters, using techniques which are well known to those skilled in the art. For example, apoE knockout mice are treated with an agent, such as CRD-leu$_4$ile$_{11}$peptide 3, e.g., by intraperitoneal injection, for a period of twelve weeks, while control litter mates receive a suitable control peptide with no known biological activity. At the end of twelve weeks, the animals are sacrificed and the effect of the agent is assessed by measuring the reduction in macrophage recruitment into the vessel wall by quantitative immunohistochemistry using mac-1 antiserum, and by measuring the reduction in the extent of vascular lipid lesion formation by histochemistry using oil red O staining in accordance with Paigen, *Arteriosclerosis*, 10, 316 (1990).

Apo(a) transgenic mice develop lesions when fed a lipid-rich diet. These lesions do not contain any macrophages. In contrast, C57B16 inbred mice develop lipid lesions of similar size and severity to those in apo(a) transgenic mice, but these lesions are rich in infiltrating macrophage. Lesions of apo(a) mice, C57B16 mice, and 6 other strains of mice which develop lipid lesions rich with macrophage, were screened by quantitative immunofluorescence for levels of pro-inflammatory mediators, e.g., TNF-α, MCP-1, MIP-1α, IL1β, ICAM-1, VCAM-1, and P-selectin. TNF-α, MIP-1α, IL1β, ICAM-1, VCAM-1 and P-selectin were all expressed at identical levels in the apo(a) mouse lesions and the C57B16 lesions. Thus, while these pro-inflammatory mediators may be necessary to infiltration, they are not sufficient alone. In marked contrast, MCP-1 was completely absent from the lesions of apo(a) mice, but expressed at high levels in lesions from all other mouse lines which had macrophage-rich lesions.

Confocal microscopic analysis of sections of blood vessel wall with lesions triple stained with antibodies specific for SM-α-actin (smooth muscle cells; LA4 antibody), macrophages (Mac-1 antibodies) and MCP-1, showed that MCP-1 is not exclusively expressed by macrophage. That is, both smooth muscle cells and macrophages expressed MCP-1. Thus, MCP-1 may be the missing "inflammatory mediator" in the apo(a) mouse model of atherosclerosis. These results suggest that the lack of MCP-1 in apo(a) mice lesions may not be a consequence of the absence of macrophages, but instead contribute to the cause of lack of monocyte infiltration. Moreover, these results provide evidence that the chemokine MCP-1 plays a role in atherosclerotic vascular inflammation. Thus, MCP-1 can provide the basis for analogs which block the recruitment activity of this chemokine.

Chemokines other than MCP-1 may also be involved in macrophage recruitment, inflammation and pathogenesis of atherosclerosis, and in other diseases associated with inappropriate proliferation. For example, MIP1α has been implicated in the inappropriate inflammation in multiple sclerosis. Thus, sequences analogous to peptide 2 and 3 from MIP1α may be particularly useful to treat or prevent multiple sclerosis. Therefore, when a particular chemokine is implicated in a particular disease, sequences from that particular chemokine may be especially useful to treat or prevent that disease. Preferred agents falling within the scope of the invention are inhibitors of signaling of more than one chemokine, and preferably of all chemokines. Thus, it may be preferable to prepare chemokine peptide analogs having sequences from a chemokine other than the one(s) associated with a particular disease process. Selection of a particular agent to treat a particular disease may be based on bioavailability, toxicity, DARC binding or other similar criteria.

II. Preparation of Agents Falling Within the Scope of the Invention

A. Nucleic acid molecules

1. Chimeric Expression Cassettes

To prepare expression cassettes for transformation herein, the recombinant or preselected DNA sequence or segment may be circular or linear, double-stranded or single-stranded. A preselected DNA sequence which encodes an RNA sequence that is substantially complementary to a mRNA sequence encoding a chemokine is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for a chemokine, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual,* Cold Spring Harbor Laboratory Press (2d ed., 1989), provides suitable methods of construction.

2. Transformation into Host Cells

The recombinant DNA can be readily introduced into the host cells, e.g., mammalian, bacterial, yeast or insect cells by transfection with an expression vector comprising DNA encoding a chemokine or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding the chemokine or its complement, which host cell may or may not express significant levels of autologous or "native" chemokine.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular chemokine, e.g., by immunological means (ELISAs and Western blots) or by assays described hereinabove to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host cell.

B. Peptides, Peptide Variants, and Derivatives Thereof

The present isolated, purified chemokine peptides, peptide variants or derivatives thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis,* W. H. Freeman Co., San Francisco (1969); Merrifield, *J. Am. Chem. Soc.,* 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given chemokine peptide can be readily prepared. For example, amides of the chemokine peptide or chemokine peptide variants of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the chemokine peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al., *Science,* 276, 276 (1997)).

In addition, the amino acid sequence of a chemokine peptide can be modified so as to result in a chemokine peptide variant. The modification includes the substitution of at least one amino acid residue in the peptide for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, omithine, citruline, α-methyl-alanine, para-benzoyl-phenylalanine, phenylglycine, propargylglycine, sarcosine, and tert-butylglycine.

One or more of the residues of the peptide can be altered, so long as the peptide variant is biologically active. For example, for peptide 3 [MCP-1] variants, e.g., $Ser_7$peptide 3(1–12)[MCP-1](SEQ ID NO:11), it is preferred that the variant has at least about 10% of the biological activity of the corresponding non-variant peptide, e.g., a peptide having SEQ ID NO: 1. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions are shown in Table 2 under the heading of exemplary substitutions. More preferred substitutions are under the heading of preferred substitutions. After the substitutions are introduced, the variants are screened for biological activity.

TABLE 2

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic; trp, tyr, phe.

The invention also envisions peptide variants with non-conservative substitutions. Non-conservative substitutions entail exchanging a member of one of the classes described above for another.

Acid addition salts of the peptide or variant peptide or of amino residues of the peptide or variant peptide may be prepared by contacting the peptide or amine with one or more equivalents of the desired inorganic or organic acid, such as, for example, hydrochloric acid. Esters of carboxyl groups of the peptides may also be prepared by any of the usual methods known in the art.

Moreover, it is also envisioned that the agents of the invention, e.g., chemokine peptides, are modified in a manner that increases their stability in vivo, i.e., their bioavailability. These modified agents are termed "derivatives."

Methods to prepare such derivatives are well known to the art. One method to stabilize peptides is to prepare derivatives which are cyclized peptides (see EPA 471,453 (amide bonds); EPA 467,701 (disulfide bonds); EPA 467,699 (thioether bonds). Other modifications which may increase in vivo stability are disclosed in Jameson et al. (Nature, 368, 744 (1994)); U.S. Pat. No. 4,992,463; and U.S. Pat. No. 5,091,396. A preferred embodiment of the invention is a chemokine peptide or variant that has been cyclized by addition of one or more cysteine residues to the N and/or C terminus of the peptide, as well as peptides which are constructed of the reverse sequence (i.e., reading C-terminal to N-terminal) of D-form amino acids. A more preferred embodiment of this invention is a peptide which is both cyclized and constructed with the reverse sequence of D-form amino acids, i.e., a CRD derivative.

C. Chemokine Analogs

1. Isosteres of chemokine tripeptides (a compound of formula (IV))

A compound of formula (IV), wherein $Z=CH_3$; R=indolyl; Y=O; and $X=CH_3$, can be prepared from N-tBOC-NinBOC-L-tryptophan-OH and cyclohexenone. For example, 2-cyclohexen-1-one (Aldrich C1O,281–4) can be reacted with lithium dimethylcuprate in the presence of trimethylsilyl chloride (Aldrich 38,652–9) (Reaction 1) to trap the enolate intermediate. Lithium dimethylcuprate is prepared from methyllithium and a copper (I) salt in a 2:1 stoichiometry, prior to use in the reaction, by methods well known to those skilled in the art (e.g., House et al., J. Org. Chem., 40, 1460 (1975)). The addition of α-β unsaturated ketones by organocuprates is described, for example, in House et al., J. Org. Chem., 31, 3128 (1966). Similarly, capture of the enolate by trimethyl silyl chloride is described in House et al., J. Org. Chem., 36, 2361 (1971). The trapped enolate is then resolved to the α-iododerivative, for example, by addition of molecular iodine in the presence of acetoxy-silver and tetrabutylammonium fluoride, according to the method of Rubottom (J. Org. Chem., 44, 1731 (1979)) to give the trans-disubstituted cyclohexanone of formula (VI).

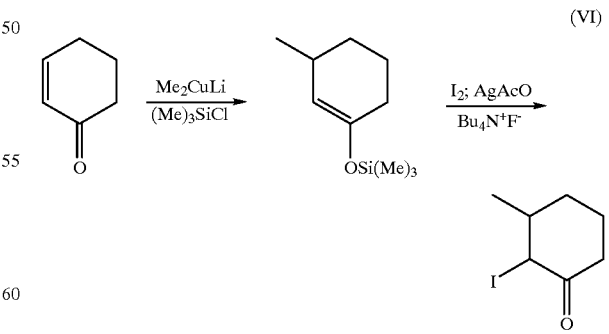

Conversion of the iodide of formula (VI) to a secondary alcohol, and formation of an ester, for example, with acetic anhydride yields a compound of formula (VIIb).

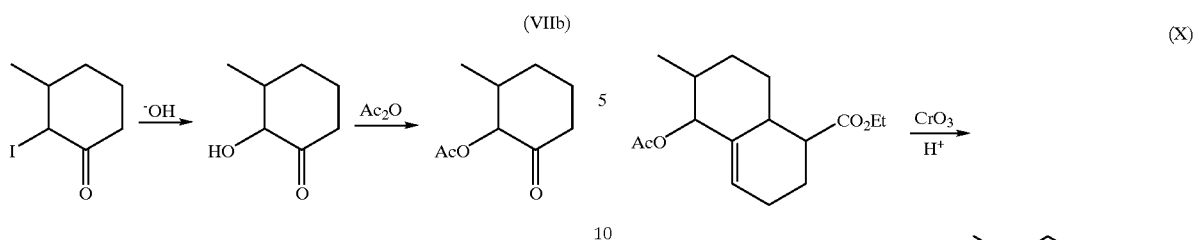

A compound of formula (VIIb) can alternatively be prepared by conversion of the above trimethylsilyl ether enolate to the α-hydroxy ketone followed by formation of the ester, using procedures which are well known in the art.

A compound of formula (VIIb) can be alkylated, for example, with vinyl magnesium bromide under standard conditions, and dehydrated (for example, in the presence of molecular iodine and heat) to yield a diene of formula (VIII):

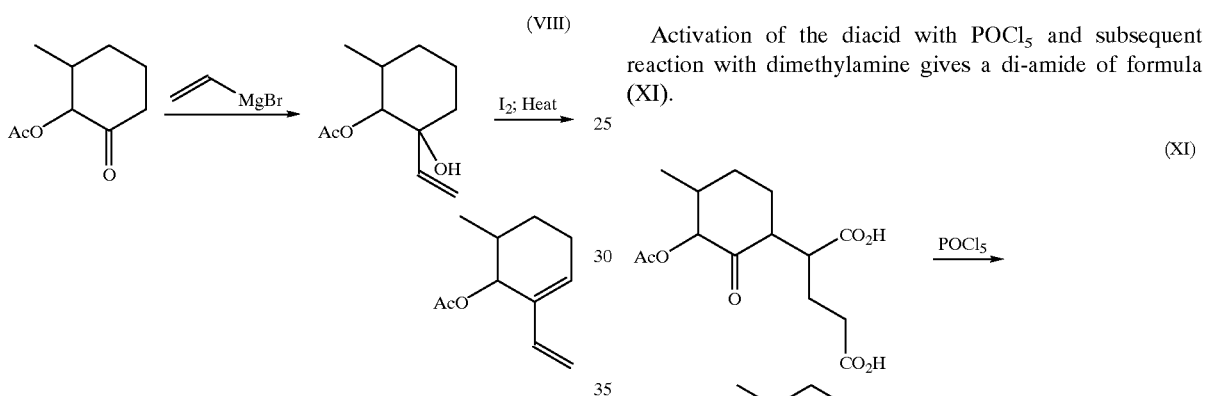

Diels-Alder reaction between the diene of formula (VIII) and ethyl acrylate (Aldrich E970–6) gives a stereospecific and regio specific product of formula IX. For example, the cyclization reaction can be performed by mixing the compound of formula (VIII) and ethyl acrylate in a sealed tube and heating, essentially as described by Green et al. (*Adv. Pest Control Res.*, 3 129 (1960)).

Oxidative cleavage of the double bond in a compound of formula (IX) gives a diacid of formula (X). Such an oxidative cleavage may conveniently be carried out by ozonolysis or by oxidation with an acid chromate. For example, using CrO₃ in acid, the compound of formula (X) may be prepared, essentially as described by Eschenmoser & Winter, *Science*, 196, 1410 (1977).

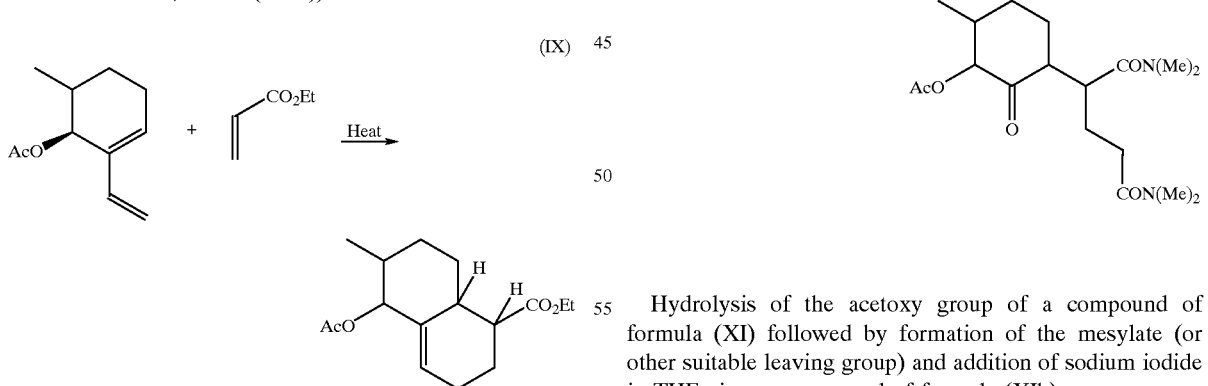

Activation of the diacid with POCl₅ and subsequent reaction with dimethylamine gives a di-amide of formula (XI).

Hydrolysis of the acetoxy group of a compound of formula (XI) followed by formation of the mesylate (or other suitable leaving group) and addition of sodium iodide in THF gives a compound of formula (XIb).

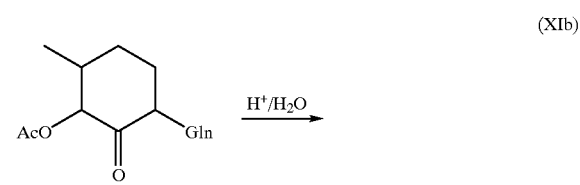

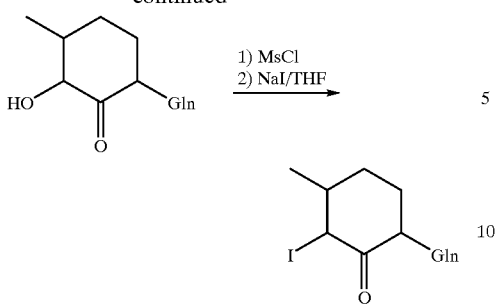

Reaction of a compound of formula (XI) and a compound of formula (XII) in the presence of anhydrous potassium carbonate in dry DMF, essentially as described by Lygo and Rudd (*Tetrahedron Lett.*, 36, 3577 (1995)) followed by removal of the sulfone, for example, using $SmI_2$, gives a compound of formula (XII) which can be deprotected and acylated to give a compound of formula (IV) wherein $R^2$ and $R^3$ are $NMe_2$.

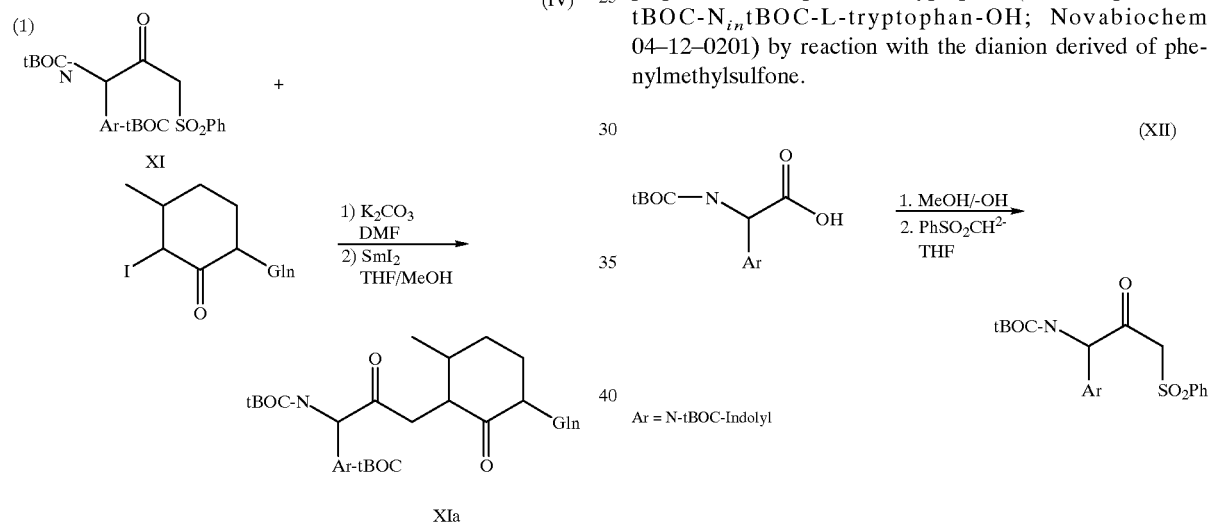

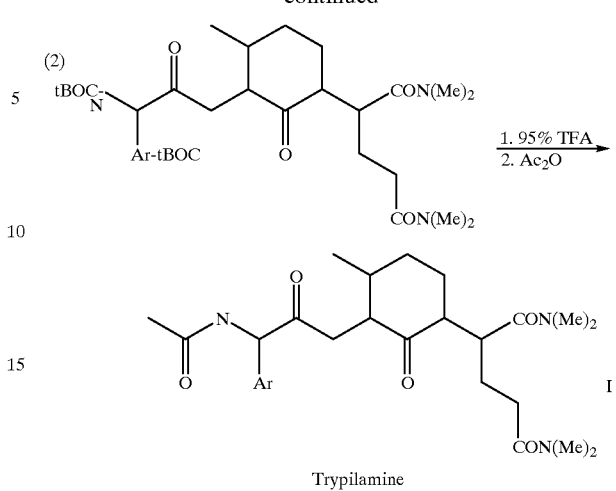

An intermediate of formula (XII) may conveniently be prepared from a protected tryptophan (for example, N-α-tBOC-N$_{in}$tBOC-L-tryptophan-OH; Novabiochem 04–12–0201) by reaction with the dianion derived of phenylmethylsulfone.

A preferred synthesis for a compound of formula (IV) is:

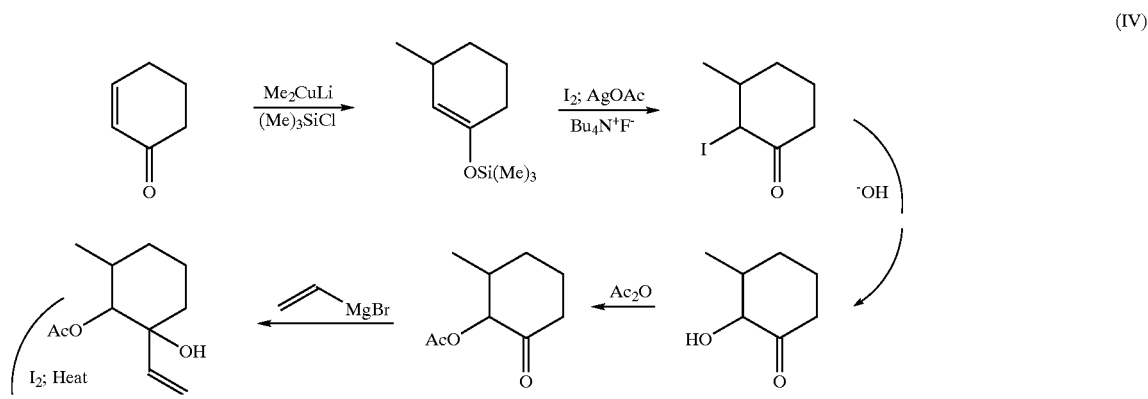

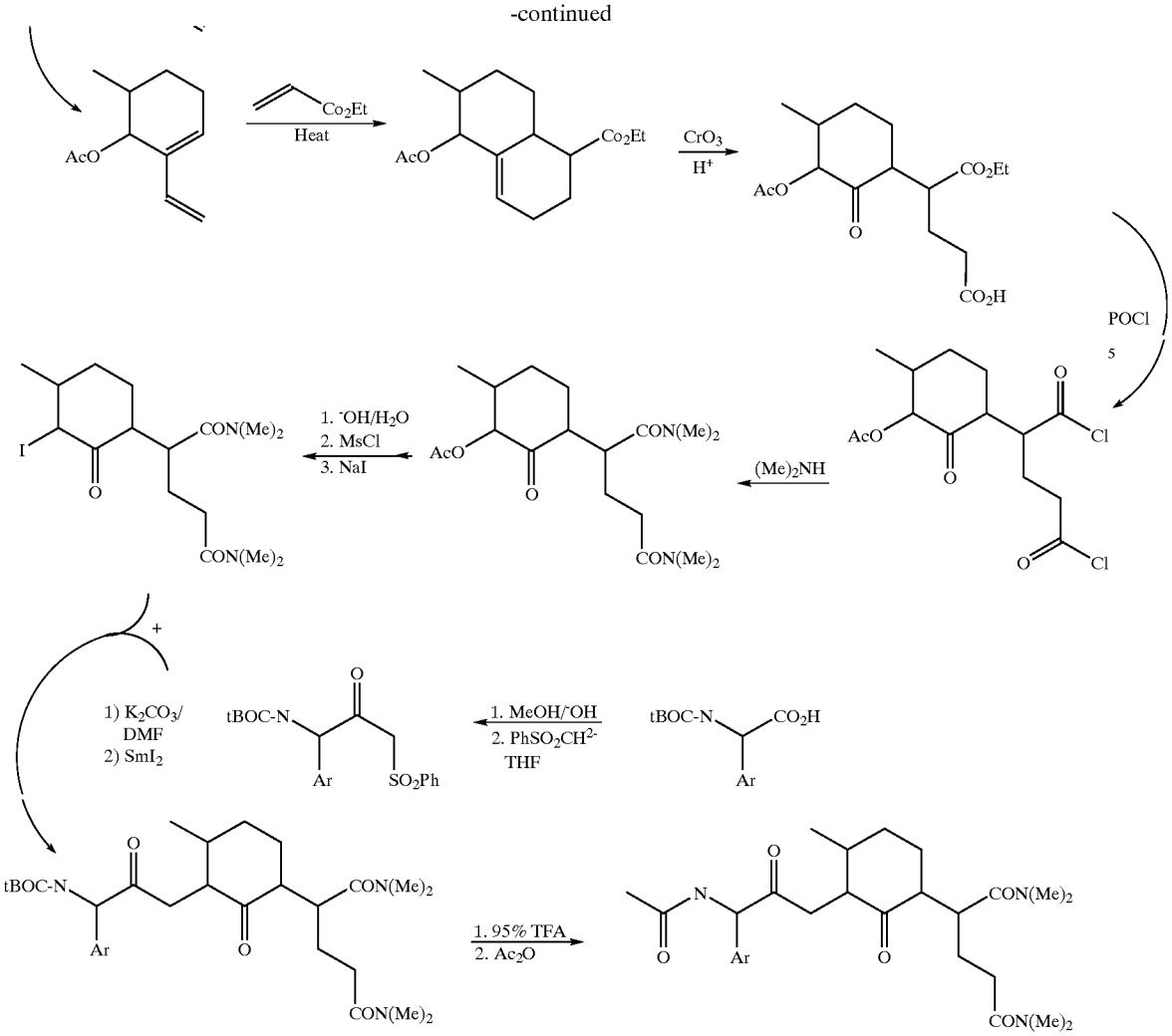

Thioketone derivatives (Y=S) may be synthesized by insertion of an additional reaction, in which the β-ketosulfone derivative of protected tryptophan is converted to the thioketone derivative. For example, reaction with a dithiol, such as 1,2-ethanedithiol, forms a thioacetal which can be hydrolyzed in the presence of $H_2S$ under anhydrous conditions, to yield the thioketone. The conversion may also be carried out using [2,4-bis(4-methoxyphenyl)-1,3-dithia-2,4-diphos-phetane-2,4 disulfide] (Lawesson's Reagent). Reaction of the thioketone derivative with the compound of formula (XI) gives a compound of formula (I) wherein Y=S.

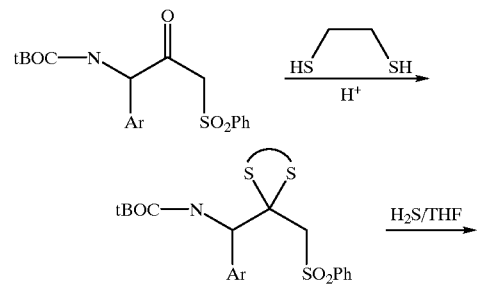

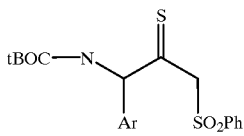

Aryl substituents other than indolyl require preparation of suitably protected β-ketosulfone derivatives of the appropriate amino acid. Where the amino acid is readily available, the reaction can be performed using the appropriate tBOC or Fmoc protected amino acid (phenylalanine and tyrosine, respectively), for example, from Novabiochem. When the amino acid is not readily available (e.g., R=coumaryl), the suitably protected amino acid must first be prepared by methods well established in the art for synthesis of non-standard amino acids (for example, see Yuan and Hruby, *Tetrahedron Lett.*, 38, 3853 (1997)).

As illustrated below, a compound of formula (V) may conveniently be prepared from a protected diol of formula 18 using procedures which are well known in the art, by removal of the protecting group $Pg_1$ and elaboration of the resulting alcohol to introduce the $R_7$ containing amide, and by removal of the protecting group $Pg_2$ and elaboration of the resulting alcohol to introduce $R_8$ and the oxo functionality α to $R_8$.

An intermediate of formula 18 can be prepared as illustrated below. An intermediate aldehyde of formula 15 can conveniently be prepared by reduction of an ester of formula 13, or by oxidation of an alcohol of formula 14. An aldehyde of formula 15 can be converted to a difluoride of formula 16 using procedures which are well known in the art, for example by treatment with $SF_4$. Treatment of the difluoride of formula 16 with triphenyl phosphine, under standard conditions, gives a phosphonium salt 17. Deprotonation of of the phosphonium salt with a suitable base, and treated with a ketone of formula 19, gives a diene of formula 18.

An intermediate of formula 19 can be prepared as illustrated below. An aldehyde of formula 20 can be converted to a difluoride of formula 21 using procedures which are well known in the art, for example by treatment with $SF_4$.

Treatment of the difluoride with triphenyl phosphine, under standard conditions, gives a phosphonium salt 22. Deprotonation of of the phosphonium salt with a suitable base, and treated with an aldehyde of formula 26, gives an olefin of formula 23. Removal of the protecting group $Pg_3$ from a compound of formula 23, followed by oxidation of the resulting alcohol gives a ketone of formula 19.

An intermediate aldehyde of formula 26, can be prepared by reduction of a corresponding ester of formula 25. An ester of formula 25, can conveniently be prepared from an ester of formula 24 using techniques which are well known in the art.

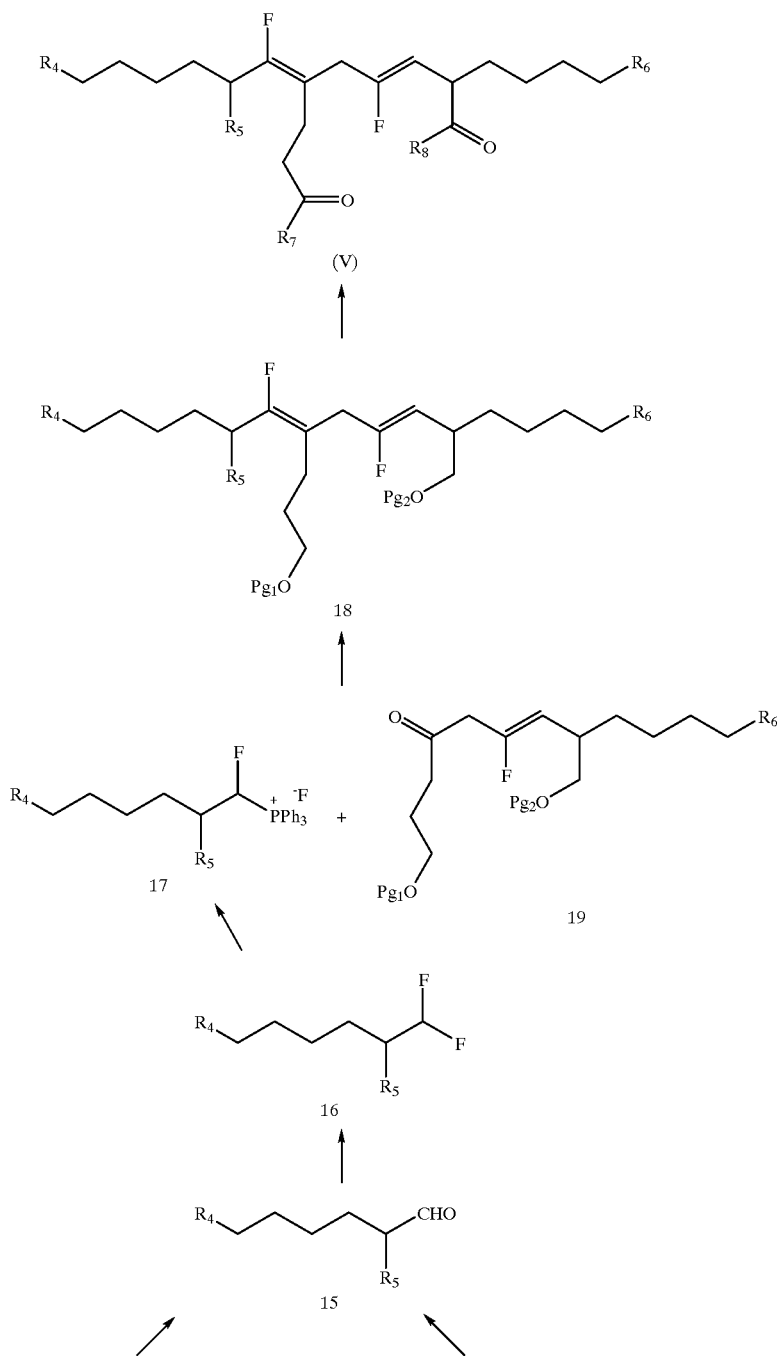

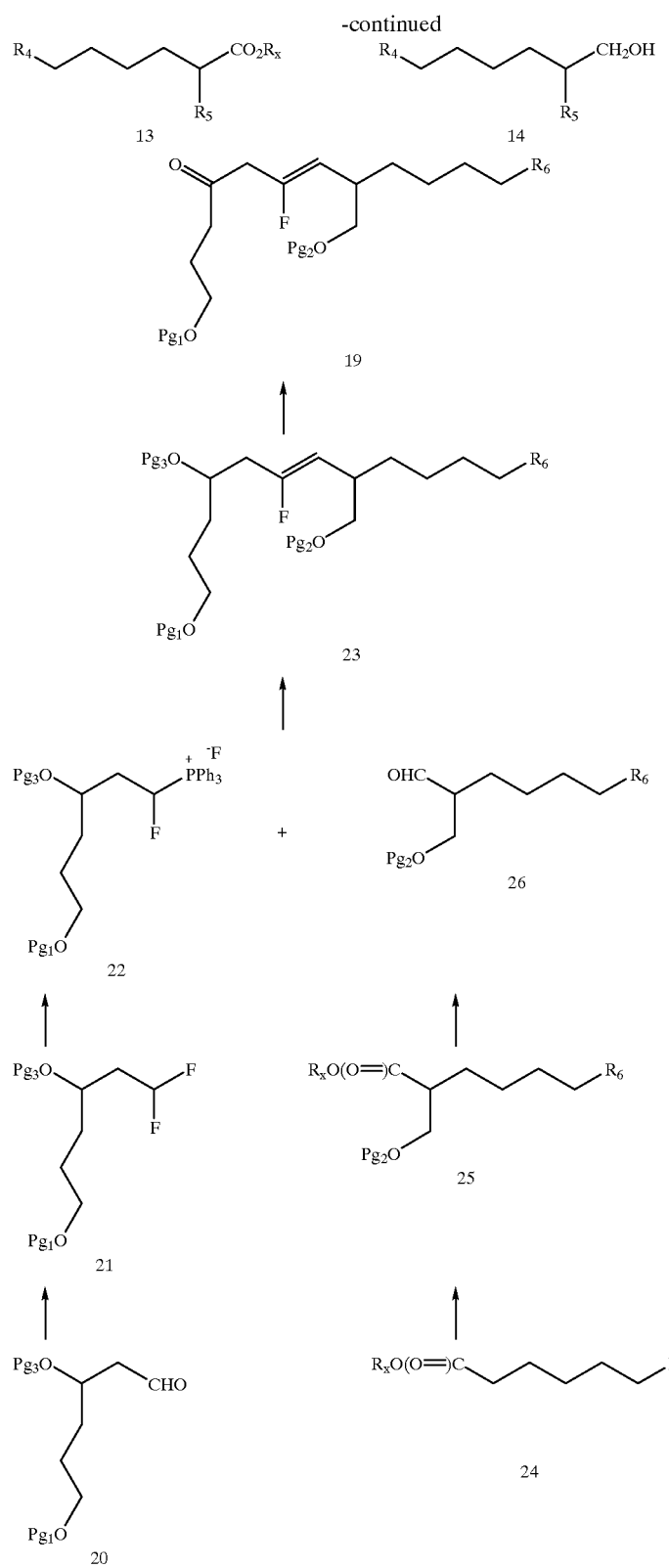

Other useful chemokine analogs may be identified by the methods described hereinabove. In particular, chemokine analogs that are orally bioavailable, and stable and potent inhibitors of chemokine activity are preferred.

D. Targeting of the Therapeutic Agent

Chemokine peptides, variants, analogs or derivatives thereof may be targeted to a specific therapeutic site by linking the therapeutic agent to a moiety that specifically binds to a cellular component, e.g., antibodies or fragments thereof, lectins, transferrin (for liver targeting) and small molecule drugs, so as to form a therapeutic conjugate. Targeting of the therapeutic agents of the invention can result in increased concentration of the therapeutic agent at a specific anatomic location. Moreover, the linking of a therapeutic agent of the invention to a binding moiety may increase the stability of the therapeutic agent in vivo. For example, an anti-CD4 mimetic that binds to the CD4 receptor may be linked to a therapeutic agent of the invention so as to result in a therapeutic conjugate, a portion of which binds to the HIV co-receptor. This may enhance the ability to target the therapeutic agent to a particular cell type and thus block HIV infection of that cell type.

For neoplasia, anti-tumor antibodies such as NR-LU-10 (anti-carcinoma), NR-ML-5 (anti-melanoma), or anti-CD45 (anti-lymphoma), may be useful to localize the therapeutic agent to a particular type of tumor. For infectious disease, antibodies which recognize a pathogen-specific epitope, such as mAb 17.41 (*Cryptosporidium parvum*), may be employed. To target to joints for treating rheumatoid arthritis, anti-synovium or chondroitin sulfate (e.g., Catalog No. C8035, Sigma Chemical Co., St. Louis, Mo.) antibodies can be linked to a therapeutic agent of the invention). To treat or prevent asthma or pneumonia, antibodies to the bronchial epithelial may be useful to prepare immunoconjugates for use in the methods of the invention.

Other antibodies useful in targeting a therapeutic agent of the invention to a specific site or cell type include antibodies specific for blood vessels or lymphatics (e.g., Ulex europaeus-I lectin, Catalog No. U4754, Sigma Chemical Co., St. Louis, Mo.), blood clots or platelets (e.g., Catalog Nos. F9902, F4639, F2506, F8512, Sigma Chemical Co., St. Louis, Mo.), T cells (e.g., Catalog Nos. C7048 (CD3); C1805 (CD4); C7173 (CD5); and C7298 (CD7), Sigma Chemical Co., St. Louis, Mo.), brain (e.g., Catalog Nos. S2644 and S2407, Sigma Chemical Co., St. Louis, Mo.), tumors (e.g., Catalog No. C2331, Sigma Chemical Co., St. Louis, Mo.), epithelial cells (e.g., Catalog Nos. E6011 and C 1041, Sigma Chemical Co., St. Louis, Mo.), fibroblasts (e.g., Catalog Nos. F4771 and V4630, Sigma Chemical Co., St. Louis, Mo.), macrophage (e.g., Catalog No. M1919, Sigma Chemical Co., St. Louis, Mo.), stomach lumen (e.g., Catalog No. M5293, Sigma Chemical Co., St. Louis, Mo.), neutrophils (e.g., Catalog Nos. N1890 and N1765, Sigma Chemical Co., St. Louis, Mo.), tendons (e.g., Catalog No. E4013, Sigma Chemical Co., St. Louis, Mo.), skin (e.g., Catalog No. K4252, Sigma Chemical Co., St. Louis, Mo.) mammary tissue or epithelium (e.g., Catalog No. C6930, Sigma Chemical Co., St. Louis, Mo.) and skeletal muscle (e.g., Catalog Nos. D8281 and D1033, Sigma Chemical Co., St. Louis, Mo.).

To prepare immunoconjugates useful for targeting a malignant or virus-infected cell, an antibody or fragment thereof having a specificity for a surface antigen on a malignant cell or virus-infected is attached to a therapeutic agent of the invention. Preferably, a chemokine peptide or variant thereof is attached via peptide bonds to the carboxy termini regions, e.g., CH3, of antibody heavy chains. The immunoconjugates can be prepared by genetic engineering techniques, i.e, by forming a nucleic acid construct encoding the chimeric immunoconjugate. Preferably, the gene construct encoding the immunoconjugate includes, in 5' to 3' orientation, a DNA segment which encodes a heavy chain variable region, a DNA segment encoding the heavy chain constant region, and a DNA segment coding for the chemokine peptide, peptide variant, or repeats thereof. The fused gene is inserted into an expression vector for transfection of the appropriate recipient cells where it is expressed. The hybrid chain can be combined with a light (or heavy) chain counterpart to form monovalent and divalent immunoconjugates.

The heavy chain constant region for the conjugates can be selected from any of the five isotypes: alpha, delta, epsilon, gamma or mu. Heavy chains or various subclasses (such as the IgG subclasses 1–4) can be used. The light chains can have either a kappa or lambda constant chain. DNA sequences for these immunoglobulin regions are well known in the art (see, e.g., Gillies et al., *J. Immunol. Meth.,* 125 191 (1989)).

In preferred embodiments, the variable region is derived from an antibody specific for the target antigen (an antigen associated with a diseased cell such as a cancer cell or virus-infected cell), and the constant region includes the CH1, CH2 and CH3 domains. The gene encoding the chemokine peptide or variant is joined, e.g., by appropriate linkers, e.g., by DNA encoding $(Gly_4\text{-}Ser)_3$ in frame to the 3' end of the gene encoding the constant region (e.g., CH3 exon), either directly or through an intergenic region. In certain embodiments, the intergenic region can comprise a nucleotide sequence coding for a proteolytic cleavage site. This site, interposed between the immunoglobulin and the chemokine peptide or variant, can be designed to provide for proteolytic release of the chemokine peptide or variant at the target site. For example, it is well known that plasmin and trypsin cleave after lysine and arginine residues at sites that are accessible to the proteases. Many other site-specific endoproteases and the amino acid sequences they attack are well known.

The nucleic acid construct can include the endogenous promoter and enhancer for the variable region-encoding gene to regulate expression of the chimeric immunoglobulin chain. For example, the variable region encoding genes can be obtained as DNA fragments comprising the leader peptide, the VJ gene (functionally rearranged variable (V) regions with joining (J) segment) for the light chain or VDJ gene for heavy chain, and the endogenous promoter and enhancer for these genes. Alternatively, the gene coding for the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones are then achieved by DNA sequencing of the cloned genes and comparison of the sequence to the corresponding sequence of the full length, properly spliced mRNA.

Genes encoding appropriate variable regions can be obtained generally from Ig-producing lymphoid cells. For example, hybridoma cell lines producing Ig specific for tumor associated antigens or viral antigens can be produced by standard somatic cell hybridization techniques. These Ig-producing cell lines provide the source of variable region genes in functionally rearranged form. The variable region genes are typically of murine origin because the murine system lends itself to the production of a wide variety of Igs of desired specificity.

The DNA fragment containing the functionally rearranged variable region gene is linked to a DNA fragment containing the gene encoding the desired constant region (or a portion thereof). Ig constant regions (heavy and light chain) can be obtained from antibody-producing cells by standard gene cloning techniques. Genes for the two classes of human light chains and the five classes of human heavy chains have been cloned, and thus, constant regions of human origin are readily available from these clones.

The fused gene encoding the hybrid IgH chain is assembled or inserted into expression vectors for incorporation into a recipient cell. The introduction of gene construct into plasmid vectors can be accomplished by standard gene splicing procedures.

The chimeric IgH chain can be co-expressed in the same cell with a corresponding L chain so that a complete immunoglobulin can be expressed and assembled simultaneously. For this purpose, the heavy and light chain constructs can be placed in the same or separate vectors.

Recipient cell lines are generally lymphoid cells. The preferred recipient cell is a myeloma (or hybridoma). Myelomas can synthesize, assemble, and secrete immunoglobulins encoded by transfected genes and they can glycosylate polypeptide. A particularly preferred recipient cell is the Sp2/0 myeloma which normally does not produce endogenous immunoglobulin. When transfected, the cell will produce only Ig encoded by the transfected gene constructs. Transfected myelomas can be grown in culture or in the peritoneum of mice where secreted immunoconjugate can be recovered from ascites fluid. Other lymphoid cells such as B lymphocytes can be used as recipient cells.

There are several methods for transfecting lymphoid cells with vectors containing the nucleic acid constructs encoding the chimeric Ig chain. A preferred way of introducing a vector into lymphoid cells is by spheroblast fusion (see Gillies et al., *Biotechnol.,* 7, 798–804 (1989)). Alternative methods include electroporation or calcium phosphate precipitation.

Other useful methods of producing the immunoconjugates include the preparation of an RNA sequence encoding the construct and its translation in an appropriate in vivo or in vitro system.

Methods for purifying recombinant immunoglobulins are well known. For example, a well known method of purifying antibodies involves protein A purification because of the propensity of protein A to bind the Fc region of antibodies. The antigen binding activity of the purified immunoconjugates can then be measured by methods well known to the art, such as described in Gillies et al. (*J. Immunol. Methol.,* 125, 191 (1989)). For example, immunoconjugate activity can be determined using antigen-coated plates in either a direct binding or competition assay format.

In particular, it is preferred that humanized antibodies are prepared and then assayed for their ability to bind antigen. Methods to determine the ability of the humanized antibodies to bind antigen may be accomplished by any of numerous known methods for assaying antigen-antibody affinity. For example, the murine antibody NR-LU-13 binds an approximately 40 kilodalton glycoprotein expressed on numerous carcinomas. This antigen has been characterized in Varki et al., *Cancer Res.,* 44, 681 (1984); Okabe et al., *Cancer Res.* 44, 5273 (1989). Thus, it is routine to test the ability of humanized antibodies to bind the NR-LU-13 antigen. Moreover, methods for evaluating the ability of antibodies to bind to epitopes of this antigen are known.

Humanized antibodies (or fragments thereof) are useful tools in methods for therapeutic purposes. When determining the criteria for employing humanized antibodies or antibody conjugates for in vivo administration for therapeutic purposes, it is desirable that the general attainable targeting ratio is high and that the absolute dose of therapeutic agent delivered to the tumor is sufficient to elicit a significant tumor response. Methods for utilizing the humanized antibodies can be found, for example, in U.S. Pat. Nos. 4,877,868, 5,175,343, 5,213,787, 5,120,526, and 5,202,169.

To target vascular smooth muscle cells (VSMC), VSMC binding proteins, e.g., polypeptides or carbohydrates, proteoglycans and the like, that are associated with the cell membranes of vascular smooth muscle cells can be employed to prepare therapeutic conjugates. In a preferred embodiment, the binding moiety is exemplified by chondroitin sulfate proteoglycans (CSPGs) synthesized by vascular smooth muscle cells and pericytes, and a discrete portion (termed an epitope herein) of the CSPG molecule having an apparent molecular weight of about 250 kD is especially preferred. The 250 kD target is an N-linked glycoprotein that is a component of a larger 400 kD proteoglycan complex. In one presently preferred embodiment of the invention, a vascular smooth muscle binding protein is provided by NR-AN-01 monoclonal antibody (a subculture of NR-ML-05) that binds to an epitope in a vascular smooth muscle CSPG target molecule. The monoclonal antibody designated NR-ML-05 reportedly binds a 250 kD CSPG synthesized by melanoma cells (Morgan et al., U.S. Pat. No. 4,897,255). Smooth muscle cells and pericytes also reportedly synthesize a 250 kD CSPG as well as other CSPGs. NR-ML-05 binding to smooth muscle cells has been disclosed (Fritzberg et al., U.S. Pat. No. 4,879,225). Subculture NR-ML-05 No. 85–41–41-A2, freeze # A2106, has been deposited with the American Type Culture Collection, Rockville, Md. and granted Accession No. HB-9350. NR-ML-05 is the parent of, and structurally and functionally equivalent to, subclone NR-AN-01, disclosed herein. It will be recognized that NR-AN-01 is just one example of a vascular smooth muscle binding protein that specifically associates with the 400 kD CSPG target, and that other binding proteins associating with this target and other epitopes in this target are also useful in the therapeutic conjugates and methods of the invention.

It will be recognized that the inventors also contemplate the utility of human monoclonal antibodies or "humanized" murine antibody as a vascular smooth muscle binding protein in the therapeutic conjugates of their invention. For example, murine monoclonal antibody may be "chimerized" by genetically recombining the nucleotide sequence encoding the murine Fv region (i.e., containing the antigen binding sites) with the nucleotide sequence encoding a human constant domain region and an Fc region, e.g., in a manner similar to that disclosed in European Patent Application No. 0,411,893 A2. Humanized vascular smooth muscle binding partners will be recognized to have the advantage of decreasing the immunoreactivity of the antibody or polypeptide in the host recipient, which may thereby be useful for increasing the in vivo half-life and reducing the possibility of adverse immune reactions. See also, N. Lonberg et al. (U.S. Pat. Nos. 5,625,126; 5,545,806; and 5,569,825); and Surani et al. (U.S. Pat. No. 5,545,807).

Useful binding peptides for cancer treatment embodiments of the present invention include those associated with cell membrane and cytoplasmic epitopes of cancer cells and the like. These binding peptides localize to the surface membrane of intact cells and internal epitopes of disrupted cells, respectively, and deliver the therapeutic agent for assimilation into the target cells. Minimal peptides, mimetic organic compounds and human or humanized antibodies that localize to the requisite tumor cell types are also useful as binding peptides of the present invention. Such binding peptides may be identified and constructed or isolated in accordance with known techniques. Preferred binding peptides of these embodiments of the present invention bind to a target epitope with an association constant of at least about $10^{-6}$M.

Methods useful to prepare antibody-peptide conjugates are well known to the art. See, for example U.S. Pat. No. 5,650,150, the disclosure of which is incorporated by reference herein. Representative "coupling" methods for linking the therapeutic agent through covalent or non-covalent bonds to the targeting moiety include chemical cross-linkers and heterobifunctional cross-linking compounds (i.e., "linkers") that react to form a bond between reactive groups (such as hydroxyl, amino, amido, or sulfhydryl groups) in a therapeutic agent and other reactive groups (of a similar nature) in the targeting moiety. This bond may be, for example, a peptide bond, disulfide bond, thioester bond, amide bond, thioether bond, and the like. In one illustrative example, conjugates of monoclonal antibodies with drugs have been summarized by Morgan and Foon (Monoclonal Antibody Therapy to Cancer: Preclinical Models and Investigations, *Basic and Clinical Tumor Immunology*, Vol. 2, Kluwer Academic Publishers, Hingham, Mass.) and by Uhr, *J. of Immunol.* 133:i-vii, 1984). In another illustrative example where the conjugate contains a radionuclide cytostatic agent, U.S. Pat. No. 4,897,255, Fritzberg et al., incorporated herein by reference, is instructive of coupling methods that may be useful. In one embodiment, the therapeutic conjugate contains a vascular smooth muscle binding protein coupled covalently to a chemokine peptide or variant. In this case, the covalent bond of the linkage may be formed between one or more amino, sulfhydryl, or carboxyl groups of the vascular smooth muscle binding protein and the chemokine peptide or variant.

In a preferred embodiment of the invention, an antibody conjugate is used in pretargeting methods. Essentially, such pretargeting methods are characterized by an improved targeting ratio or increased absolute dose to the target cell sites in comparison to conventional cancer diagnosis or therapy. A general description of pretargeting methods may be found in U.S. Pat. Nos. 4,863,713, 5,578,287, and 5,630,996. Typical pretargeting approaches are summarized below.

Pretargeting methods are of two general types: three-step pretargeting methods and two-step pretargeting methods. A three-step pretargeting protocol includes the administration of a targeting moiety-ligand conjugate, which is allowed to localize at a target site and to dilute in the circulation. This is followed by administration of an anti-ligand which binds to the targeting moiety-ligand conjugate and clears unbound targeting moiety-ligand conjugate from the blood, as well as binds to targeting moiety-ligand conjugate at the target site. Thus, the anti-ligand fulfills a dual function by clearing targeting moiety-ligand conjugate not bound to the target site as well as attaches to the target site to form a targeting moiety-ligand: anti-ligand complex. Finally, a therapeutic agent-ligand conjugate that exhibits rapid whole body clearance is administered.

When the therapeutic agent-ligand conjugate in circulation comes into close proximity to the targeting moiety-ligand: anti-ligand complex bound to the target site, the anti-ligand portion of the complex binds to the ligand portion of the circulating therapeutic agent-ligand conjugate, thus producing a targeting moiety-ligand: anti-ligand: ligand-therapeutic agent "sandwich" at the target site. Furthermore, because the unbound therapeutic agent is attached to a rapidly clearing ligand (rather than a slowly clearing targeting moiety, such as antibody or antibody fragment), this technique provides decreased non-target exposure to the active agent.

Alternatively, two-step pretargeting methods eliminate the step of administering the above identified anti-ligand. These "two-step" procedures feature targeting moiety-ligand or targeting moiety-anti-ligand administration, followed by the administration of a therapeutic agent which is conjugated to the opposite member of the ligand/anti-ligand pair.

As an optional step in the two-step pretargeting method, ligand or anti-ligand, designed specifically to provide a clearance function, is administered to facilitate the clearance of circulating targeting moiety-ligand or targeting moiety-anti-ligand. Thus, in the two-step pretargeting approach, the clearing agent does not become bound to the target cell population, either directly or through the previously administered target cell bound targeting moiety-anti-ligand or targeting moiety-ligand conjugate.

A targeting moiety in a pretargeting method binds to a defined target cell population, such as tumor cells. Preferred targeting moieties useful in this regard are antibodies (polyclonal or monoclonal), such as human monoclonal antibodies, or "humanized" murine or chimeric antibodies. Some examples of humanized antibodies include those that are CHO produced, produced in hosts such as plant (for example corn, soybean, tobacco, and the like), insect, mammalian, yeast, and bacterial. The humanized antibodies may be those that bind to the antigen bound by antibody NR-LU-13. Preferably, the humanized antibody may not possess N-linked glycosylation or its N-linked glycosylation has been modified post expression to reduce immunogenicity or toxicity.

Ligand/anti-ligand pairs suitable for use in targeting protocols include biotin/avidin or streptavidin, haptens and epitopes/antibody, fragments or analogs thereof, including mimetics, lectins/carbohydrates, zinc finger proteins/dsDNA fragments, enzyme inhibitors/enzymes; and analogs and derivatives thereof. Preferred ligands and anti-ligands bind to each other with an affinity of at least about $K_A \geq 10^9 M^{-1}$ or $K_D \leq 10^{-9} M$. Biotin/avidin or streptavidin is a preferred ligand/anti-ligand pair.

In general, such pretargeting methods preferably include the administration of an anti-ligand that provides a clearance function. The clearance is probably attributable to cross-linking and/or aggregation of conjugates that are circulating in the blood, which leads to complex/aggregate clearance by the recipient's RES (reticuloendothelial system). The anti-ligand clearance of this type is preferably accomplished with a multivalent molecule. However, a univalent molecule of sufficient size to be cleared by the RES on its own could also be employed.

Alternatively, receptor-based clearance mechanisms, e.g., Ashwell receptor or other receptors, may be exploited by addition of hexose residues, such as galactose or mannose residues, to provide for clearance of the anti-ligand, anti-ligand conjugate or humanized antibody via the liver. Such clearance mechanisms are less dependent upon the valency of the clearing agent than the RES complex/aggregate clearance mechanisms described above.

For example, if the targeting moiety-ligand or targeting moiety-anti-ligand has been derivatized to provide for clearance (i.e., addition of a hexose residue) a clearing agent should not be necessary. Preferred clearing agents are disclosed in U.S. Pat. Nos. 5,624,896 and 5,616,690; as well as PCT Application Publication Number WO 95/15978.

One skilled in the art, based on the teachings herein and the applications referenced herein, can readily determine an effective therapeutic effective dosage and treatment protocol. This will depend upon factors such as the particular selected therapeutic agent, route of delivery, the type of target site(s), affinity of the targeting moiety for target site of interest, any cross-reactivity of the targeting moiety with normal tissue, condition of the patient, whether the treatment is effected alone or in combination with other treatments, among other factors.

For example, in the case of humanized antibody—avidin or streptavidin conjugates in pretargeting strategies, a suitable dosage ranges from about 10 to about 2500 mg, more preferably from about 50 to 1500 mg, and most preferably from about 100 to 800 mg. The dosage of the ligand-therapeutic agent conjugate, generally ranges from about 0.001 to about 10 mg and more preferably from about 0.1 to 2 mg.

In general, such pretargeting methods include the administration of a clearing agent. The dosage of the clearing agent is an amount which is sufficient to substantially clear the previously administered conjugate from the circulation, i.e., at least about 50%, more preferably at least about 90%, and most preferably approaching or at 100%. In general, the clearing agent is administered several days after administration of the humanized antibody—streptavidin conjugate, preferably about 1 to 5 days after, more preferably at least about 1 to 2 days after. Generally, the determination of when to administer the clearing agent depends on the target uptake and endogenous clearance of targeting moiety conjugate. Particularly preferred clearing agents are those which provide for Ashwell receptor mediated clearance, such as galactosylated proteins, e.g., galactosylated biotinylated human serum albumin (HSA) and small molecule clearing agents containing galactose and biotin. In the case of HSA based clearing agents, a typical dosage of the clearing agent will range from about 100 to 1000 mg, and more preferably about 200–500 mg. If a clearing agent is administered, the ligand-therapeutic agent conjugate is preferably administered about 2 to 12 hours after.

The conjugates may be administered by known methods of administration. Known methods of administration include, by way of example, intraperitoneal injection, intravenous injection, intramuscular injection, intranasal administration, among others. Intravenous administration is generally preferred.

III. Indications Amenable to Treatment by the Agents of the Invention

The agents of the invention are useful to treat a mammal afflicted with, or to inhibit in a mammal at risk of, an indication associated with chemokine-induced activity, such as aberrant or pathological inflammatory processes. The chemokines participate in a broad range of inflammatory processes, both physiological and pathological. Thus, broad specificity chemokine inhibitors may be useful to treat or prevent a wide range of inflammatory diseases. Moreover, the use of rationally designed chemokine inhibitors, i.e., inhibitors with relative specificity for various chemokines, may reduce or inhibit side-effects associated with chronic therapies of broad spectrum chemokine inhibitors. Thus, these inhibitors may be designed to treat particular diseases, thereby minimizing side effects resulting from disrupting unrelated physiological processes.

Atherosclerosis. Development of atherosclerosis is a complex process involving smooth muscle cells, endothelial cells and inflammatory cells, and, in particular, monocyte-derived tissue macrophages. Once endothelial cells are activated, they express adhesion molecules important for the extravasation of inflammatory cells. For example, in the TGFβ1 knockout (-/-) mouse, the absence of this cytokine resulted in endothelial cell activation. The activated endothelial cells express, among other adhesion molecules, E-selectin, P-selectin, and ICAM-1, which in turn participate in the extravasation of leukocytes. Potent proinflammatory cytokines were also expressed at the sites of incipient vascular lesions. TNF-α, IL-1, as well as several chemokines including IL-8 and MCP-1, have been detected at elevated levels in atherosclerotic lesions. Results described hereinabove show that the chemokine MCP-1 in particular plays a role in atherosclerotic vascular inflammation.

It is now well accepted that the acute stability of vascular lesions is a more important determinant of short-term, e.g., less than several years, risk of myocardial infarction than is total plaque burden. The degree of macrophage infiltration is probably the major determinant of relative plaque stability. At least two factors contribute to plaque stability: macrophages secrete an excess of matrix-degrading enzymes (such as the matrix metalloproteinases) over their inhibitors, resulting in the loss of extracellular matrix (ECM) in the macrophage-rich shoulder and fibrous cap regions, a common feature of unstable or ruptured plaques; and macrophage-derived foam cells become necrotic, possibly in response to toxic oxidative metabolites of lipids, resulting in a lipid-filled extracellular pool which further destabilizes the local vessel wall architecture.

Inhibitors of chemokine action, and in particular inhibitors of MCP-1, may improve plaque stability and thus rapidly reduce the risk of myocardial infarction, without necessarily reducing the total atherosclerotic plaque burden. Thus, agents of the invention, e.g., peptide 3(1–12)[MCP-1] (SEQ ID NO:1), KQK, peptide 3[7–12] (SEQ ID NO:9), as well as variants, e.g., leu$_4$ile$_{11}$peptide 3(1–12)[MCP-1 ] (SEQ ID NO: 14), or derivatives thereof, may be useful to treat and/or prevent unstable angina pectoris, atherosclerosis, as well as other diseases characterized by local or systemic vasculitis, as well as the symptoms and diseases which occur secondarily to the vessel wall inflammation such as myocardial infarction.

Moreover, the agents of the invention are also useful in combination with lipid lowering agents, such as the statins, or TGF-beta elevating agents (see, for example, WO 96/40098, the disclosure of which is incorporated by reference herein).

Osteoporosis. Low bone mineral density, often categorized as osteoporosis, results from an imbalance between bone matrix deposition by osteoblasts and its subsequent resorption by osteoclasts. The balance between these two dynamic processes determines bone density. One strategy to increase bone density has been the use of analogs of tamoxifen, such as raloxifene, which mimic the effects of estrogen on bone and thus, promote osteoblast differentiation (increasing bone matrix deposition) and inhibit osteoclast recruitment (decreasing resorption). An alternative strategy is to decrease matrix resorption by directly inhibiting the mechanism by which osteoclasts are recruited to the bone. Measurement of bone matrix degradation products (such as the N-terminal and C-terminal telopeptides of collagen as well as pyridinium cross-links) in plasma and urine confirm that bone resorption is increased in osteoporosis, and hence inhibition of osteoclast activity is likely to prove an effective therapeutic strategy.

Unlike osteoblasts, which are locally derived, osteoclasts are continuously recruited to bone as precursor cells which circulate in the monocyte fraction, and which may be identical to monocytes. Once recruited, the precursors differentiate into osteoclasts which then resorb matrix until they die by apoptosis. Thus, the number of osteoclasts in bone tissue (and hence the osteoclast activity) can be rapidly regulated by modulating the osteoclast recruitment process.

A number of lines of evidence now suggest that the monocyte recruitment into bone is a molecular parallel of the pathological monocyte recruitment into the blood vessel wall that occurs during atherogenesis. In particular, the chemokine MCP-1 is implicated in both processes. Thus, MCP-1 inhibitors may act to reduce monocyte recruitment and thus decrease osteoclast recruitment and/or decrease the number of cells differentiating into osteoclasts, which would result in a rapid increase in bone density, for example, over a period of weeks rather than years. The ability of the present therapeutic agents to increase bone density contrasts with existing drugs which prevent a further decrease in bone density but do not increase bone density. Therefore, peptide 3, e.g., peptide 3(7–12)[MCP-1](SEQ ID NO:9), and variants (e.g., $leu_4ile_{11}$peptide 3(1–12)[MCP-1](SEQ ID NO:14), and derivatives (e.g., CRD-$Cys_{13}leu_4ile_{11}$peptide 3[MCP-1](3–12)[MCP-1]) thereof, may be useful to inhibit or prevent low bone density. In particular, derivatives with specificity for CC chemokines, such as CRD-$Cys_{13}leu_4ile_{11}$peptide 3 [MCP-1], are preferred agents for the treatment of osteoporosis.

HIV Infection and AIDS. In addition to the CD4 receptor, additional cell surface molecules (termed co-receptors) are required for the productive infection of a cell by HIV isolates. HIV isolates can be divided into two subtypes, which depend on whether they can infect monocyte/macrophages (M-tropic strains) or helper T lymphocytes (T-tropic strains). Experiments with chemokine ligands suggest that the chemokine receptors function as the HIV co-receptors: MIP1α and RANTES inhibited the infection of monocytes with M-tropic strains (but not infection of T-cells by T-tropic strains), while SDF-1 inhibited T cell infection (but not monocyte infection). Further molecular analyses confirmed that the MIP1α/RANTES receptor CCR-5 is the HIV co-receptor on monocytes while the SDF-1 receptor CXCR-4 (also termed LESTR and fusin) is the co-receptor on T-cells. Early in infection, M-tropic virus predominates, a virus which is non-syncytium forming, less virulent and does not deplete T-cells. At a later time, selection favors conversion to the more virulent, syncytium forming T-tropic strain, a strain which depletes helper T cells and leads to acquired immunodeficiency (AIDS). It is possible that the virions can use other chemokine receptors, although at lower efficiency. Thus, to provide an effective agent to inhibit HIV, the agent preferably inhibits virus binding to more than one receptor, i.e., an agent would have to have broad specificity for chemokine receptors.

Genetic studies have identified a mutation in CCR5 which renders individuals essentially immune to HIV infection. This mutation, termed CCR5Δ32, results in a truncated mRNA for CCR-5. The expression of the truncated CCR-5 does not produce any detectable CCR-5 protein on the cell surface. Individuals homozygous for this deficiency have been reported to be entirely resistant to HIV infection, even under exposure to extremely high viral challenge, although there is now a single report of a homozygous mutant individual seropositive for HIV infection. Thus, these observations demonstrate that effective blockade of the CCR-5 receptor may effectively prevent infection. Moreover, CCR-5 mediated chemokine signaling does not have a crucial role in normal physiology, since CCR-5Δ32 homozygotes have no detectable phenotype other than HIV resistance.

Therefore, inhibitors of chemokine receptors, such as peptide 3, its variants or derivatives, may inhibit HIV infection as these agents have broad specificity. As described hereinbelow (Example 5), peptide 3[MCP-1] inhibited HIV binding and infection of Jurkat cells. A preferred agent to prevent or inhibit HIV infection and/or replication is CRD-$Cys_{13}leu_4ile_{11}$peptide 3[MCP-1]. Low doses of peptide 2, its analogs or derivatives, may also be useful to prevent or inhibit HIV infection and/or replication.

Thus, these agents are useful for the treatment, as well as the prevention, of both HIV seropositives and of progression of patients to AIDS, when used, either alone, or in combination with other anti-viral therapies. When used in combination, it is preferred that an infected individual is pre-treated with viral inhibitors (such as a cocktail of reverse transcriptase and viral protease inhibitors) and then given doses of a general chemokine inhibitor, preferably peptide 3, peptide 2, their variants or derivatives, more preferably peptide 2[MIP1α], its analogs or derivatives. Moreover, since resistance to other therapies (such as protease inhibitors or reverse transcriptase inhibitors) arise because of viral replication, agents which reduce virus infectivity may drastically increase the success of these existing therapies. Specifically, unlike all currently exploited therapeutic targets such as reverse transcriptase or the viral protease, chemokine agonists and/or antagonists target the susceptible cell rather than the virus itself. Although the virus can rapidly mutate to generate strains resistant to the virus-targeted agents, cells mutate less readily and are under less or no selective pressure to mutate. The extent to which the mutations in the HIV virus must occur to circumvent the use of a chemokine co-receptor is likely to be much greater than the mutations necessary to render a reverse transcriptase resistant to a reverse transcriptase inhibitor. Thus, the administration of chemokine analogs is likely to prove effective either alone or in combination with the virus-targeted therapies. Furthermore, chemokine inhibitors may have limited side effects in vivo, i.e., limited physiological impact, and therefore have a good therapeutic index when used in vivo.

Malaria. Malaria is caused by intracellular parasites of the plasmodium group. The main cellular target of the parasite is the red blood cell, and the mechanism of infection involves interaction of a plasmodium surface protein and the Duffy Antigen Receptor for Chemokines (DARC) for at least one common plasmodium species, *P. vivax*. Studies have indicated that normal surface presentation of DARC on the red blood cell surface is necessary for plasmodium entry. Consequently, inhibitors of DARC function may be useful anti-malarial agents. Hence, peptide 3, or preferably a derivative showing higher affinity DARC binding such as $ser7glu_8glu_9$peptide 3(1–12)[MCP-1](SEQ ID NO:12), or more preferably, a peptide which shows high affinity DARC binding and does not inhibit chemokine activity such as peptide 2[MCP-1], are examples of agents falling under the scope of this invention which are useful for the prevention and treatment of malaria.

Peptide 2, peptide 2 variants and derivatives are proinflammatory agents. Thus, these agents are useful to augment inflammatory responses, in particular weak inflammatory responses which are often associated with persistent infections such as parasitic infection, e.g., intracellular parasites.

Psoriasis. Psoriasis is an inflammatory disorder that is associated with MCP-1 and monocyte recruitment. Topical application of a therapeutic agent of the invention, e.g., peptide 3, is preferred to prevent or treat psoriasis as this delivery method reduces bioavailability problems. Derivatives of the therapeutic agents of the invention, e.g., CRD peptides, which are administered topically may exhibit enhanced bioavailability relative to non-derivatized counterparts.

Autoimmune Diseases. Autoimmune diseases, such as multiple sclerosis, Crohn's disease, rheumatoid arthritis and systemic lupus erythematosus, are characterized by inappropriate activation of the immune system, orchestrated by autoreactive leukocytes. Although it remains unclear what factors lead to the initial inappropriate recognition of self-antigens, a number of pro-inflammatory cytokines have been implicated in the continuing inflammation which underlies the tissue destruction that, in turn, leads to the morbidity and mortality associated with these diseases. Of these inflammatory cytokines, TNF-α and the chemokines (in particular MIP-1α) have been implicated.

For example, elevated MIP-1α expression is detected in experimental autoimmune encephalomyelitis, a model of T-cell mediated autoimmune disease with some common characteristics to human multiple sclerosis. Elevated MIP1α activity is also detected in the cerebrospinal fluid of patients with multiple sclerosis. Antibody therapy to reduce chemokine levels has been shown to be effective in animal models of autoimmune diseases, but this method only lowers chemokine levels for a short period, and is unlikely to be useful in human therapy. In contrast, a general antagonist of chemokine signaling is likely to suppress the inappropriate inflammation indefinitely. Thus, peptide 3, its derivatives and variants, may be useful to prevent and/or treat autoimmune disorders including, but not limited to, type I diabetes, multiple sclerosis, rheumatoid arthritis and systemic lupus erythematosus.

Moreover, different chemokine expression patterns may be associated with different autoimmune disorders, and hence each autoimmune disease may require a different derivative or variant of peptide 3. For example, MIP1α may play a central role in multiple sclerosis. MIP1α is a CC chemokine. Thus, the administration of a CC-selective agent of the invention can be used to treat multiple sclerosis (e.g., $Leu_4Ile_{11}$peptide 3(1–12)[MCP-1] (SEQ ID NO:14) or $Ser_7Glu_8Glu_9$peptide 3(1–12)[MCP-1](SEQ ID NO:12).

Wound Healing. Following wounding, there is a complex process of wound healing involving recruitment and proliferation of different cell types, elaboration of matrix, and increased immune surveillance. In the fetus (where increased immune surveillance is not required) this wound healing process leads to complete restoration of the normal tissue architecture (e.g., normal dermal architecture is restored after incisional wounding). In marked contrast, in the adult, incisional wounding results in a wound healing process that does not restore normal dermal architecture. Matrix is elaborated in excess amounts and in inappropriate spatial organization. The result is a scar. In some cases, such as in children following severe wounding such as from burns, the scars are hypertrophic having huge excess of matrix deposition and are particularly disfiguring.

In adults, the risk of infection following wounding is high. Leukocytes, particularly neutrophils, are recruited rapidly to the wound site, while monocyte/macrophages appear several days after wounding, resulting in a rapid formation of granulomatous tissue. Studies with antibodies have suggested that CXC chemokines such as IL-8 play an important role in neutrophil attraction to the wound site, and that inhibition of IL-8 production reduces both neutrophil accumulation and subsequent scarring. Experiments blocking CC chemokines have similarly shown that they have a role in the attraction of macrophages to the wound site, and these cells may also promote rapid healing at the expense of wound quality. Hence inhibition of either CXC or CC chemokines, or both, may result in a decrease in the wound-induced inflammatory reaction, and in turn promote a balance between fast healing and good restoration of dermal architecture.

To prevent or reduce scarring and/or enhance wound healing, a preferred embodiment of the invention is the topical application of a therapeutic agent of the invention that inhibits chemokine action at the site of the wound. Thus, a broad spectrum chemokine inhibitor, such as peptide 3(1–12)[MCP-1](SEQ ID NO:1), $leu_4ile_{11}$peptide 3(1–12) [MCP-1](SEQ ID NO:14), CRD-$leu_4$-$ile_{11}$peptide 3[MCP-1] or WVQ, or combinations thereof may be administered. Alternatively, a selective inhibitor of IL-8, such as KEN, or a selective inhibitor of MCP-1, such as KQK, as well as combinations thereof may be administered. In addition, a combination of a broad spectrum inhibitor and a selective inhibitor may be administered. In this way, the various components of the wound-induced inflammatory process may be controlled as desired and the wound may be allowed to heal more slowly (under conditions where it is protected from infection, e.g., by simultaneous use of antibiotics) but with enhanced recovery of dermal architecture. See U.S. Pat. No. 5,202,118 for methods to determine the efficacy of an agent to treat or enhance wound healing.

Tuberculosis. Infection with *Mycobacterium tuberculosis* is an example of a disease where the monocyte/macrophage is responsible for attempting to clear the pathogen from the host tissue (in this case the lung) but where the immune response is often insufficient. As a consequence, even when antibiotics are used, *M. tuberculosis* infection can persist, clinically or sub-clinically as the body fails to clear the entire pathogen load.

Thus, diseases such as tuberculosis are amenable to therapy by agents which augment the existing immune reaction to recruit additional monocytes to the target tissue. Agents which illicit a systemic inflammation are less useful because the systemic inflammation has side effects (e.g., nausea, high temperature, lethargy, etc.). Thus, agents which bind to DARC with high affinity, may be useful as these agents may augment an existing inflammatory reaction but do not result in systemic inflammation. Since DARC normally acts to limit the extent of a local inflammatory reaction by sequestering locally produced chemokines, agents which reduce or block the capacity for DARC to sequester the chemokines may augment the desired response. Thus, one embodiment of the invention is the administration of a DARC binding agent, e.g., peptide 2[MCP-1], either locally to the lungs or systemically, to reduce or inhibit DARC sequestration of chemokines. Increased local chemokine levels can augment monocyte recruitment, and the resultant increase in the number of tissue macrophages may aid clearance of *M. tuberculosis* and reduce or prevent chronic infection.

The agent of the invention may be administered either alone, or more preferably, in combination with antibiotics or other drugs which have been shown to inhibit the growth of *M. tuberculosis*, but which when used singly may not prevent or abolish chronic infection.

Agents such as peptide 2[MCP-1] which augment existing immune reactions may also be useful for reduction or elimination of other chronic or parasitic infections, e.g., leishmania, trypanosomes, leprosy, and the like.

Basophil-mediated diseases. Asthma is a disease characterized by hyper-reactive airways and chronic inflammation resulting from an influx of many cell types and inflammatory mediators. The interaction and causal effects of all the inflammatory mediators in asthma is not entirely understood. MCP-1 can play a role in asthma through several different effector functions such as: monocyte recruitment, basophil recruitment, lymphocyte recruitment, monocyte activation or by triggering the release of histamine from basophils or resident mast cells (Bischoff et al., *J. Exp. Med.*, 175(5), 1271 (1992)). Inhibition of these processes are likely to reduce the severity of the disease. Allergic diseases, like asthma, are manifested through a complex interaction of inflammatory mediators including monocytes/macrophages, lymphocytes and histamine release from mast cells and basophils.

A preferred mode for administration of a therapeutic agent of the invention to treat or inhibit the symptoms associated with asthma is by inhalation. As red blood cells are not normally present in the respiratory tract, the DARC specificity of the therapeutic agent is less important for administration to the respiratory tract than for other modes of administration.

Endotoxemia. Endotoxemia is an acute systemic illness often mediated by LPS, a major component in the cell wall of gram-negative bacteria. LPS stimulates the release of proinflammatory cytokines. MCP-1 and MCP-2 are expressed in endotoxemia and exert their effect by recruiting leukocytes to target organs. The intraperitoneal administration of recombinant murine MCP-1 to LPS-challenged mice protected them from endotoxic lethality (Zisman et al., *J. Clin. Invest.*, 99, 2832 (1997)).

Myocardial Infarction/Acute Ischemia. Myocardial infarction is the result of acute closure of a coronary vessel usually due to thrombosis secondary to rupture of an atherosclerotic plaque. The damage to the adjacent myocardium and resultant heart failure is secondary to the period of ischemia and the damage caused during the reperfusion period. Reperfusion injuries are associated with increased oxygen free radicals and inflammatory mediators. MCP-1 is up-regulated during the reperfusion period and is a key inflammatory mediator (Kumar et al., *Circulation*, 90, 1427 (1994); Kumar et al., *Circulation*, 95, 693 (1997)). Inhibition of MCP-1 and the resultant inflammatory input may decease damage to the myocardium during recovery and reduce the incidence of heart failure.

Rheumatoid Arthritis. Rheumatoid arthritis is a multi-systemic inflammatory disease involving primarily the joints but also the skin, blood vessels, heart, lung and muscle. The characteristic pathology of rheumatoid arthritis involves the accumulation of non-suppurative inflammatory cell infiltrate consisting of macrophages and lymphocytes within the joint. MCP-1 is produced by both synovial cells and infiltrating monocyte/macrophages in rheumatoid arthritis and is thought to contribute to the accumulation of inflammatory cells within the joint. The ability of native MCP-1 and an antagonist of MCP-1 (residues 9–76 of native MCP-1) have been assessed in the MRL-lpr model of chronic arthritis. Treatment with the antagonist MCP-1 (9–76) but not native MCP-1 resulted in a reduction of the symptoms and histopathology of chronic arthritis in this model (Gong et al., *J. Exp. Med.*, 186, 131 (1997); Plater-Zyberk et al., *Immunol. Lett.*, 57, 117 (1997); Wilder, *Clin. Rheumat.*, 10, 259 (1996)).

IV. Dosages, Formulations and Routes of Administration of the Agents of the Invention The therapeutic agents of the invention, including a compound of formula (I) or (II), including their salts, are preferably administered so as to achieve serum levels of about 0.01 pM to about 100 nM, more preferably at doses of about 0.01 pM to about 5 nM, and even more preferably at doses of about 0.1 pM to about 2 nM, of the therapeutic agent. To achieve these levels, the agent may be administered at dosages of at least about 0.01 to about 100 mg/kg, more preferably about 0.1 to about 50 mg/kg, and even more preferably about 0.1 to about 30 mg/kg, of body weight, although other dosages may provide beneficial results. The amount administered will vary depending on various factors including, but not limited to, the agent chosen, the disease, whether prevention or treatment is to be achieved, and if the agent is modified for bioavailability and in vivo stability.

Administration of sense or antisense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., *Immunity*, 3, 165 (1995); Stevenson et al., *Immunol. Rev.*, 145, 211 (1995); Molling, *J. Mol. Med.*, 75, 242 (1997); Donnelly et al., *Ann. N.Y. Acad. Sci.*, 772, 40 (1995); Yang et al., *Mol. Med. Today*, 2, 476 (1996); Abdallah et al., *Biol. Cell*, 85, 1 (1995)). Pharmaceutical formulations, dosages and routes of administration for nucleic acids are generally disclosed, for example, in Felgner et al., supra.

The amount of therapeutic agent administered is selected to treat a particular indication. For example, to treat malaria, higher doses of peptide 2, its variants or derivatives, may be administered, while smaller doses of peptide 2, its variants or derivatives, are useful to prevent or inhibit HIV infection. The therapeutic agents of the invention are also amenable to chronic use for prophylactic purposes, preferably by systemic administration.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the therapeutic agents of the invention, which, as discussed below, may optionally be formulated for sustained release, can be administered by a variety of routes including oral, or parenteral, including by rectal, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The local delivery of the therapeutic agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as antimicrobial agents, or preservatives. Furthermore, the active ingredients may also be used in combination with other therapeutic agents, for example, bronchodilators.

To employ the therapeutic agents of the invention to enhance the immunological response of a particular immunogen, e.g., the *Haemophilis influenza* type b (Hib) capsular polysaccharide (polyribosylribitol phosphate, PRP), the agents may be conjugated to the immunogen. Thus, for example, peptide 2(1–15)[MCP-1] (SEQ ID NO:3) may be covalently linked to PRP through a 6 carbon spacer molecule derived from adipic acid dihydrazide (see Gordon, Patent 83/4939, Republic of South Africa, 1984), and administered in a manner similar to that described in Eskola et al., *Lancet*, 1, 1184 (1985). The use of nucleic acid molecules to prepare vaccines is described in, for example, Felgner et al., supra and Stevenson et al., supra.

A vaccine of the invention may also comprise cells or viruses having nucleic acid encoding the immunogen and a peptide or variant peptide of the invention or its complement, optionally as a fusion protein.

For a general description of vaccine principles and practice, see Ada, In: *Fundamental Immunology*, $2^{nd}$ ed., Raven Press Ltd., N.Y., pp. 985–1030 (1989).

The invention will be further described by, but is not limited to, the following examples.

EXAMPLE 1

Identification and Characterization of Pan-Chemokine Peptide Inhibitors

Based on an alignment of MCP-1 sequences from different species, three regions in MCP-1 were identified which were conserved between all the species examined. Three purified (>95% purity) peptides (12–15mers) were prepared which had the greatest sequence homology between the human and mouse MCP-1 sequences (Table 3). These peptides were screened for their ability to inhibit hMCP-1 induced THP-1 migration.

For this assay, THP-1 cells were maintained at a density of $4 \times 10^5$ cells per ml in RPMI-1640 supplemented with 10% fetal calf serum+20 $\mu$M 2-mercaptoethanol. Chemotaxis was induced in a 96-well disposable chemotaxis chamber fitted with a 5 $\mu$M polycarbonate filter (PVP free, ChemoTX, Neuroprobe Inc., Cabin John). Twenty-nine $\mu$l of chemoattractant (recombinant human chemokine; 50 ng/ml, i.e., 5.9 nM) or control (100 ng/ml TGFβ) was added to the lower compartment of each well. The framed filter was aligned with the holes in the corner of the filter frame and placed over the wells. Five$\times 10^4$ THP-1 cells in 25 $\mu$l of RPMI-1640 culture media were added to the upper compartment. Peptides were dissolved in Milli Q water and then serially diluted in culture medium. In most cases, the serially diluted peptides were added to the upper compartment of the chemotaxis chamber. The chamber was incubated at 37° C. in a humidified atmosphere of 5% $CO_2$ for 4 hours.

After incubation, the cells were gently removed from the top of the filter with a pipette, 20 $\mu$l of 20 mM EDTA in PBS was added into each top well, and the mixture was incubated for 20 minutes at 4° C. The filter was then carefully flushed with media using a gentle flow, and removed. A standard curve was prepared to accurately quantify the number of THP-1 cells that had migrated. The curve was based on a two-fold dilution series of THP-1 cells (top standard 100, 000 cells in 29 $\mu$l). Cells which had migrated, and in separate wells, the cells in the standards, were stained with 3 $\mu$l of MTT stock solution which was added directly into each well (5 mg/ml in RPMI 1640 without phenol red, Sigma Chemical Co.) and incubated at 37° C. for 4 hours. The media was carefully aspirated from each well, and the converted dye was solubilized by 20 $\mu$l of DMSO. Absorbance of converted dye was measured at a wavelength of 595 nM using an ELISA plate reader. The number of cells that had migrated in each well was determined by interpolation of the standard curve.

Peptide 1[MCP-1] (see Table 3; SEQ ID NO:2), i.e., the N-terminal peptide of human MCP-1, was only weakly active in the migration assay ($ED_{50}$>100 $\mu$M; 10% inhibition at 100 $\mu$M, p=0.27). Peptide 2[MCP-1] (Table 3; SEQ ID NO:3) was also a weak inhibitor of chemokine-induced migration ($ED_{50}$>100 $\mu$M; 19% inhibition at 100 $\mu$M, p=0.09). Thus, in the presence of a strong agonist, i.e., MCP-1, peptide 2[MCP-1] having SEQ ID NO:3, a weak agonist, displaces MCP-1 from its receptor. However, in the absence of a strong agonist, i.e., MCP-1, peptide 2[MCP-1] exhibited weak agonist properties, i.e., peptide 2[MCP-1] stimulated chemotaxis.

Figure 2:
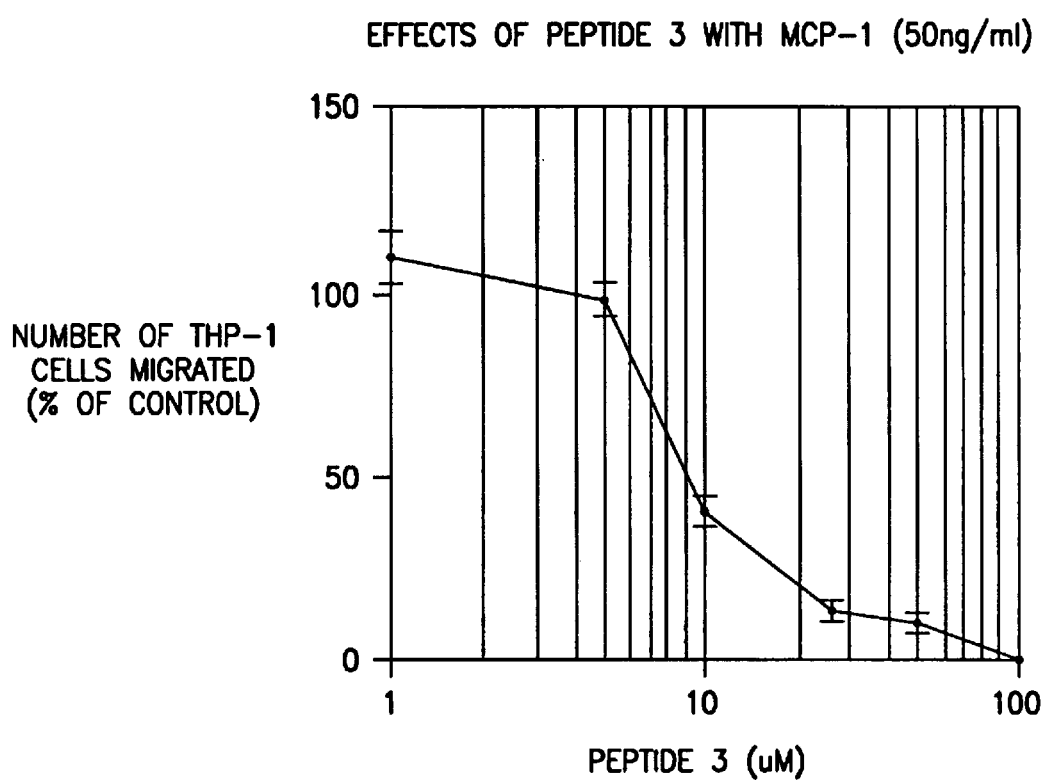
FIG. 2 shows a dose-response curve for the peptide 3 (SEQ ID NO:1) inhibition of MCP-1-induced THP-1 cell migration.

In contrast, peptide 3(1–12)[MCP-1] (Table 3; SEQ ID NO:1) was a highly effective inhibitor of MCP-1 induced THP-1 migration with a dose giving 50% inhibition ($ED_{50}$) of 8±1 $\mu$M (n=4). A typical dose response curve is shown in FIG. 2. At concentrations above 50 $\mu$M, peptide 3(1–12) [MCP-1] having SEQ ID NO:1 abolished all of the MCP-1 induced THP-1 migration.

TABLE 3

| Alignment of Chemokine Sequences | | | | | | | |
|---|---|---|---|---|---|---|---|
| AQPDAINAPV | TCCYNFTNRK | ISVQRLASYR | RITSSKCPKE | AVIFKTIVAK | EICADPKQKW | VQDSMDHLDK |
| ***.* | **. | * . | ***. |  * .. | *.***** * |  . |
| AQPDAVNAPL | TCCYSPTSKM | IPMSRLESYK | RITSSRCPKE | AVVFVTKLKR | EVCADPKKEW | VQTYIKNLDR |
| Peptide 1 | | | Peptide 2 | | | Peptide 3 |
| AQPDSVSIPI | TCCPNVINRK | IPIQRLESYR | RITNIQCPKE | AVIFKTKRGK | EVCADPKERW | VRDSNKHLDQ |
| AQPVGINTST | TCCYRFINKK | IPKQRLESYR | RITSSNCPRE | AVIFKTKLDK | EICADPTQKW | VQDFMKHLDK |
| SASLAADTPT | ACCFSYTSRQ | IPQNFIADYF | E-TSSQCSKP | GVIFLTKRSR | QVCADPSEEW | VQKYVSDLEL |

TABLE 3-continued

Alignment of Chemokine Sequences

| | | | | | | | |
|---|---|---|---|---|---|---|---|
| SAPMGSDPPT | ACCFSYTARK | LPRNFVVDYY | E-TSSLCSQP | AVVFQTKRSK | QVCADPSESW | VQEYVYDLEL | |
| SAPMGSDPPT | ACCFSYTARK | LPRNFVVDYY | E-TSSLCSQP | AVVFQTKRSK | QVCADPSESW | VQEYVYDLEL | |
| HPGIPS | ACCYNFTNKK | ISFQRLKSYK | IITSSKCPQT | AIVFEIKPDK | MICADPKxxW | VQDAKKYLDQ | |
| LPRSAKELRC | QCIKTYSKPF | HPKFIKELRV | IESGPHCANT | EIIVRLSDGR | ELCLDPKENW | VQRVEKFLKR | |
| GKPVSLSY | RCPCRFFESH | IAPANVKHLK | ILNTPNCALQ | IVARLKNNNR | QVCIDPKLKW | IQEYEKALNK | |
| ......... | .C...F.... | I......... | ..T...C... | AVI......K | .VCADP...W | VQ......L.. | |

| | | | |
|---|---|---|---|
| QTQTPKT | hMCP1 | (SEQ ID NO:16) |
| NQMR.... | mMCP1 | (SEQ ID NO:26) |
| IFQNLKP | hMCP2 | (SEQ ID NO:17) |
| KTQTPKL | hMCP3 | (SEQ ID NO:18) |
| SA | hMIP1a | (SEQ ID NO:19) |
| N | hMIP1b | (SEQ ID NO:20) |
| N | RANTES | (SEQ ID NO:21) |
| ISQxTKP | Eotaxn | (SEQ ID NO:25) |
| AENS | hIL-8 | (SEQ ID NO:23) |
| | hSDF1b | (SEQ ID NO:22) |
| ......CONSENSUS | | |

To determine whether the peptides were MCP-1 receptor antagonists, the peptides were introduced with the chemokine in the lower compartment (as opposed to with the cells in the upper compartment in the experiments described above; in the trans-well THP-1 migration assay. Under these conditions, peptide 1 [MCP-1] having SEQ ID NO:2 was a more efficient inhibitor of MCP-1 induced chemokine migration that it had been when it was incubated with the cells, inhibiting 48% of the MCP-1 induced migration at 100 $\mu$M compared to 10% inhibition when peptide 1[MCP-1] (SEQ ID NO:2) was incubated with the cells. This result is consistent with published reports which show that peptide 1[MCP-1] (SEQ ID NO:2) and its derivatives act by disrupting the MCP-1 dimer, forming inactive monomers. Peptide 1[MCP-1] (SEQ ID NO:2) is not, therefore, a classical receptor-level antagonist of MCP-1 function. In marked contrast, peptide 3(1–12)[MCP-1] having SEQ ID NO:1 was much less effective when incubated with the chemokine than with the cells (17% inhibition at 100 $\mu$M compared with >99% inhibition), suggesting that a peptide having SEQ ID NO:1 inhibits MCP-1 induced migration by direct receptor antagonism. To confirm this observation, the binding affinity of an N-terminally biotinylated derivative of peptide 3(1–12)[MCP-1] (SEQ ID NO:1) was determined. This derivative bound to the surface of THP-1 cells with a ka of about 10 $\mu$M.

Peptide 3(1–12)[MCP-1] (SEQ ID NO: 1) also inhibited other functions of MCP-1, which may be mediated by different combinations of receptors. MCP-1 has been reported to be a weak co-mitogen with 0.5% fetal calf serum for cultured smooth muscle cells. It was found that 100 $\mu$M peptide 3(1–12)[MCP-1] (SEQ ID NO:1) completely abolished the co-mitogenic effect of MCP-1 for cultured smooth muscle cells, also consistent with the hypothesis that peptide 3(1–12)[MCP-1] (SEQ ID NO:1) is an MCP-1 receptor antagonist. The observation that peptide 3(1–12) [MCP-1] (SEQ ID NO: 1) completely inhibits different responses to MCP-1 in different cell types suggests that peptide 3 may be a general antagonist of all chemokine receptors capable of binding and signaling in response to MCP-1.

To investigate the receptor specificity of peptide 3 inhibition, the $ED_{50}$ was determined for peptide 3(1–12) [MCP-1] (SEQ ID NO: 1) inhibition of THP-1 migration induced by chemokines which signal through different receptors than MCP-1 receptors. Representative chemokines included a beta-chemokine ("CC"), MIP-1$\alpha$, and two alpha-chemokines ("CXC"), IL-8 and SDF-1$\alpha$. Additionally, to determine the specificity of peptide 3(1–12)[MCP-1] (SEQ ID NO:1) for chemokine receptors, TGF-beta was selected as a migration-inducing agent unrelated to the chemokine family, and as an agent which elicits a biological activity by signaling through identified, unrelated receptors.

Peptide 3(1–12)[MCP-1] (SEQ ID NO:1) inhibited the THP-1 migration induced response to all four of the selected chemokines, with the order of potency: MIP-1$\alpha \geq$MCP-1>SDF1$\alpha \geq$IL-8 (see Table 4). In contrast, peptide 1[MCP-1] (SEQ ID NO:2) or peptide 2(1–15)[MCP-1] (SEQ ID NO:3) did not inhibit migration in response to any of these chemokines by more than 20%, even at 100 $\mu$M (Table 4).

TABLE 4

| PEPTIDE | MCP-1 | MIP1$\alpha$ | $ED_{50}$ versus IL8 | SDF-1$\alpha$ | TGF$\beta$1 |
|---|---|---|---|---|---|
| (a) $ED_{50}$ for inhibition of THP-1 migration | | | | | |
| Peptide 1 (SEQ ID NO:2) | n.s.[b] | n.s.[b] | n.s. | n.s. | n.s. |
| Peptide 2 (SEQ ID NO:3) | n.s. | n.s. | n.s. | n.s. | n.s. |
| Peptide 3[a] (SEQ ID NO:1) | 8 ± 1 | 8 ± 1 | 14 ± 1 | 10 ± 0 | n.s. |
| (b) Extent of inhibition of THP-1 migration at 100 $\mu$M | | | | | |
| Peptide 1 (SEQ ID NO:2) | n.s.[b] | n.s.[b] | n.s. | n.s. | n.s. |
| Peptide 2 (SEQ ID NO:3) | n.s. | n.s. | n.s. | n.s. | n.s. |
| Peptide 3 (SEQ ID NO:1) | 112 | 99 | 103 | 107 | n.s. |

TABLE 4-continued

| PEPTIDE | MCP-1 | MIP1α | ED$_{50}$ versus<br>IL8 | SDF-1α | TGFβ1 |
|---|---|---|---|---|---|
| (c) Extent of inhibition of human monocyte migration at 100 μM | | | | | |
| Peptide 1 (SEQ ID NO:2) | n.s. | n.s. | n.s. | n.s. | n.s. |
| Peptide 2 (SEQ ID NO:3) | 23 | n.s. | n.s. | n.s. | n.s. |
| Peptide 3 (SEQ ID NO:1) | 108 | 120 | 106 | 108 | n.s. |

[a] mean ± SEM of at least three determinations
[b] Peptide 1 caused significant inhibition only when added to the lower compartment
n.s. = no statistically significant inhibition (p > 0.05)

Furthermore, peptide 3(1–12)[MCP-1] having SEQ ID NO:1 (as well as peptide 1[MCP-1] (SEQ ID NO:2) and peptide 2(1–15)[MCP-1] (SEQ ID NO:3)) did not significantly inhibit THP-1 migration induced by TGF-beta even at 100 μM. Taken together, these results demonstrated that peptide 3(1–12)[MCP-1] (SEQ ID NO: 1) is a general and specific inhibitor of chemokine signaling. Although peptide 3(1–12)[MCP-1] (SEQ ID NO:1) shows weak selectivity for CC chemokines over CXC chemokines, nevertheless, at 100 μM, peptide 3(1–12)[MCP-1] (SEQ ID NO:1) inhibits >99% of the migration induced by any of the chemokines of either chemokine family tested (Table 4). Thus, although MCP-1 signals through multiple related receptors, peptide 3(1–12)[MCP-1] (SEQ ID NO: 1) blocks all of the receptors which participate in the chemotactic and mitogenic signaling pathways elicited by MCP-1.

To exclude the possibility that peptide 3(1–12)[MCP-1] (SEQ ID NO:1) was more effective on THP-1 cells than primary human monocytes, the effect of peptide 3(1–12)[MCP-1] (SEQ ID NO:1) on the chemokine-induced migration of freshly prepared peripheral blood monocytes from 3 donors was tested. Similar to the results for THP-1 cells, 100 μM of peptide 3(1–12)[MCP-1] (SEQ ID NO:1), but not peptide 1 [MCP-1] (SEQ ID NO:2) or peptide 2(1–15) [MCP-1] (SEQ ID NO:3), inhibited all or almost all (>95%) of the migration induced with each of the four chemokines, but did not affect TGF-beta induced migration. Thus, peptide 3(1–12)[MCP-1] (SEQ ID NO: 1) is an inhibitor of a broad range of pro-inflammatory chemokines which act on a wide range of target cells (smooth muscle cells, THP-1, Jurkat T-cell line and primary human monocytes). Note that in contrast to THP-1 cells, peptide 2(1–15)[MCP-1] (SEQ ID NO:3) inhibition of MCP-1 induced migration of primary human monocytes (20%) was statistically significant (Table 4).

EXAMPLE 2

Characterization of Subunits and Variants of Peptide 3(1–12)[MCP-1]

To determine whether a subunit of peptide 3 has biological activity and selectivity, two 6mer "half-peptides" were analyzed (Table 5): EICADP (SEQ ID NO:8), corresponding to peptide 3(1–6)[MCP-1], and KQKWVQ (SEQ ID NO:9), corresponding to peptide 3(7–12)[MCP-1]. Peptide 3(7–12) [MCP-1] (SEQ ID NO:9) was as potent an inhibitor of CC chemokine signaling as peptide 3(1–12)[MCP-1] (SEQ ID NO:1), but was noticeably more potent as an inhibitor of CXC chemokines (Table 6). In contrast, peptide 3(1–6) [MCP-1] (SEQ ID NO:8) was much less potent as an inhibitor than peptide 3(1–12)[MCP-1] (SEQ ID NO:1).

TABLE 5

| NAME | SEQUENCE | SOURCE |
|---|---|---|
| Peptide 1 family | | |
| Pep 1 | AQPDAINAPVTCC<br>(SEQ ID NO:2) | Residues 1–13 of mature hMCP-1 |
| Peptide 2 family | | |
| Pep2(1–15)[MCP1] | SYRRITSSKCPKEAV<br>(SEQ ID NO:3) | Residues 28–42 of mature hMCP-1 |
| Pep2(1–15)[SDF1] | HLKILNTPNCALQIV<br>(SEQ ID NO:4) | Residues 26–40 of mature hSDF-1β |
| Pep2(1–14)[MIPIα] | DYFETSSQCSKPGV<br>(SEQ ID NO:5) | Residues 28–41 of mature hMIPIα |
| Pep2(1–16)[IL8] | ELRVIESGPHCANTEI<br>(SEQ ID NO:6) | Residues 27–42 of mature hIL-8 |
| Peptide 3 family | | |
| Pep3(1–12)[MCP-1] | EICADPKQKWVQ<br>(SEQ ID NO:1) | Residues 50–61 of mature hMCP-1 |
| Pep3(3–12)[MCP-1] | CADPKQKWVQ<br>(SEQ ID NO:7) | Residues 52–61 of mature hMCP-1 |
| Pep3(1–6)[MCP-1] | EICADP<br>(SEQ ID NO:8) | Residues 50–55 of mature hMCP-1 |
| Pep3(7–12)[MCP-1] | KQKWVQ<br>(SEQ ID NO:9) | Residues 56–61 of mature hMCP-1 |
| Leu$_4$Pep$_3$<br>(1–12)[MCP-1] | EICLDPKQKWVQ<br>(SEQ ID NO:10) | Mutant of peptide 3 |

TABLE 5-continued

| NAME | SEQUENCE | SOURCE |
|---|---|---|
| Ser$_7$Pep$_3$ (1–12)[MCP-1] | EICADPSQKWVQ (SEQ ID NO:11) | Mutant of peptide 3 |
| Ser$_7$Glu$_8$Glu$_9$Pep$_3$ (1–12)[MCP-1] | EICADPSEEWVQ (SEQ ID NO:12) | Residues 50–61 of mature hMIP1α |
| Ile$_{11}$Pep$_3$ (1–12)[MCP-1] | EICADPKQKWIQ (SEQ ID NO:13) | Mutant of peptide 3 |
| Leu$_4$Ile$_{11}$Pep$_3$ (1–12)[MCP-1] | EICLDPKQKWIQ (SEQ ID NO:14) | Mutant of peptide 3 |
| Unrelated control peptide | | |
| Peptide C | CPSLEDSFIQVA (SEQ ID NO:15) | C-terminus of h Apo(a)RG-C protein |

TABLE 6

Effect of Mutant Sequence Peptide 3 Derivatives on THP-1 Migration

| PEPTIDE | MCP1 | MIP1α | ED$_{50}$ versus IL8 | SDF1α | TGFβ1 |
|---|---|---|---|---|---|
| Peptide 3 (SEQ ID NO:1) | 8 | 8 | 14 | 10 | n.s. |
| Peptide 3[3–12] (SEQ ID NO:7) | 8 | 7 | 9 | 9 | n.s. |
| Peptide 3[1–6] (SEQ ID NO:8) | 33 | 25 | 17 | 19 | n.s. |
| Peptide 3[7–12] (SEQ ID NO:9) | 7 | 5 | 6 | 6 | n.s. |
| Leu$_4$peptide 3 (SEQ ID NO:10) | 8 | 7 | 3 | 3 | n.s. |
| Ser$_7$peptide 3 (SEQ ID NO:11) | 7 | 6 | 3 | 4 | n.s. |
| Ile$_{11}$peptide 3 (SEQ ID NO:13) | 6 | 4 | 2 | 7 | n.s. |
| Leu$_4$ile$_{11}$peptide 3 (SEQ ID NO:14) | 2 | 1 | 3 | 3 | n.s. |
| Ser$_7$Glu$_8$Glu$_9$pep 3 (SEQ ID NO:12) | 7 | 2 | 9 | 5 | n.s. |
| WVQ (SEQ ID NO:33) | 8 | <1 | <1 | <1 | n.s. |
| KQK (SEQ ID NO:31) | 7 | n.s. | n.s. | n.s. | n.s. |
| SEE (SEQ ID NO:27) | n.s. | 6 | n.s. | n.s. | n.s. |

Peptide 3(7–12)[MCP-1] (SEQ ID NO:9) showed essentially no selectivity, inhibiting migration by all chemokines tested with an ED$_{50}$ in the range of 7–9 μM. Peptide 3(1–6)[MCP-1] (SEQ ID NO:8) was much less efficient at inhibiting the CC chemokines (ED$_{50}$ of about 30 μM) but only slightly less efficient at inhibiting CXC chemokines (18 μM) compared with peptide 3(1–12)[MCP-1] (SEQ ID NO:1). The selectivity ratio is defined as the average ED$_{50}$ for MCP-1 and MIP1α divided by the average ED$_{50}$ for IL-8 and SDF1α. Selectivity ratios of greater than 1 indicate greater inhibition of CC chemokines relative to CXC chemokines; selectivity ratios of less than 1 indicate greater inhibition of CXC chemokines relative to CC chemokines; and a selectivity ratio of 1 indicates that both families of cytokines are inhibited to the same extent. Hence, although it is overall a markedly weaker inhibitor of chemokine signaling, peptide 3(1–6)[MCP-1] (SEQ ID NO:8) showed a 2-fold selectivity for CXC chemokines. Thus, peptide 3(1–6)[MCP-1] (SEQ ID NO: 8) is a preferred inhibitor of the CXC chemokines, with a selectivity ratio of 0.7, while peptide 3(7–12)[MCP-1] (SEQ ID NO:9) is a preferred inhibitor of both classes of chemokines, with a selectivity ratio of 1.1. The selectivity ratio for peptide 3(1–12)[MCP-1] (SEQ ID NO:1) is 1.5.

Peptide 3(3–12)[MCP-1] (SEQ ID NO:7) had very similar properties to peptide 3(1–12) [MCP-1] (SEQ ID NO:1). This result suggested that the glutamate (E) and isoleucine (I) residues at positions 1 and 2 of the peptide 3(1–12)[MCP-1] (SEQ ID NO:1) sequence, which are not conserved in chemokine sequences other than MCP-1, are unimportant for receptor binding. Alignment of all human chemokine sequences in the peptide 3 region indicate a common conserved motif present in almost all chemokines whether of the alpha or beta subfamily (Table 3). This motif is: Cx$_1$DPx$_2$x$_3$x$_4$Wx$_5$Q.

Furthermore, there is a pattern of amino acids in the variable positions $x_1$ through $x_5$ which suggests that the nature of the amino acid at these positions may play a role in determining the selectivity of receptor binding. For example, in the CC chemokine family, position $x_1$ is usually occupied by alanine (A), whereas this position in commonly leucine (L) in the CXC chemokines except in SDF1 (Isoleucine (I) in SDF-1). To test this hypothesis, the selectivity of Leu$_4$peptide 3(1–12)[MCP-1] (SEQ ID NO:10) was compared to peptide 3(1–12)[MCP-1] (SEQ ID NO:1). While Leu$_4$peptide 3(1–12)[MCP-1] (SEQ ID NO:10) showed an approximately 4-fold increase in potency as an inhibitor of CXC chemokines compared with ala-containing peptide 3(1–12)[MCP-1] (SEQ ID NO:1), there was no decrease in the potency of CC chemokine inhibition (Table 6). Thus, Leu$_4$peptide 3(1–12)[MCP-10] (SEQ ID NO:10) showed some CXC selectivity (a selectivity ratio of 0.37) and was the most CXC selective of all the derivatives tested other than the tripeptides (see below).

As noted for position $x_1$ above, only three different amino acids appear at position $x_5$ (Table 3). Most chemokines have valine (V) at position $x_5$ as do the CXC chemokines IL-8 and MIP. In contrast, SDF-1 and IP10 have isoleucine (I) at this position, while ENA78 is the only chemokine with leucine (L) at this position. The results showed that Ile$_{11}$peptide 3(1–12)[MCP-1] (SEQ ID NO:13) showed some CXC selectivity, though not as marked as Leu$_4$peptide 3(1–12) [MCP-1] (SEQ ID NO:10) (a selectivity ratio of 0.9), but surprisingly showed the greatest selectivity for IL-8 (which has valine at this position) not SDF-1. This analog was the most selective inhibitor of IL-8 signaling other than the tripeptides, i.e., the analog had a selectivity of IL-8 over other chemokines by about 3 fold.

An analog having both the Leu$_4$ and Ile$_{11}$ substitutions did not show any greater specificity as an inhibitor of CXC chemokines than either single mutant Leu$_4$peptide 3(1–12) [MCP-1] (SEQ ID NO:10) or Ile$_{11}$peptide 3(1–12)[MCP-1] (SEQ ID NO:13) (Table 6). However, Leu$_4$Ile$_{11}$peptide 3(1–12)[MCP-1] (SEQ ID NO:14) was approximately 5-fold more potent as an inhibitor of CC chemokines than peptide 3(1–12)[MCP-1] (SEQ ID NO: 1), or the single mutants Leu$_4$peptide 3(1–12)[MCP-1] (SEQ ID NO: 10) or Ile$_{11}$peptide 3(1–12)[MCP-1] (SEQ ID NO: 13). Thus, Leu$_4$Ile$_{11}$peptide 3(1–12)[MCP-1] (SEQ ID NO:14) was a more potent general chemokine inhibitor, with an average ED$_{50}$ of 2.3 $\mu$M compared with 10 $\mu$M for peptide 3(1–12) [MCP-1] (SEQ ID NO:1). Furthermore, the Leu$_4$Ile$_{11}$peptide 3(1–12)[MCP-1] (SEQ ID NO:14) unexpectedly preserved the modest CC selectivity of peptide 3(1–12)[MCP-1] (SEQ ID NO: 1) with a selectivity ratio of 2.0. Surprisingly, therefore, the Leu$_4$Ile$_{11}$peptide 3(1–12)[MCP-1] (SEQ ID NO:14) was approximately 5-fold more potent as an inhibitor of MCP-1 signaling than peptide 3(1–12)[MCP-1] (SEQ ID NO:1), despite the fact that peptide 3(1–12)[MCP-1] (SEQ ID NO:1) contains the cognate sequence from human MCP-1. Moreover, it was found that the Leu$_4$ile$_{11}$peptide 3(3–12)[MCP-1] (SEQ ID NO:1), like Leu$_4$ile$_{11}$peptide 3(1–12)[MCP-1] (SEQ ID NO:14), was a higher affinity peptide analog of peptide 3(1–12)[MCP-1] (SEQ ID NO:1).

For positions $x_2$ through $x_4$, all chemokines described to date have at least one charged amino acid in this tripeptide region (Table 3). Many chemokines have two basic residues occupying $x_2$ and $x_4$ (e.g., KQK in MCP-1, KER in MCP-2 and KLK in SDF-1) while others have two acidic residues (e.g., SEE in MIP1$\alpha$, SES in MIP1$\beta$, and SES in RANTES). A recent report (*Nature Med.*, 3, 367 (1997)) suggested that the charge in the extracellular loops of the chemokine receptors may be an important determinant of ligand specificity, e.g., CXCR4 which binds SDF-1 is negatively charged, while CCR5, which binds MIP1$\alpha$, MIP1$\beta$ and RANTES is positively charged. Thus, residues $x_2$-$x_4$ may play an important role in receptor specificity.

To test this hypothesis, several variants were prepared: Ser$_7$peptide 3(1–12)[MCP-1] (SEQ ID NO: 11) substitutes the positively charged K residue present in MCP-1, MCP-2, Eotaxin, IL-8 and SDF-1 with the hydroxylated S residue present in MIP-1$\alpha$, MIP1$\beta$ and RANTES. However, this alteration did not markedly alter the selectivity. In particular, this alteration did not decrease the potency of inhibition of MCP-1 signaling, nor increase the potency of inhibition of MIP1$\alpha$ signaling (Table 6). The only detectable change was a modest shift from the moderate CC selectivity of peptide 3(1–12)[MCP-1] (SEQ ID NO: 1) to a moderate CXC selectivity of the Ser$_7$peptide 3(1–12)[MCP-1] (SEQ ID NO: 11) variant (a selectivity ratio of 0.5). Another variant, Ser$_7$Glu$_8$Glu$_9$peptide 3(1–12)[MCP-1] (SEQ ID NO: 12) which converts the peptide from being the cognate of the MCP-1 sequence to the cognate of the MIP1$\alpha$ sequence, resulted in a more selective MIP 1$\alpha$ inhibitor, although the selectivity ratio for MIP1a versus all other chemokines was only about 3 fold.

None of the peptide 3(1–12) [MCP-1] (SEQ ID NO:1) variants had any detectable activity as an inhibitor of TGF-beta induced migration of THP-1 cells, even at 100 $\mu$M (Table 6). Thus, all these variants were highly selective inhibitors of chemokine-induced signaling. There were no substitutions which altered an amino acid residue in peptide 3(1–12)[MCP-1] (SEQ ID NO:1) to any other amino acid regions found in the chemokine sequences described above which markedly reduced the potency of the general chemokine inhibition observed. However, certain alterations resulted in a marked shift in selectivity. For example, the CC selectivity of peptide 3(1–12)[MCP-1] (SEQ ID NO: 1) can be converted to CXC selectivity by mutating A to L at position 4 ($x_1$) or by mutating V to I at position 11 ($x_5$). In particular, two variants had greater than 3-fold selectivity for one chemokine over the average ED$_{50}$ for all the others, i.e., Ile$_{11}$peptide 3(1–12)[MCP-1] (SEQ ID NO:13) had weak overall selectivity for IL8 inhibition and Ser$_7$Glu8Glu$_9$peptide 3(1–12)[MCP-1] (SEQ ID NO: 12) had weak overall selectivity for MIP1$\alpha$.

In summary, although peptide 3(1–12)[MCP-1] (SEQ ID NO:1) variants varied to a small extent in their ED$_{50}$s and their specificity for either the $\alpha$ family or $\beta$ family of chemokines, nevertheless, they were all similar to peptide 3(1–12)[MCP-1] (SEQ ID NO:1). The results in Table 6 showed that peptide 3(1–12)[MCP-1] (SEQ ID NO:1) and peptide 3(1–12)[MCP-1] variants inhibited migration induced by MCP-1, MIP1$\alpha$, IL8 and SDF1$\alpha$ chemokines to a similar extent. While some peptides or peptide variants showed slight preference for CC chemokines, others showed slight preference for CXC chemokines but in no case did the CC-specificity exceed two-fold. Peptide 3(1–12)[MCP-1] (SEQ ID NO:1), peptide 3(1–6)[MCP-1] (SEQ ID NO:8) and peptide 3(7–12)[MCP-1] (SEQ ID NO:9) also showed no significant CC or CXC selectivity.

EXAMPLE 3

Identification and Characterization of Chemokine Sequences that are Functional Agonists The results described above, that peptide 2(1–15)[MCP-1] (SEQ ID NO:3) did not inhibit MCP-1 activity in the THP-1 migration assay, did not exclude the possibility that peptide 2(1–15)[MCP-1] (SEQ ID NO:3) associates with the MCP-1 receptor and either fails to inhibit MCP-1 binding and signaling, or acts as an agonist, preventing binding of MCP-1 but transducing an MCP-1 like signal. To determine whether peptide 2(1–15)[MCP-1] (SEQ ID NO:3) binds to chemokine receptors, THP-1 cells were mixed with a biotinylated derivative of peptide. Peptide 2(1–15)[MCP-1] (SEQ ID NO:3) was found to bind to THP-1 cells with a reasonable affinity (kD=1.9 $\mu$M), suggesting that peptide 2(1–15)[MCP-1] (SEQ ID NO:3) was able to interact with chemokine receptors without inhibiting chemokine signaling (a neutral binding agent).

Unlike peptide 3, which represents a region that is relatively conserved between chemokines, there is much less marked sequence similarity in the peptide 2 region of chemokines. Thus, peptide 2, derivatives or variants thereof, may possess more chemokine-specific effects. To test this hypothesis, the binding of biotinylated peptide 2(1–15) [MCP-1] (SEQ ID NO:3) to two different cell types, i.e., THP-1 cells and Jurkat cells, was compared. THP-1 cells express receptors for MCP-1, MIP1$\alpha$, SDF-1$\alpha$ and IL-8 while Jurkat cells express functional receptors for SDF-1 only. Peptide 2(1–15)[MCP-1] (SEQ ID NO:3) bound to Jurkat cells with a similar kD (3 $\mu$M) to THP-1 cells (1.9 $\mu$M). This observation suggests that, surprisingly, peptide 2(1–15)[MCP-1] (SEQ ID NO:3) was able to bind to a number of different chemokine receptors, although the sequence of peptide 2(1–15)[MCP-1] (SEQ ID NO:3) shows little homology to the equivalent region from SDF-1.

The functional agonist properties of peptide 2(1–15) [MCP-1] (SEQ ID NO:3) were characterized by incubating THP-1 cells with varying concentrations of peptide 2(1–15) [MCP-1] (SEQ ID NO:3) in a migration assay. Peptide 2(1–15)[MCP-1] (SEQ ID NO:3) had weak agonist activity (promoting migration with an $ED_{50}$ of about 10 μM) with maximal migration at 100 μM, which was approximately 10% of that induced by MCP-1. Thus, at high concentrations (>20 μM) peptide 2(1–15)[MCP-1] (SEQ ID NO:3), variants or derivatives thereof, may be useful for applications which require weak MCP-1 agonist activity (for example, for the therapy of parasitic infections where increased macrophage activity is desirable). Moreover, at lower concentrations (>1 μM but <20 μM), peptide 2, peptide 2 variants or derivatives may be useful as a neutral binding agent which may affect binding of non-MCP-1 proteins to the chemokine receptors. For example, peptide 2, derivatives or variants thereof, may be useful to prevent or inhibit HIV binding to chemokine receptors without inhibiting desirable chemokine signaling.

EXAMPLE 4

Preparation and Characterization of Therapeutic Agents of the Invention for In Vivo Use A. Derivatives Peptides are generally susceptible to chemical or enzymatic hydrolysis. In particular, peptides are not normally bioavailable by the oral route since they are not stable in the acid and proteolytic environment of the stomach. Thus, chemical or enzymatic hydrolysis leads to a very short in vivo half-life for peptides. To extend the half-life of agents susceptible to hydrolysis, in vitro active agents are modified in a manner that results in a derivative which may be orally bioavailable, have improved pharmacokinetics, and the administration of which may achieve concentrations in blood that inhibit chemokine activity. For example, cyclic-reverse-D (CRD) peptides may be prepared. CRD peptides are prepared by synthesizing the reverse sequence of the peptide (C-terminal to N-terminal) using the opposite stereoisomer (D-amino acids in place of L amino acids). The resulting peptide is then cyclized via N- and C-terminal cysteine residues. These derivatives retain a very similar steric arrangement of atoms to non-CRD peptide, but are not subject to enzymatic hydrolysis. Other derivatives which may exhibit an extended half-life in vivo include thienyl or pyridyl derivatives (e.g., U.S. Pat. No. 4,992,463; U.S. Pat. No. 5,091,396).

Figure 4:
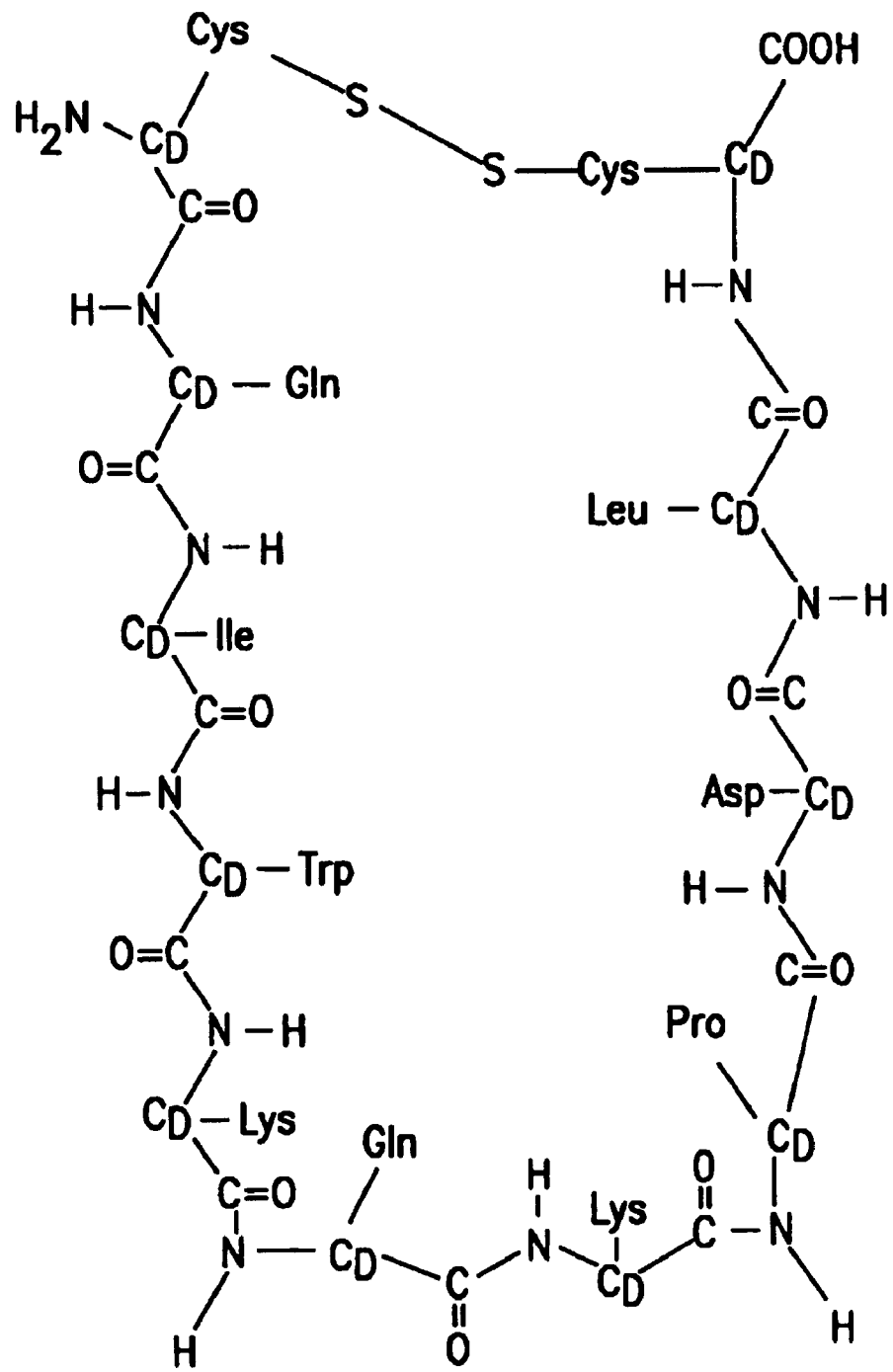
FIG. 4 shows the structure of CRD-$Cys_{13}leu_4ile_{11}$peptide 3[MCP-1](3–12)[MCP-1], which is cyclized via disulphide bonds. The main chain $\alpha$ carbons are indicated by $C_D$ which indicates that the D form of the amino acid is present.

For example, to prepare a peptide 3 derivative, peptide 3(3–12)[MCP-1] was modified according to Jameson et al. (*Nature*, 368, 744 (1994)), which yielded CRD-$Cys_{13}leu_4ile_{11}$peptide 3[MCP-1] (FIG. 4). CRD-$Cys_{13}eu_4ile_{11}$peptide 3[MCP-1], which had very similar properties to peptide 3(1–12)[MCP-1] (SEQ ID NO:1) in the in vitro assays described hereinabove, was found to be stable against both acid hydrolysis (<10% degradation at pH 2.0 for 2 hrs at 37° C.) and enzymatic destruction (5 units trypsin for 2 hrs at 37° C.). CRD-$Cys_{13}leu_4ile_{11}$peptide 3[MCP-1] was also resistant to hydrolysis in vivo and allowed therapeutically useful plasma concentrations to be achieved (>10 μM 24 hours after a single intraperitoneal dose of 1 mg of CRD-$Cys_{13}leu_4ile_{11}$peptide 3[MCP-1] in 250 μl saline).

Cyclic-reverse D (CRD), linear reverse-D (LRD), cyclic forward L (CFL), and linear forward L (LFL) (i.e., the standard form of peptides) derivatives of $leu_4ile_{11}$peptide 3 were prepared and their MCP-1 inhibitory activity in the THP-1 transwell assay determined. The results were

| | |
|---|---|
| LFL-$Leu_4ile_{11}$peptide 3 | 1–5 μM |
| LRD-$Cys_{13}Leu_4ile_{11}$peptide 3 | 200–400 nM |
| CFL-$Cys_{13}Leu_4ile_{11}$peptide 3 | 500–700 nM |
| CRD-$Cys_{13}Leu_4ile_{11}$peptide 3 | 50–100 nM |

These results show, somewhat surprisingly, that both cyclization and reverse-D derivatization independently improve activity. This improvement is then additive in the CRD derivative. Thus, cyclization improved affinity by constraining the conformations of the peptide. However, it was not expected that the reverse-D derivatization would be so beneficial, possibly by increasing stability of the molecule.

CRD-$Cys_{13}Leu_4ile_{11}$peptide 3(3–12)[MCP-1] was found to be a very potent inhibitor of MCP-1 induced THP-1 migration ($ED_{50}$<100 nM). This increased potency compared to the parent $Leu_4ile_{11}$peptide 3(1–12)[MCP-1] (SEQ ID NO:14) may reflect increased stability, even in vitro, or it may reflect the increased conformational stability of the peptide.

B. DARC Binding

A further consideration for bioavailability is non-specific binding of the therapeutic agent. Red blood cells have a signaling-deficient chemokine receptor or binding protein, termed the Duffy Antigen Receptor for Chemokines (DARC). Although it does not signal, this receptor has a high affinity for chemokines (10 nM) and may play a role in clearing them from the circulation. Unfortunately, any chemokine receptor antagonist which has a high affinity for DARC may be sequestered by the huge pool of binding sites on red blood cells, and hence unavailable to inhibit productive chemokine signaling in other tissues. Similarly, agonists which bind DARC with high affinity are unavailable to productively signal through specific chemokine receptors.

Although the interaction of chemokines with DARC is high affinity (5–10 nM association constant), kinetically the interaction is characterized by extremely rapid on and off rates. Consequently, incubation with labeled chemokine leads to saturation of the DARC binding sites, but most of the bound label is lost within minutes of removing the unbound label (>90% loss within 3 minutes). As a result, it is difficult to directly determine the binding of peptides to DARC by assaying direct binding of biotinylated peptide, since the rapid off rates make determination of the amount of bound label impossible or inaccurate.

To overcome this difficulty, the ka for association of DARC with peptide 3(1–12)[MCP-1] (SEQ ID NO:1) and peptide 2(1–15)[MCP-1] (SEQ ID NO:3) was estimated by incubating red blood cells expressing DARC with $^{125}I$-labeled MCP-1 in the presence of varying concentrations of peptide. After binding has reached equilibrium (30 minutes at 37° C.), the cells are separated from the unbound label by centrifugation for 5 minutes through a sucrose gradient. Counts associated with the cells are then determined by gamma-counting scintigraphy. In the absence of all peptides, the association constant for $^{125}I$-labeled MCP-1 on human red blood cells was 5.45 nM, a value which is in accord with a previous report. Furthermore, Scatchard analysis confirms the presence of a single high affinity binding site with 500–1000 copies per cell, consistent with the known properties of DARC. Thus, determination of $^{125}I$-MCP-1 binding to red blood cells in this assay in the presence of various concentrations of the peptide(s) allows the association constant of the peptide for DARC to be accurately estimated.

The DARC specificity ratio is also determined. The DARC specificity ratio is defined as the estimated ka for association with DARC divided by the $ED_{50}$ for biological activity. A DARC specificity ratio greater than 1 indicates that a peptide associates poorly with DARC and is bioavailable for modulating chemokine signaling, either as an antagonist or agonist. A DARC specificity ratio of about 1 indicates that the peptide binds DARC and the THP-1 signaling receptors with similar affinity. Thus, it may be difficult to achieve biologically active (as a chemokine inhibitor) concentrations of these peptides in vivo without further modifications of the peptide. A DARC specificity ratio less than 1 indicates much higher affinity for DARC than for chemokine signaling receptors.

Peptide 1[MCP-1] (SEQ ID NO:2) (which does not bind to chemokine receptors but functions in a dominant negative fashion) showed no binding to DARC (estimated ka>100 $\mu$M). In marked contrast, the weak agonist peptide 2(1-15) [MCP-1] (SEQ ID NO:3) showed high affinity binding to DARC. The association constant for peptide 2(1–15) [MCP1] (SEQ ID NO:3) for chemokine receptors on THP-1 cells was estimated at 2 $\mu$M using competition binding analysis. However, this peptide had an affinity for DARC of less than 500 nM, also assessed by competition binding analysis, using red blood cells. Thus, peptide 2(1–15) [MCP-1] (SEQ ID NO:3) binds to THP-1 cell chemokine receptors, although it does not inhibit signaling through the receptors, and it binds DARC even more strongly (DARC selectivity ratio=0.1–0.2). Thus, peptide 2 is a preferred therapeutic agent for the treatment or prevention of malaria (an action requiring DARC inhibition, but not modulation of chemokine signaling).

Peptides, such as peptide 2(1–15)[MCP-1] (SEQ ID NO:3) which have very high affinity for the DARC receptor, may have strong biological agonist activity in vivo (although they are only weak agonists or neutral agonists in vitro). Moreover, peptide 2, variants and derivatives thereof may be strongly pro-inflammatory in vivo, or strongly exacerbate existing inflammation by preventing DARC from performing the function of binding chemokines. If DARC functions as a sink to remove chemokines from the circulation, then the concentration of chemokines may be markedly increased by the presence of peptide 2. Under conditions where chemokines are being made a released into the circulation (e.g., during inflammation), peptide 2 may exacerbate that inflammation, allow the inflammation to persist longer than in the absence of the peptide or otherwise change the qualitative nature of the inflammatory reaction. For these reasons, peptides with a low DARC specificity ratio are useful for the treatment of conditions which require improved immune function, or conditions which are characterized by a pathologically inadequate inflammatory response.

MIP1-$\alpha$ has previously been shown to be the only chemokine which does not bind with significant affinity to DARC. Peptide 2(1–15)[MIP1-$\alpha$] (SEQ ID NO:5) was a potent receptor binding agent for the MIP1-$\alpha$ receptor and had excellent specificity over DARC. That is, peptide 2[MIP1$\alpha$] (SEQ ID NO:5) did not bind to DARC (association constant>50 $\mu$M) but bound strongly to chemokine receptors on THP-1 cells (association constant= 100–900 nM; number of binding sites is about 150,000 per cell). Moreover, this agent did not inhibit THP-1 cell migration induced by MCP-1, MIP1$\alpha$, IL-8, or SDF1$\alpha$. Thus, this agent may be useful as a neutral chemokine receptor binding agent in vivo, highly selective over DARC.

Peptide 3(1–12)[MCP-1] (SEQ ID NO:1) also binds to DARC, although it binds to DARC with only a similar affinity to which it binds to the chemokine receptors (low $\mu$M concentration range). $Leu_4ile_{11}$peptide 3(1–12)[MCP-1] (SEQ ID NO:14) had essentially no DARC binding capacity, while inhibiting MCP1 induced migration at concentrations around 1 $\mu$M. Thus, peptide 3 derivatives, such as $leu_4ile_{11}$peptide 3(1–12)[MCP-1] (SEQ ID NO:14) may achieve antagonist properties in vivo.

The shorter subunits of peptide 3[MCP-1] (e.g., peptide 3(7–12)[MCP-1] (SEQ ID NO:9)) showed progressively higher DARC specificity ratios (about 3.0 for peptide 3(7–12)[MCP-1] (SEQ ID NO:9) versus 1.0 for peptide 3(1–12)[MCP-1] (SEQ ID NO: 1)), indicating that where chemokine signaling receptor specificity is desired, shorter peptide subunits which retain full chemokine antagonist or agonist activity are in general to be preferred over the full length peptides.

Peptide 3(1–12)[MCP-1] (SEQ ID NO:1) (DARC specificity ratio=1.00) is unlikely to be useful as a pan-chemokine inhibitor in vivo, whereas the $Leu_4ile_{11}$peptide 3 [MCP-1] (SEQ ID NO:14) (DARC specificity ratio=37.83), or its derivatives such as $CRD-Cys_{13}leu_4ile_{11}$peptide 3[MCP-1] (3–12)[MCP-1], which did not bind to DARC (association constant=90 $\mu$M) but bound very strongly to chemokine receptors on THP-1 cells (association constant=100–500 nM; number of binding sites is about 150,000 per cell), are a preferred embodiment for the treatment or prevention of atherosclerosis, osteoporosis, and autoimmune diseases, and HIV infection (chemokine signaling receptor binding functions).

Moreover, $CRD-Cys_{13}leu_4ile_{11}$peptide 3[MCP-1](3–12) [MCP-1] inhibited THP-1 cell migration induced by MCP-1, MIP1$\alpha$, IL-8, and SDF1, with very similar $ED_{50}$s.

An alternative approach to preparing agents that are bioavailable is the preparation of non-peptide analogs of chemokines. A preferred non-peptide analog of the invention includes an isostere of WIQ, e.g., a compound of formula (IV), wherein Z=$CH_3$; Y=O; X=$CH_3$; and Ar=indolyl. This compound did not bind to DARC (association constant=>30 $\mu$M) but bound very strongly to chemokine receptors to THP- 1 cells (association constant=100 nM-1 $\mu$M; number of binding sites is about 150,000 per cell). This agent inhibited THP-1 cell migration induced by MCP-1, MIP1$\alpha$, IL-8 and SDF1$\alpha$ with very similar $ED_{50}$s.

TABLE 7

| PEPTIDE | SEQUENCE | CC SPECIFICITY[a] | DUFFY SELECTIVITY[b] | AVERAGE $ED_{50}$[c] |
|---|---|---|---|---|
| Pep2[MCP1] | SYRRITSSKCPKEAV (SEQ ID NO:3) | — | 0.18[d] | 2[c] |
| Pep2[SDF1] | HLKILNTPNCALQIV (SEQ ID NO:4) | — | <1[d] | 1–10[c] |
| Pep2[MIP1$\alpha$] | DYFETSSQCSKPGV (SEQ ID NO:5) | — | >100[d] | 1–10[c] |
| Pep2[IL8] | ELRVIESGPHCANTEI (SEQ ID NO:6) | — | <1[d] | 1–10[c] |
| Pep3 | EICADPKQKWVQ (SEQ ID NO:1) | 1.5 | 1.00 | 10 |
| Pep3[3–12] | CADPKQKWVQ (SEQ ID NO:7) | 1.2 | 1.21 | 8 |

TABLE 7-continued

| PEPTIDE | SEQUENCE | CC SPECIFICITY[a] | DUFFY SELECTIVITY[b] | AVERAGE $ED_{50}$[c] |
|---|---|---|---|---|
| Pep3[1–6] | EICADP (SEQ ID NO:8) | 0.7 | 5.32 | 24 |
| Pep3[7–12] | KQKWVQ (SEQ ID NO:9) | 1.0 | 2.94 | 6 |
| $Leu_4$pep3 | EICLDPKQKWVQ (SEQ ID NO:10) | 0.4 | n.d. | 5 |
| $Ser_7$pep3 | EICADPSQKWVQ (SEQ ID NO:11) | 0.5 | 2.00 | 5 |
| $Ile_{11}$pep3 | EICADPKQKWIQ (SEQ ID NO:12) | 0.9 | n.d | 5 |
| $Leu_4ile_{11}$pep3 | EICLDPKQKWIQ (SEQ ID NO: 13) | 2.0 | 37.83 | 2 |
| $Ser_7Glu_8Glu_9$ | EICADPSEEQVQ (SEQ ID NO:2) | 1.6 | 0.59 | 6 |
| — | KQK (SEQ ID NO:51) | >100 | 22.34 | 6[f] |
| Pep3[10–12] | WVQ (SEQ ID NO:33) | 1.1 | 24.81 | 2 |
| — | WIQ (SEQ ID NO:34) | 1.0 | n.d. | 2 |
| — | SEE (SEQ ID NO:27) | >100 | n.d. | 0.8[f] |
| — | KLK (SEQ ID NO:28) | <0.1 | n.d. | 0.1–10[f] |
| — | KEN (SEQ ID NO:55) | <0.1 | n.d. | 0.1–10[f] |
| CRD-$Cys_{13}$pep3[3–12] | -CQVWKQKPDA C- | n.d | 8.82 | 0.8 |
| LRD-$Cys_{13}leu_4ile_{11}$pep3[3–12] | CQVWKQKPDAC | n.d. | 4.59 | 1 |
| CRD-$Cys_{13}leu_4ile_{11}$pep3[3–12] | -CQIWKQKPDLC- | n.d | >100 | 0.1 |

Footnotes
[a]'CC-specificity' is the average inhibitory $ED_{50}$ versus SDF1 and IL8 divided by average inhibitory $ED_{50}$ versus MCP-1 and MIP1α.
[b]'Duffy selectivity' is the estimated ka for binding to red blood cells divided by average inhibitory $ED_{50}$ versus each of the chemokines (except for peptide 2; see footnote d below).
[c]'Average $ED_{50}$' is the average inhibitory $ED_{50}$ for inhibition of THP-1 migration induced by each of the chemokines (except for peptide 2; see footnote e below).
[d]For the peptide 2 family, the 'average $ED_{50}$' is the estimated ka for binding to THP-1 cells.
[e]For the peptide 2 family, the 'Duffy selectivity' is calculated as the ka for binding to red blood cells divided by the ka for binding THP1-1 cells.
[f]For tripeptide derivatives so marked, the peptide is highly specific for one of the four exemplary chemokines. In these cases, the $ED_{50}$ shown is for inhibition of that chemokine.
n.d. = not determined.
Abbreviations
CRD = Cyclic reverse-D derivative
LRD = Linear reverse-D derivative
CFL = Cyclic derivative of standard L-form peptide
LFL = Standard, linear L-form peptide [NB; all peptides are LFL unless stated otherwide]
Amino acids in italics are D-form amino acids, all others are L-form
— = Cyclization linking two cysteines so marked

EXAMPLE 5

Anti-HIV Activity of the Agents of the Invention

Figure 3:
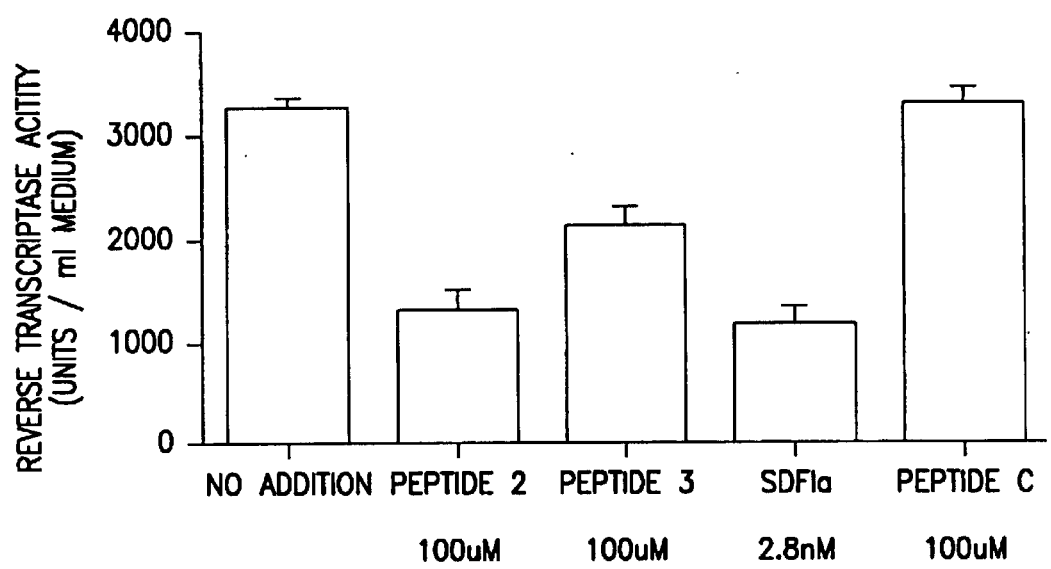
FIG. 3 shows the reverse transcriptase activity present in the culture medium at day 21 after infection of Jurkat cells with a T-tropic HIV. Peptides were added on day 0, one hour prior to infection of the cells with HIV isolate. The full length chemokine SDF-1$\alpha$ was used as a positive control.

To demonstrate that the agents of the invention inhibit HIV binding and infection of cells, human T-cell derived Jurkat cells were incubated with an infectious T-tropic HIV isolate in the presence of (i) no inhibitor, (ii) peptide C (Table 5) as an inactive control peptide, (iii) 100 µM peptide 3(1–12)[MCP-1] (SEQ ID NO:1), or (iv) 100 ng/ml SDF-1, which should bind to and block all CXCR-4 receptors. After 3 weeks in culture, viral replication was assessed by a reverse transcriptase assay of the culture medium. Peptide 3(1–12)[MCP-1] (SEQ ID NO:1) was found to be an effective inhibitor of Jurkat cell infection by HIV (FIG. 3).

Since peptide 2(1–15)[MCP1] (SEQ ID NO:3) binds to chemokine receptors on the surface of Jurkat cells and THP-1 cells, but does not inhibit productive signaling by chemokines, it is possible that peptide 2(1–15)[MCP-1] (SEQ ID NO:3) binds and inhibits an epitope used by HIV for cell entry but not by MCP-1 for signaling. To test this hypothesis, the same HIV infection assay described above was employed to test whether peptide 2(1–15)[MCP-1] (SEQ ID NO:3) inhibits HIV infection of Jurkat cells. At 100 µM, peptide 2(1–15)[MCP-1] (SEQ ID NO:3) was more effective than peptide 3(1–12)[MCP-1] (SEQ ID NO:1), and as effective as SDF1α, in preventing virus entry.

Moreover, since peptide 3(1–12)[MCP-1] (SEQ ID NO:1) and peptide 2(1–15)[MCP-1] (SEQ ID NO:3) inhibit binding to both CCR-5 and CXCR-4, the administration of peptide 3, variants or derivatives thereof, or peptide 2, variants or derivatives thereof, may inhibit productive infections by both M-tropic and T-tropic isolates.

Current therapies for inhibition of HIV focus on the virus, for example reverse transcriptase inhibitors or viral protease inhibitors. These therapies are only effective for a limited period. In each case, the efficacy is reduced because the virus is undergoing rapid replication, and there is selection in favor of mutants which are resistant to the inhibitors. Although combination therapies are more effective, they are unlikely to result in clearance of the virus from an infected individual. Eventually, mutant virus will arise which circumvents the drug cocktail and progression will again occur in the now drug-resistant individual. Thus, strategies which are based on co-receptor inhibition target a host protein, rather than a virus protein, may have increased efficacy as more extensive mutations in the virus may be necessary to circumvent an inhibited co-receptor. Indeed, the resistance to infection of CCR-5Δ32 homozygotes suggests that the virus cannot readily adapt to use of an alternative co-receptor, at least while the virus population is small.

EXAMPLE 6

Preparation and Characterization of Tripeptide Therapeutic Agents of the Invention To determine whether subunits of peptide 3(1–12)[MCP-1] (SEQ ID NO:1) possessed biological activity, subunits of peptide 3 were prepared. Peptide 3(10–12)[MCP-1], i.e., WVQ was found to be a potent inhibitor of all chemokines tested. The amino acid residues at positions 10–12 (WVQ) are conserved in many other chemokines, e.g., MCP-3, MIP1α, MIP1β, RANTES, EOTAXIN, and IL8, although SDF1 has the sequence WIQ. WVQ inhibited all four of the exemplary chemokines tested, although, unlike peptide 3(1–12)[MCP-1] (SEQ ID NO: 1), it was a more potent inhibitor of all the chemokines other than MCP-1, with $ED_{50}$s around 1 μM. Thus, these tripeptides, WVQ and WIQ, as well as non-peptide analogs based on these tripeptides, are pan-specific chemokine inhibitors. Moreover, it was found that WVQ had good Duffy selectivity (i.e., selectivity of 10).

Peptide 3(7–9)[MCP-1], i.e, KQK, did not bind to DARC (association constant=>50 μM) but bound strongly to chemokine receptors on THP-1 cells (association constant= 500 nM-1 μM; number of binding sites is about 15,000 per cell). This agent inhibited THP-1 cell migration induced by MCP-1, but did not inhibit migration induced by MIP1α, IL-8 or SDF1α. Thus, KQK with an $ED_{50}$=2–5 μM was found to be a specific inhibitor of MCP-1, i.e., it had no effect on MIP1α, SDF1α or IL8 induced activity even at 100 μM. Four tripeptides and a dipeptide of random sequence (RGD, GGR, TTT, APG, and VE) were also tested. None of these significantly inhibited migration induced by any of the chemokines. Thus, the tripeptide KQK was specific for inhibiting MCP-1 activity, showing more than 100-fold specificity for MCP-1 over all the other chemokines tested.

Tripeptide equivalents of KQK from MIP1α, SDF1α and IL8, based on an alignment of conserved cysteine residues in chemokine sequences, were then tested for their inhibition of chemokine-induced THP-1 migration. In each case, the tripeptide was highly specific for its cognate chemokine (>100-fold specific in each case). For example, SEE, the cognate peptide from MIP-α, showed greater than 100-fold selectivity for MIP1-α over the other chemokines. Moreover, KLK was a specific and potent inhibitor of SDF1, and KEN was a specific and potent inhibitor of IL8. In no case did the tripeptide significantly inhibit migration induced by any of the non-cognate chemokines, even at 100 μM. It is envisioned that tripeptides in which a conservative substitution is made may have the same specificity as the native tripeptide. Moreover, the corresponding tripeptides in other chemokines may be specific for their cognate chemokines.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified peptide which is Cys-Leu-Asp-Pro-Lys-Gln-Lys-Trp-Ile-Gln (SEQ ID NO:85).

2. A cyclic reverse sequence derivative (CRD) of Cys-Leu-Asp-Pro-Lys-Gln-Lys-Trp-Ile-Gln-Cys.

* * * * *